US008691837B2

(12) United States Patent
Krepski et al.

(10) Patent No.: US 8,691,837 B2
(45) Date of Patent: Apr. 8, 2014

(54) SUBSTITUTED IMIDAZO RING SYSTEMS AND METHODS

(75) Inventors: Larry R. Krepski, White Bear Lake, MN (US); Joseph F. Dellaria, Jr., Woodbury, MN (US); Daniel E. Duffy, White Bear Lake Township, MN (US); Matthew R. Radmer, Robbinsdale, MN (US); David T. Amos, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1320 days.

(21) Appl. No.: 10/595,959

(22) PCT Filed: Nov. 24, 2004

(86) PCT No.: PCT/US2004/039512
§ 371 (c)(1),
(2), (4) Date: May 22, 2006

(87) PCT Pub. No.: WO2005/051317
PCT Pub. Date: Jun. 9, 2005

(65) Prior Publication Data
US 2007/0072893 A1      Mar. 29, 2007

Related U.S. Application Data

(60) Provisional application No. 60/524,961, filed on Nov. 25, 2003, provisional application No. 60/580,139, filed on Jun. 16, 2004.

(51) Int. Cl.
*A61K 31/4375* (2006.01)
*C07D 471/04* (2006.01)

(52) U.S. Cl.
USPC ............................................. 514/290; 546/81

(58) Field of Classification Search
USPC ............................................ 546/81; 514/290
See application file for complete search history.

(56) References Cited

U.S. PATENT DOCUMENTS

| | | |
|---|---|---|
| 3,314,941 A | 4/1967 | Littell et al. |
| 3,412,093 A | 11/1968 | Podesva |
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster |
| 5,268,376 A | 12/1993 | Gerster |
| 5,274,113 A | 12/1993 | Kang et al. |
| 5,342,784 A | 8/1994 | Yamada et al. |
| 5,346,905 A | 9/1994 | Gerster |
| 5,352,680 A | 10/1994 | Portoghese et al. |
| 5,352,784 A | 10/1994 | Nikolaides et al. |

(Continued)

FOREIGN PATENT DOCUMENTS

AU    2004220534 A1    9/2004
AU    2004229478 A1    10/2004

(Continued)

OTHER PUBLICATIONS

Wozniak et al. "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.
Brennan et al., "Automated Bioassay of Interferons in Micro-test Plates.", *Biotechniques*, June/July, 78, 1983.
Testerman et al., "Cytokine Induction by the Immunomodulators Imiquimod and S-27609.", *Journal of Leukocyte Biology*, vol. 58, pp. 365-372, Sep. 1995.
Bachman et al., "Synthesis of Substituted Quinolylamines. Derivatives of 4-Amino-7-Chloroquinoline.", *J. Org. Chem*, 15, pp. 1278-1284 (1950).
Jain et al., "Chemical and Pharmacological Investigations of Some ω-Substituted Alkylamino-3-aminopyridines.", *J. Med. Chem.*, 11, pp. 87-92 (1968).
Baranov et al., "Pyrazoles, Imidazoles, and Other 5-Membered Rings.", *Chem. Abs.* 85, 94362, (1976).
Berényi et al., "Ring Transformation of Condensed Dihydro-astriazines.", *J. Heterocyclic Chem.*, 18, pp. 1537-1540 (1981).
Choliet et al., "Development of a Topically Active Imiquimod Formulation.", *Pharmaceutical Development and Technology*, 4(1), pp. 35-43 (1999).

(Continued)

Primary Examiner — Rita Desai

(57) ABSTRACT

Imidazo ring systems substituted at the 1-position, pharmaceutical compositions containing the compounds, intermediates, methods of making the compounds, and methods of use of these compounds as immunomodulators, for inducing cytokine biosynthesis in animals and in the treatment of diseases including viral and neoplastic diseases are disclosed.

22 Claims, No Drawings

(56) References Cited

U.S. PATENT DOCUMENTS

| | | |
|---|---|---|
| 5,367,076 A | 11/1994 | Gerster |
| 5,376,501 A | 12/1994 | Marien et al. |
| 5,378,848 A | 1/1995 | Takada et al. |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,446,160 A | 8/1995 | Stucky et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster et al. |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,955,299 A | 9/1999 | Hillman et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,923 A | 8/2000 | Ely |
| 6,110,929 A | 8/2000 | Gerster et al. |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 | 9/2003 | Gerster et al. |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 | 1/2004 | Gerster et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |

(56) References Cited

U.S. PATENT DOCUMENTS

| | | |
|---|---|---|
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1* | 9/2004 | Fink et al. ..................... 435/7.2 |
| 2004/0175336 A1 | 9/2004 | Egging et al. |
| 2004/0176367 A1 | 9/2004 | Griesgraber et al. |
| 2004/0180919 A1 | 9/2004 | Miller et al. |
| 2004/0181130 A1 | 9/2004 | Miller et al. |
| 2004/0181211 A1 | 9/2004 | Graham et al. |
| 2004/0191833 A1 | 9/2004 | Fink et al. |
| 2004/0192585 A1 | 9/2004 | Owens et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2007/0060754 A1 | 3/2007 | Lindstrom et al. |
| 2007/0066639 A1 | 3/2007 | Kshirsagar et al. |
| 2007/0099901 A1 | 5/2007 | Krepski et al. |
| 2007/0155767 A1 | 7/2007 | Radmer et al. |
| 2007/0167476 A1 | 7/2007 | Kshirsagar et al. |
| 2007/0208052 A1 | 9/2007 | Prince et al. |
| 2007/0213356 A1 | 9/2007 | Merrill et al. |
| 2007/0219196 A1 | 9/2007 | Krepski et al. |
| 2007/0219228 A1 | 9/2007 | Niwas et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2008/0015184 A1 | 1/2008 | Kshirsagar et al. |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0269192 A1 | 10/2008 | Griesgraber et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0042925 A1 | 2/2009 | Kshirsagar et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |

(56) References Cited

U.S. PATENT DOCUMENTS

| | | |
|---|---|---|
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0163533 A1 | 6/2009 | Hays et al. |
| 2009/0176821 A1 | 7/2009 | Kshirsagar et al. |
| 2009/0240055 A1 | 9/2009 | Krepski et al. |
| 2009/0253695 A1 | 10/2009 | Kshirsagar et al. |
| 2009/0270443 A1 | 10/2009 | Stoermer et al. |
| 2009/0318435 A1 | 12/2009 | Hays et al. |
| 2010/0113565 A1 | 5/2010 | Gorden et al. |

FOREIGN PATENT DOCUMENTS

| | | |
|---|---|---|
| AU | 2004264336 A1 | 2/2005 |
| AU | 2004268625 A1 | 3/2005 |
| AU | 2002239547 B2 | 11/2006 |
| CA | 2044087 A1 | 12/1991 |
| CA | 2158996 A1 | 10/1994 |
| CN | 1354663 A | 6/2002 |
| EP | 0 145 340 A2 | 6/1985 |
| EP | 0 223 420 A1 | 5/1987 |
| EP | 0 310 950 A1 | 4/1989 |
| EP | 0 385 630 A2 | 9/1990 |
| EP | 0 389 302 A1 | 9/1990 |
| EP | 0 394 026 | 10/1990 |
| EP | 0 425 306 A2 | 5/1991 |
| EP | 0 510 260 A2 | 10/1992 |
| EP | 0 645 389 A1 | 3/1995 |
| EP | 0 778 277 A1 | 6/1997 |
| EP | 0 894 797 A1 | 2/1999 |
| EP | 1 082 960 A2 | 3/2001 |
| EP | 1 097 709 A2 | 5/2001 |
| EP | 1 104 764 | 6/2001 |
| EP | 1 145 340 A2 | 10/2001 |
| EP | 1 256 582 A1 | 11/2002 |
| EP | 1 341 791 A2 | 9/2003 |
| EP | 1 495 758 A2 | 1/2005 |
| HU | 34479 A2 | 3/1985 |
| HU | 210051 A2 | 6/1991 |
| HU | 218950 A2 | 9/1995 |
| IL | 73534 A | 12/1990 |
| JP | 53050197 A | 5/1978 |
| JP | 63010787 A | 1/1988 |
| JP | 4066571 A | 3/1992 |
| JP | 4327587 A | 11/1992 |
| JP | 5286973 A | 11/1993 |
| JP | 9-208584 | 8/1997 |
| JP | 11-080156 A | 3/1999 |
| JP | 11-222432 | 8/1999 |
| JP | 2000-247884 | 9/2000 |
| NZ | 545412 A | 12/2008 |
| RU | 2076105 C1 | 3/1997 |
| RU | 2127273 C1 | 3/1999 |
| RU | 2221798 C2 | 1/2004 |
| WO | WO-91/06682 A1 | 5/1991 |
| WO | WO-92/06093 A1 | 4/1992 |
| WO | WO-92/15581 A1 | 9/1992 |
| WO | WO-92/15582 A1 | 9/1992 |
| WO | WO-93/05042 A1 | 3/1993 |
| WO | WO-93/09119 A1 | 5/1993 |
| WO | WO-93/20847 A1 | 10/1993 |
| WO | WO-94/10171 A1 | 5/1994 |
| WO | WO-95/02597 A1 | 1/1995 |
| WO | WO-95/02598 A1 | 1/1995 |
| WO | WO-96/11199 A1 | 4/1996 |
| WO | WO-96/21663 A1 | 7/1996 |
| WO | WO-97/48703 A1 | 12/1997 |
| WO | WO-97/48704 A1 | 12/1997 |
| WO | WO-98/17279 A1 | 4/1998 |
| WO | WO-98/30562 A1 | 7/1998 |
| WO | WO-98/48805 A1 | 11/1998 |
| WO | WO-98/50547 A2 | 11/1998 |
| WO | WO-98/54226 A1 | 12/1998 |
| WO | WO-99/18105 A1 | 4/1999 |
| WO | WO-99/29693 A1 | 6/1999 |
| WO | WO-00/06577 A1 | 2/2000 |
| WO | WO-00/09506 A1 | 2/2000 |
| WO | WO-00/19987 A1 | 4/2000 |
| WO | WO-00/40228 A2 | 7/2000 |
| WO | WO-00/47719 A2 | 8/2000 |
| WO | WO-00/75304 A1 | 12/2000 |
| WO | WO-00/76505 A1 | 12/2000 |
| WO | WO-00/76518 A1 | 12/2000 |
| WO | WO-00/76519 A1 | 12/2000 |
| WO | WO-01/34709 A1 | 5/2001 |
| WO | WO-01/51486 A2 | 7/2001 |
| WO | WO-01/55439 A1 | 8/2001 |
| WO | WO-01/58900 A1 | 8/2001 |
| WO | WO-01/74343 A2 | 10/2001 |
| WO | WO-01/74821 A1 | 10/2001 |
| WO | WO-02/07725 A1 | 1/2002 |
| WO | WO-02/22809 A2 | 3/2002 |
| WO | WO-02/24225 A1 | 3/2002 |
| WO | WO 02/36592 | 5/2002 |
| WO | WO-02/46188 A2 | 6/2002 |
| WO | WO-02/46189 A2 | 6/2002 |
| WO | WO-02/46190 A2 | 6/2002 |
| WO | WO-02/46191 A2 | 6/2002 |
| WO | WO-02/46192 A2 | 6/2002 |
| WO | WO-02/46193 A2 | 6/2002 |
| WO | WO-02/46194 A2 | 6/2002 |
| WO | WO-02/46749 A2 | 6/2002 |
| WO | WO-02/085905 A1 | 10/2002 |
| WO | WO-02/102377 A1 | 12/2002 |
| WO | WO-03/008421 A1 | 1/2003 |
| WO | WO-03/009852 A1 | 2/2003 |
| WO | WO-03/020889 A2 | 3/2003 |
| WO | WO-03/043572 A2 | 5/2003 |
| WO | WO-03/045391 A1 | 6/2003 |
| WO | WO-03/045494 A2 | 6/2003 |
| WO | WO-03/045929 A1 | 6/2003 |
| WO | WO-03/050117 A1 | 6/2003 |
| WO | WO-03/050118 A1 | 6/2003 |
| WO | WO-03/050119 A2 | 6/2003 |
| WO | WO-03/050121 A1 | 6/2003 |
| WO | WO-03/077944 A1 | 9/2003 |
| WO | WO-03/080114 A2 | 10/2003 |
| WO | WO-03/086280 A2 | 10/2003 |
| WO | WO-03/086350 A1 | 10/2003 |
| WO | WO-03/089602 A2 | 10/2003 |
| WO | WO-03/097641 A2 | 11/2003 |
| WO | WO-03/101949 A2 | 12/2003 |
| WO | WO-03/103584 A2 | 12/2003 |
| WO | WO-2004/028539 A2 | 4/2004 |
| WO | WO-2004/041285 A1 | 5/2004 |
| WO | WO-2004/043913 A2 | 5/2004 |
| WO | WO-2004/053057 A2 | 6/2004 |
| WO | WO-2004/053452 A2 | 6/2004 |
| WO | WO-2004/058759 A1 | 7/2004 |
| WO | WO-2004/071459 A2 | 8/2004 |
| WO | WO-2004/075865 A2 | 9/2004 |
| WO | WO-2004/080398 A2 | 9/2004 |
| WO | WO-2004/091500 A2 | 10/2004 |
| WO | WO-2004/096144 A2 | 11/2004 |
| WO | WO-2004/110991 A2 | 12/2004 |
| WO | WO-2004/110992 A2 | 12/2004 |
| WO | WO-2005/003064 A2 | 1/2005 |
| WO | WO-2005/003065 A2 | 1/2005 |
| WO | WO 2005/016275 A2 | 2/2005 |
| WO | WO 2005/018551 | 3/2005 |
| WO | WO 2005/018555 | 3/2005 |
| WO | WO 2005/018556 | 3/2005 |
| WO | WO 2005/020999 | 3/2005 |
| WO | WO-2005/023190 A2 | 3/2005 |
| WO | WO-2005/025614 A2 | 3/2005 |
| WO | WO-2005/029037 A2 | 3/2005 |
| WO | WO 2005/032484 | 4/2005 |
| WO | WO-2005/041891 A2 | 5/2005 |
| WO | WO 2005/048933 | 6/2005 |
| WO | WO 2005/048945 | 6/2005 |
| WO | WO-2005/049076 A1 | 6/2005 |

(56) References Cited

FOREIGN PATENT DOCUMENTS

| | | |
|---|---|---|
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO-2005/065678 A1 | 7/2005 |
| WO | WO 2005/066169 | 7/2005 |
| WO | WO 2005/066170 | 7/2005 |
| WO | WO 2005/066172 | 7/2005 |
| WO | WO-2005/067500 A2 | 7/2005 |
| WO | WO 2005/076783 | 8/2005 |
| WO | WO 2005/079195 | 9/2005 |
| WO | WO 2005/094531 | 10/2005 |
| WO | WO-2005/110013 A2 | 11/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO-2006/063072 A2 | 6/2006 |
| WO | WO-2006/063152 A2 | 6/2006 |
| WO | WO 2006/065280 | 6/2006 |
| WO | WO-2006/073940 A2 | 7/2006 |
| WO | WO 2006/074003 | 7/2006 |
| WO | WO-2006/074045 A2 | 7/2006 |
| WO | WO 2006/004737 | 8/2006 |
| WO | WO 2006/083400 | 8/2006 |
| WO | WO 2006/083440 | 8/2006 |
| WO | WO-2006/084251 A2 | 8/2006 |
| WO | WO 2006/086449 | 8/2006 |
| WO | WO 2006/086633 | 8/2006 |
| WO | WO-2006/086634 A2 | 8/2006 |
| WO | WO-2006/091394 A2 | 8/2006 |
| WO | WO-2006/091567 A2 | 8/2006 |
| WO | WO-2006/091568 A2 | 8/2006 |
| WO | WO-2006/091647 A2 | 8/2006 |
| WO | WO-2006/093514 A2 | 9/2006 |
| WO | WO-2006/098852 A2 | 9/2006 |
| WO | WO-2006/107753 A2 | 10/2006 |
| WO | WO-2006/107771 A2 | 10/2006 |
| WO | WO-2006/107851 A1 | 10/2006 |
| WO | WO-2006/107853 A2 | 10/2006 |
| WO | WO-2006/121528 A2 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", Bioorganic & Medicinal Chemistry, 11, pp. 2541-2550 (2003).

Stewart et al., "Synthesis of a Carba-analog of S—Acetyl Coenzyme A,Acetonyldethio Coenzyme A; an Effective Inhibitor of Citrate Synthase.", Liebigs Ann. Chem., pp. 57-65 (1978).

Supplementary Partial European Search Report for EP 04812098.4 mailed May 15, 2009.

International Search Report and Written Opinion for PCT/US2004/039512 mailed Mar. 29, 2006.

International Preliminary Report on Patentability for PCT/US2004/039512 mailed Jun. 8, 2006.

[No Author Listed] "Comparative Tests." Filed Apr. 8, 2005 during prosecution for EP 00938205.2, EP 00950215.4 and EP 00938211.0 in the name of 3M Innovative Properties Co.

[No Author Listed] Chemical Abstracts. 1964;61(1):6060g.

[No Author Listed] Encyclopedia of Pharmaceutical Technology. 2nd Ed. Marcel Dekker, Inc. 2002:856-60.

Agrawal et al., Synthetic agonists of Toll-like receptors 7, 8 and 9. Biochem Soc Trans. Dec. 2007;35(Pt 6):1461-7.

Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.

Akira et al., Toll-like receptors: critical proteins linking innate and acquired immunity. Nature Immunol. 2001;2(8):675-80.

Akira et al., Recognition of pathogen-associated molecular patterns by TLR family. Immunol Lett. 2003;85:85-95.

Alexopoulou et al., Recognition of double-stranded RNA and activation of NF-kappaB by Toll-like receptor 3. Nature. Oct. 18, 2001;413(6857):732-8.

Assuma et al., IL-1 and TNF Antagonists Inhibit the Inflammatory Response and Bone Loss in Experimental Periodontitis. J Immunol. 2000;160:403-09.

Au et al., Virus-mediated induction of interferon A gene requires cooperation between multiple binding factors in the interferon alpha promoter region. J Biol Chem. Nov. 15, 1993;268(32):24032-40.

Auerbach et al., Erythema nodosum following a jellyfish sting. J Emerg Med. Nov.-Dec. 1987;5(6):487-91.

Auwers, [Uber die Isomerie-Verhaltnisse in der Pyrazol-Reihe. Berichte. VI.] 1926;601-607. German.

Baffis et al., Use of interferon for prevention of hepatocellular carcinoma in cirrhotic patients with hepatitis B or hepatitis C virus infection. Ann Intern Med. Nov. 2, 1999;131(9):696-701.

Baker et al., Oral infection with Porphyromonas gingivalis and induced alveolar bone loss in immunocompetent and severe combined immunodeficient mice. Arch Oral Biol. Dec. 1994;39(12):1035-40.

Baldwin et al., Amino Acid Synthesis via Ring Opening of N-Sulphonyl Aziridine-2-Carboxylate Esters with Organometallic Reagents. Tetrahedron. 1993;49:6309-30.

Bártová et al., Th1 and Th2 cytokine profile in patients with early onset periodontitis and their healthy siblings. Mediators Inflamm. 2000;9(2):115-20.

Beck et al., Dental Infections and Atherosclerosis. Am Heart J. 1999;13:528-33.

Beckett et al., Configurational Studies in Synthetic Analgesics: the Synthesis of (−)- Methadone from D-(−)-Alanine. J Chem Soc. 1957;1:858-61.

Beilman et al., Experimental brown spider bite in the guinea pig: Results of treatment with dapsone or hyperbaric oxygen. J Wilderness Medicine. 1994;5:287-94.

Belikov, Abbreviated Guide to Synthetic and Natural Medications. Pharmaceutical Chemistry. Higher School. 1993;1:43-47. Russian.

Beltrami et al., Some Methylhydrazonium Salts; An Improved Synthesis of Tetramethylhydrazine. J Am Chem Soc. 1956;78:2467-68.

Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.

Bertino et al., Principles of Cancer Therapy. Cecil Textbook of Medicine. Goldman et al., eds. 21th Ed. W.B. Saunders Company. 2000:1:1060-74.

(56) References Cited

OTHER PUBLICATIONS

Beutler et al., Tumor necrosis factor in the pathogenesis of infectious diseases. Crit Care Med. Oct. 1993;21(10 Suppl):S423-35.
Beutner et al., Therapeutic response of basal cell carcinoma to the immune response modifier imiquimod 5% cream. J Am Acad Dermatol. Dec. 1999;41(6):1002-7.
Beutner et al., Treatment of genital warts with an immune-response modifier (imiquimod). J Am Acad Dermatol. Feb. 1998;38(2 Pt 1):230-9.
Binder, Acute arthropod envenomation. Incidence, clinical features and management. Med Toxicol Adverse Drug Exp. May-Jun. 1989;4(3):163-73.
Bishop et al., Molecular mechanisms of B lymphocyte activation by the immune response modifier R-848. J Immunol. Nov. 15, 2000;165(10):5552-7.
Bitterman-Deutsch et al., [Brown spider bite]. Harefuah. Sep. 1990;119(5-6):137-9. Hebrew.
Booth et al., Dapsone suppresses integrin-mediated neutrophil adherence function. J Invest Dermatol. Feb. 1992;98(2):135-40.
Borkan et al., An outbreak of venomous spider bites in a citrus grove. Am J Trop Med Hyg. Mar. 1995;52(3):228-30.
Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.
Brants, The Distribution of Tobacco Mosaic Virus (TMV) in Excised Tomato Roots Cultivated in Vitro. Tijdschr Plantenziekten, 1962;68:198-207.
Brassard et al., Interferon-$\alpha$ as an immunotherapeutic protein. J Leukoc Biol. Apr. 2002;71(4):565-81.
Breathnach, Azelaic acid: potential as a general antitumoural agent. Med Hypotheses. Mar. 1999;52(3):221-6.
Broughton, Management of the brown recluse spider bite to the glans penis. Mil Med. Oct. 1996;161(10):627-9.
Buckle et al., 4-hydroxy-3-nitro-2-quinolones and related compounds as inhibitors of allergic reactions. J Med Chem. Jul. 1975;18(7):726-32.
Buisson et al., Preparation and use of (S)-O-acetyllactyl chloride (Mosandl's reagent) as a chiral derivatizing agent. Tetrahedron Assym. 1999;10:2997-3002.
Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-94.
Burleson, Chapter 14. Influenza Virus Host Resistance Model for Assessment of Immunostimulation, and Antiviral Compounds. Methods in Immunology. 1995;2:181-202.
Buschle et al., Interferon $\gamma$ inhibits apoptotic cell death in B cell chronic lymphocytic leukemia. J Exp Med. Jan. 1, 1993;177(1):213-8.
Cai et al., Evaluation of trifluoroacetic acid as an ion-pair reagent in the separation of small ionizable molecules by reversed-phase liquid chromatography. Analytica Chmica Acta. 1999;399:249-258.
Cantell et al., IFN-$\gamma$ Enhances Production of IFN-$\alpha$ in Human Macrophages but Not in Monocytes. J Interferon and Cytokine Res. 1996;16:461-63.
Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.
Carrigan et al., Synthesis and in vitro pharmacology of substituted quinoline-2,4-dicarboxylic acids as inhibitors of vesicular glutamate transport. J Med Chem. May 23, 2002;45(11):2260-76.
Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997; 330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.
Chuang et al., Toll-like receptor 9 mediates CpG-DNA signaling. J Leukoc Biol. Mar. 2002;71(3):538-44.
Claisen, [Über $\alpha$-Methyl-isoxazol.] Berichte. 1909;42:59-69. German.
Cohen et al., Cytokine function: a study in biologic diversity. Am J Clin Pathol. May 1996;105(5):589-98.
Cole et al., Brown recluse spider envenomation of the eyelid: an animal model. Ophthal Plast Reconstr Surg. Sep. 1995;11(3):153-64.
Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.
Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.
Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.
Davis, Current therapy for chronic hepatitis C. Gastroenterology. Feb. 2000;118(2 Suppl 1):S104-14.
Davis et al., Heterocyclic Syntheses with Malonyl Chloride. Part VI. 3-Substituted Pyridine Derivatives from $\alpha$-Methylene-nitriles. J Chem Soc. 1962:3638-44.
Davis et al., Self-administered topical imiquimod treatment of vulvar intraepithelial neoplasia. A report of four cases. J Reprod Med. Aug. 2000;45(8):619-23.
De et al., Structure-activity relationships for antiplasmodial activity among 7-substituted 4-aminoquinolines. J Med Chem. Dec. 3, 1998;41(25):4918-26.
Debol et al., Anti-inflammatory action of dapsone: inhibition of neutrophil adherence is associated with inhibition of chemoattractant-induced signal transduction. J Leukoc Biol. Dec. 1997;62(6):827-36.
De Clerq, Synthetic interferon inducers. Top Curr Chem. 1974;52:173-208.
Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.
Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.
Delgado, Textbook of Organic Medicinal and Pharmaceutical Chemistry, Ninth Edition, Remers, ed., 1991:30-1.
Denzel et al. Imidazo [4,5-c]- and [4,5-b]pyridines. J. Heterocyclic Chem. 1977;14:813-821.
Diaz-Arrastia et al., Clinical and molecular responses in high-grade intraepithelial neoplasia treated with topical imiquimod 5%. Clin Cancer Res. Oct. 2001;7(10):3031-3.
Di Carlo et al., Neutrophils in anti-cancer immunological strategies: old players in new games. J Hematother Stem Cell Res. Dec. 2001;10(6):739-48.
Dicken et al., Reactions at High Pressures. [3+2] Dipolar Cycloaddition of Nitrones with Vinyl Ethers. J Org Chem. 1982;47:2047-51.
Dockrell et al., Imiquimod and resiquimod as novel immunomodulators. J Antimicrob Chemother. Dec. 2001;48(6):751-5.
Dorwald, "Preface." Side Reactions in Organic Synthesis. A Guide to Successful Synthesis Design. Wiley-VCH. 2005: IX.
Douglas, Introduction to Viral Diseases. In: Cecil Textbook of Medicine. Bennet et al., eds. 20th Ed. W.B. Saunders Company. 1996:2:1739-47.
Doyle et al., Toll-like receptor 3 mediates a more potent antiviral response than Toll-like receptor 4. J Immunol. Apr. 1, 2003;170(7):3565-71.
Drexler et al., Bryostatin 1 induces differentiation of B-chronic lymphocytic leukemia cells. Blood. Oct. 1989;74(5):1747-57.
Dzionek et al. BDCA-2, BDCA-3, and BDCA-4: three markers for distinct subsets of dendritic cells in human peripheral blood. J Immunol. Dec. 1, 2000;165(11):6037-46.

(56) References Cited

OTHER PUBLICATIONS

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-α 1 or Interferon-α 2 Enhances the Production of Both Subtypes Simultaneously. J Interferon and Cytokine Res. 1995;15:637-39.

Galose, Dapsone (diaminodiphenylsulphone DDS). Clinical Toxicology Review. 1999:21(9). 3 pages.

Gendron, Loxosceles ignali Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537-45.

Gibson et al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et al., Intradermal anti-loxosceles Fab fragments attenuate dermonecrotic arachnidism. Acad Emerg Med. 1999;6:1195-202.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 27, 2002;111(7):927-30.

Gunning etal., Chemoprevention by lipoxygenase and leukotriene pathway inhibitors of vinyl carbamate-induced lung tumors in mice. Cancer Res. Aug. 1, 2002;62(15):4199-201.

Gürsel et al., Differential and competitive activation of human immune cells by distinct classes of CpG oligodeoxynucleotide. J Leukoc Biol. May 2002;71(5):813-20.

Hart, Napthyridines Hydroxynaphthyridies, Journal of Chemical Society, 1956;Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-9. Epub Jun. 26, 2003.

Hayes et al., Regulation of Interferon Production by Human Monocytes: Requirements for Priming for Lipopolysaccharide-Induced Production. J Leukocyte Biol. 1991;50:176-81.

Heil et al., Species-specific recognition of single-stranded RNA via toll-like receptor 7 and 8. Science. Mar. 5, 2004;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al. Comparison of hyperbaric oxygen and dapsone therapy for loxosceles envenomation. Acad Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides signaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Iino et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretronecanol and Lupinine. J Org Chem. 1982;47:230-33.

Jacobs, The Synthesis of Acetylenes. In: Organic Reactions. New York: Wiley & Sons, Inc., 1949. vol. 5. 1-78.

Jahnsen et al., Extensive recruitment of IL-3Rαhigh dendritic-cell precursors to allergic nasal mucosa during allergen challenge. Immunology Lett. 1999;69(1):123. Abstract #32.2.

Jurk et al. Human TLR7 and TLR8 independently confer responsiveness to the antiviral compound R-848. Nat Immunol. Jun. 2002;3(6):499.

Juweid, Radioimmunotherapy of B-Cell Non-Hodgkin's Lymphoma: From Clinical Trials to Clinical Practice. J Nuclear Med. 2002;43(11):1507-29.

Katritsky et al., Comprehensive Heterocyclic Chemistry: The Structure, Reactions, Synthesis and Uses of Heterocyclic Compounds. 1984;2:586-587.

Keating et al., Long-term follow-up of patients with chronic lymphocytic leukemia treated with fludarabine as a single agent. Blood. Jun. 1, 1993;81(11):2878-84.

(56) References Cited

OTHER PUBLICATIONS

Klausen et al., Two complementary methods of assessing periodontal bone level in rats. Scand J Dent Res. Dec. 1989;97(6):494-9.
Klinman, Immunotherapeutic uses of CpG oligodeoxynucleotides. Nat Rev Immunol. Apr. 2004;4(4):249-58.
Kloek et al., An improved method for the synthesis of stabilized primary enamines and imines. J Org Chem. 1978;43:1460-62.
Kloetzel, Reactions of nitroparaffins. I. Synthesis and reduction of some ò-nitrokenes. J Am Chem Soc. 1947;69:2271-2275.
Kornman, Host modulation as a therapeutic strategy in the treatment of periodontal disease. Clin Infect Dis. Mar. 1999;28(3):520-6.
Kourafalos et al., Synthesis of 7-aminopyrazolo[3,4-c]pyridine as a probe for the preparation of compounds of pharmacological interest. Heterocycles. 2002;57(12):2335-2343.
Krause et al., Autoimmune aspects of cytokine and anticytokine therapies. Am J Med. Oct. 1, 2003;115(5):390-7.
Krenitsky et al., Imidazo[4,5-c]pyridines (3-deazapurines) and their nucleosides as immunosuppressive and anti-inflammatory agents. J Med Chem. Jan. 1986;29(1):138-43.
Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.
Lall et al., Serine and threonine beta-lactones: a new class of hepatitis A virus 3C cysteine proteinase inhibitors. J Org Chem. Mar. 8, 2002;67(5):1536-47.
Lee et al., p38 mitogen-activated protein kinase inhibitors—mechanisms and therapeutic potentials. Pharmacol Ther. 1999;82:389-97.
Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.
Lehner et al., The role of γδ cells and β-chemokines in mucosal protection against SIV infection. Immunology Lett. 1999;69:25-192. Abstract 2.1.
Levy et al., Unique efficacy of Toll-like receptor 8 agonists in activating human neonatal antigen-presenting cells. Blood. Aug. 15, 2006;108(4):1284-90. Epub Apr. 25, 2006.
Leynadier et al., Allergic reactions to North African scorpion venom evaluated by skin test and specific IgE. J Allergy Clin Immunol. Jun. 1997;99(6 Pt 1):851-3. 4 pages.
Li et al., An improved protocol for the preparation of 3-pyridyl- and some arylboronic acids. J Org Chem. Jul. 26, 2002;67(15):5394-7.
Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;S475:Abstract 3029.
Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.
Litt et al., Mucosal delivery of vaccine antigens displayed on the surface of *Lactococcus lactis*. Immunology Lett. 1999;69(1):61. Abstract #11.26.
Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.
Loesche et al., Treatment paradigms in periodontal disease. Compend Contin Educ Dent. Mar. 1997;18(3):221-6, 228-30, 232 passim; quiz 234. Review.
Luger et al., Evidence for an epidermal cytokine network. J Invest Dermatol. Dec. 1990;95(6 Suppl):100S-104S.
Luskin et al., Olefinic Derivatives of 2,4-Diamino-s-triazines. J Org Chem. 1958;23:1032-37.
Macchia et al., Synthesis and antiviral properties of 9-[(2-methyleneaminoxyethoxy)methyl]guanine derivatives as novel Acyclovir analogues. Farmaco. Feb. 2000;55(2):104-8.
Majeski et al., Action of venom from the brown recluse spider (*Loxosceles reclusa*) on human neutrophils. Toxicon. 1977;15(5):423-7.
Makarenkova et al., Identification of delta- and mu- type opioid receptors on human and murine dendritic cells. J Neuroimmunol. 2001;117:68-77.
Male et al., Introduction to the Immune System. In: Immunology. Elsevier. 2006:6-7.
Masihi, Progress on novel immunomodulatory agents for HIV-1 infection and other infectious diseases. Expert Opin Ther Patents. 2003;13(6):867-82.
Masiukiewicz et al., Scalable Syntheses of $N^\alpha$-Benzyloxycarbonyl-$_L$-Ornithine and of $N^\alpha$-(9-Fluorenylmethoxy)Carbonyl-$_L$-Ornithine. Org Prep Proced Int. 2002;34:531-37.
Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.
Mathur et al., Cell-mediated immune system regulation in periodontal diseases. Crit Rev Oral Biol Med. 1997;8(1):76-89.
Maynor et al., Brown recluse spider envenomation: a prospective trial of hyperbaric oxygen therapy. Acad Emerg Med. Mar. 1997;4(3):184-92.
Mbow et al., Small molecule and biologic modulators of the immune response to hepatitis C virus. Mini Rev Med Chem. May 2006;6(5):527-31.
McCarthy et al., Opioids, opioid receptors, and the immune response. Drug & Alcohol Dependence. 2001;62:111-23.
McKennon et al., A Convenient Reduction of Amino Acids and Their Derivatives. J Org Chem. 1993;58:3568-71.
McLaughlin et al., Opioid growth factor (OGF) inhibits the progression of human squamous cell carcinoma of the head and neck transplanted into nude mice. Cancer Lett. 2003;199:209-17.
Medzhitov, Toll-Like Receptors and Innate Immunity. Nature Rev Immunol. 2001;1:135-45.
Mee et al., Stille coupling made easier—the synergic effect of copper(I) salts and the fluoride ion. Angew Chem. 2004;116:1152-56.
Merigian et al., Envenomation From the Brown Recluse Spider: Review of Mechanism and Treatment Options. Am J Ther. Oct. 1996;3(10):724-734.
Miller et al., Imiquimod applied topically: a novel immune response modifier and new class of drug. Int J Immunopharmacol. Jan. 1999;21(1):1-14.
Minakawa et al., Nucleosides and Nucleotides. 184. Synthesis and Conformational Investigation of Anti-Fixed 3-Deaza-3-halopurine Ribonucleosides. J Org Chem. 1999;64:7158-72.
Moebius et al., The mysteries of sigma receptors: new family members reveal a role in cholesterol synthesis. Trends Pharmacol Sci. Mar. 1997;18(3):67-70.
Moldoveanu et al., Poly-L-lysine as a potential mucosal adjuvant. Immunology Lett. 1999;69(1):62. Abstract #11.28.
Mollick et al., MUC1-like tandem repeat proteins are broadly immunogenic in cancer patients. Cancer Immun. Mar. 17, 2003;3:3. 17 pages.
Moody et al., Lipoxygenase inhibitors prevent lung carcinogenesis and inhibit non-small cell lung cancer growth. Exp Lung Res. Jul.-Aug. 1998;24(4):617-28.
Moraczewski et al., Using Hydrogen Bonding to Control Carbamate C-N Rotamer Equilibria. Org Chem. Oct. 16, 1998;63(21):7258-7262.
Mosbech et al., [Allergy to insect stings] Ugeskr Laeger. Oct. 28, 1991;153(44):3067-71. Danish.
Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.
Muller et al., An improved one-pot procedure for the synthesis of alkynes from aldehydes. Synlett. 1996;6:521-522.
Mutschler et al., 9.2 Anti-infectives. In: Drug Actions: Basic Principles and Therapeutic Aspects. 1995:515-80.
Muzio et al., Differential expression and regulation of toll-like receptors (TLR) in human leukocytes: selective expression of TLR3 in dendritic cells. J Immunol. Jun. 1, 2000;164(11):5998-6004.

(56) References Cited

OTHER PUBLICATIONS

Nagarajan et al., Condensed heterotricycles: synthesis of pyrazolo[3,4-c]quinoline derivatives. Indian Journal of Chemistry. 1992;31B:316-321.

Nagase et al., Expression and function of Toll-like receptors in eosinophils: activation by Toll-like receptor 7 ligand. J Immunol. Oct. 15, 2003;171(8):3977-82.

Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.

Ohana of al., Differential effect of adenosine on tumor and normal cell growth: focus on the A3 adenosine receptor. Journal of Cellular Physiology. Jan. 2001;186(1):19-23. Review.

O'Mahony et al., New patient-applied therapy for anogenital warts is rated favourably by patients. Intl J STD & AIDS. 2001;12:565-70.

Osol et al., Chapter 27: Structure-Activtiy Relationship and Drug Design. In: Remington's Pharmaceutical Sciences. 16th Ed. Mach Publishing. 1980:420-35.

Ottonello et al., Sulphonamides as anti-inflammatory agents: old drugs for new therapeutic strategies in neutrophilic inflammation? Clin Sci (Lond). Mar. 1995;88(3):331-6.

Ozinsky et al., The repertoire for pattern recognition of pathogens by the innate immune system is defined by cooperation between Toll-like receptors. Proc. Nat. Acad. Sci. 2000; 97(25):13766-71.

Page et al., Advances in the pathogenesis of periodontitis: summary of developments, clinical implications and future directions. Periodontol 2000. Jun. 1997;14:216-48.

Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.

Park et al., Sodium Dithionite Reduction of Nitroarenes Using Viologen as an Electron Phase-Transfer Catalyst. Tetrahedron Lett. 1993;34(46):7445-46.

Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.

Patrick et al., Paragraph 10.3: Drug optimization: strategies in drug design. In: An Introduction to Medicinal Chemistry. Oxford: Oxford University Press. Jan. 2005. 200-218.

Pavletic et al., Outcome of allogeneic stem cell transplantation for B cell chronic lymphocytic leukemia. Bone Marrow Transplant. Apr. 2000;25(7):717-22.

Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.

Payvandi et al., Exogenous and Endogenous IL-10 Regulate IFN-α Production by Peripheral Blood Mononuclear Cells in Response to Viral Stimulation. J Immunol. 1998;160:5861-68.

Peschke et al., Synthesis and in vitro characterization of new growth hormone secretagogues derived from ipamorelin with dipeptidomimetic N-terminals. Eur J Med Chem. 1999;34:363-380.

Peterson et al., The opioid-cytokine connection. J Neuroimmunol. 1998;83:63-69.

Phillips et al., Therapy of brown spider envenomation: a controlled trial of hyperbaric oxygen, dapsone, and cyproheptadine. Ann Emerg Med. Mar. 1995;25(3):363-8.

Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.

Poljakovic et al., iNOS and COX-2 immunoreactivity in the mice bladder and kidney after bacterial instillation. Immunology Lett. 1999;69(1):122. Abstract #31.5.

Powell et al., Compendium of excipients for parenteral formulations. PDA J Pharm Sci Technol. Sep.-Oct. 1998; 52(5):238-311.

Prelog et al., Cycloalkeno-pyridine. Helv Chem Acta. 1945;28:1684-93. German.

Rees et al., Brown recluse spider bites. A comparison of early surgical excision versus dapsone and delayed surgical excision. Ann Surg. Nov. 1985;202(5):659-63.

Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.

Rhodes, Discovery of immunopotentiatory drugs: current and future strategies. Clin Exp Immunol. Dec. 2002; 130(3):363-9.

Ribera et al., "Spontaneous" complete remissions in chronic lymphocytic leukemia: report of three cases and review of the literature. Blood Cells. 1987;12(2):471-79.

Ritter et al., A new reaction of nitriles; amides from alkenes and mononitriles. J Am Chem Soc. Dec. 1948;70(12):4045-8.

Rocca et al., Carbolines. Part VII. Ansidines, Convenient tools to synthesize fficien-β-carbolines. J Heterocyclic Chem. 1995;32:1171-1175.

Rocca et al., Connection between metalation and cross-coupling strategies. Anew convergent route to azacarbazoles. Tetrahedron. 1993;49(1):49-64.

Rollins, Chemokines. Blood. Aug. 1, 1997;90(3):909-28. Review.

Rosenberg et al., Treatment of 283 consecutive patients with metastatic melanoma or renal cell cancer using high-dose bolus interleukin 2. JAMA. Mar. 23-30, 1994;271(12):907-13.

Rothel et al., The use of recombinant ovine IL-1beta and TNF-alpha as natural adjuvants and their physiological effects in vivo. Immunol Cell Biol. Apr. 1998;76(2):167-72.

Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Rozman et al., Chronic lymphocytic leukemia. N Engl J Med. Oct. 19, 1995;333(16):1052-7.

Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.

Salaun et al., TLR3 Can Directly Trigger Apoptosis in Human Cancer Cells. J of Immunology. 2006;176:4894-901.

Salemink, Uber 2-Propyl-1- Und 2-Propyl-Desaza-Adenin. Recueil. 1961;80:545-55. German.

Sambhi et al., Local production of tumor necrosis factor encoded by recombinant vaccinia virus is effective in controlling viral replication in vivo. Proc Natl Acad Sci U S A. May 1, 1991;88(9):4025-9.

Sams et al., Necrotic arachnidism. J Am Acad Dermatol. Apr. 2001;44(4):561-73; quiz 573-6.

Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.

Scheerlinck, Genetic adjuvants for DNA vaccines. Vaccine. Mar. 21, 2001;19(17-19):2647-56.

Scheuer et al., Application of the Ritter reaction to mesityl oxide and chalcone. J Am Chem Soc. 1957;22:674-676.

Schofield et al., Reply. Low-Dose Interferon-alpha in Chronic Myeloid Leukemia. Ann Internal Med. 1995;122(9):728-29. 1 page.

Schwandner et al., Peptidoglycan- and lipoteichoic acid-induced cell activation is mediated by toll-like receptor 2. J Biol Chem. Jun. 18, 1999;274(25):17406-9.

Seeman et al., Steric and Conformational Effects in Nicotine Chemistry. J Org Chem. 1981;46:3040-48.

Serrat et al., A highly efficient and straightforward stereoselective synthesis of novel chiral α-acetylenic ketones. Tetrahedron: Assymmetry. 1999;10:3417-30.

Severa et al., Sensitization to TLR7 agonist in IFN-beta-preactivated dendritic cells. J Immunol. May 15, 2007;178(10):6208-16.

(56) References Cited

OTHER PUBLICATIONS

Seymour et al., Cellular immunity and hypersensitivity as components of periodontal destruction. Oral Dis. Mar. 1996;2(1):96-101. Review.

Shelburne et al., Quantitation of Bacteroids forsythus in subgingival plaque comparison on immunoassay and quantitative polymerase chain reaction. J Microbiol Methods. 2000;39:97-107.

Sidky et al., Inhibition of murine tumor growth by an interferon-inducing imidazoquinolinamine. Cancer Res. Jul. 1, 1992;52(13):3528-33

Siegal et al., The nature of the principal type 1 interferon-producing cells in human blood. Science. Jun. 11, 1999;284(5421):1835-7.

Sletzinger ET al., The Synthesis of Isomethadone. J Am Chem Soc. 1952;74:5619-20.

Smith et al., The role of polymorphonuclear leukocytes in the lesion caused by the venom of the brown spider, *Loxosceles reclusa*. Lab Invest. Jan. 1970;22(1):90-3.

Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80-1933. 1980:76-8.

Sommer et al., Recent Findings on How Proinflammatory Cytokines Cause Pain: Peripheral Mechanisms in Inflammatory and Neuropathic Hyperalgesia. Neurosci Letts. 2004;361:184-87.

Sonogashira et al., A convenient synthesis of acetylenes: catalytic substitutions of acetylenic hydrogen with bromoalkenes, lodoarenes, and bromopyridines. Tetrahedron Letts. 1975;50:4467-4470.

Soria et al., C: Possibility of Predicting the Spectrum of Antitumor Effect of Drugs on the Basis of Experimental Data. Effect of food on the pharmacokinetics and bioavailability of oral imiquimod relative to a subcutaneous dose. Int J Clin Pharmacol Ther. Oct. 2000;38(10):476-81.

Spaner et al., A phase I/II trial of TLR-7 agonist immunotherapy in chronic lymphocytic leukemia. Leukemia. 2010; 24:222-26.

Spaner et al., Immunomodulatory effects of Toll-like receptor-7 activation on chronic lymphocytic leukemia cells. Leukemia. Feb. 2006;20(2):286-95.

Spaner et al., Toll-like receptor agonists in the treatment of chronic lymphocytic leukemia. Leukemia. Jan. 2007;21(1):53-60. Epub Oct. 26, 2006.

Spivey et al., Configurationally stable biaryl analogues of 4-(dimethylamino)pyridine: A novel class of chiral nucleophilic catalysts. J Org Chem. 1999;64:9430-9443.

Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.

Stack, Images in clinical medicine. *Latrodectus mactans*. N Engl J Med. Jun. 5, 1997;336(23):1649.

Stanley, Imiquimod and the imidazoquinolones: mechanism of action and therapeutic potential. Clin Exp Dermatol. Oct. 2002;27(7):571-7. Review.

Stashenko et al., Periapical inflammatory responses and their modulation. Crit Rev Oral Biol Med. 1998;9(4):498-521.

Steele et al., Lipoxygenase inhibitors as potential cancer chemopreventives. Cancer Epidemiol Biomarkers Prev. May 1999;8(5):467-83.

Steele et al., Potential use of lipoxygenase inhibitors for cancer chemoprevention. Expert Opin Investig Drugs. Sep. 2000;9(9):2121-38.

Steinmann et al., Topical imiquimod treatment of a cutaneous melanoma metastasis. J Am Acad Dermatol. Sep. 2000;43(3):555-6.

Stillings et al., Substituted 1,3,4-thiadiazoles with anticonvulsant activity. 2. Aminoalkyl derivatives. J Med Chem. Nov. 1986;29(11):2280-4.

Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.

Stringfellow, Induction of interferon with low molecular weight compounds: fluorenone esters, ethers (tilorone), and pyrimidinones. Methods Enzymol. 1981;78(Pt A):262-84.

Ströher et al., Progress towards the treatment of Ebola haemorrhagic fever. Expert Opin Investig Drugs. Dec. 2006;15(12):1523-35.

Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;S475:Abstract 3030.

Surrey et al., The Synthesis of Some 3-Nitro- and 3-Amino-4-dialkylaminoalkylaminoquinoline Derivatives. J Am Chem Soc. 1951;73:2413-16.

Takeichi et al., Cytokine profiles of T-lymphocytes from gingival tissues with pathological pocketing. J Dent Res. Aug. 2000;79(8):1548-55.

Takeshita et al., Signal transduction pathways mediated by the interaction of CpG DNA with Toll-like receptor 9. Semin Immunol. Feb. 2004;16(1):17-22.

Takeuchi et al., Discrimination of bacterial lipoproteins by Toll-like receptor 6. Int Immunol. Jul. 2001;13(7):933-40.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.

Thesing et al., [Darstellung und Eigenschaften des $\Delta^1$-Pyrrolin-$N$-oxyds.]. Chem Ber. 1959;92:1748-55. German.

Thiruvikraman et al., Synthesis and reactions of pyrazolo-[3,4-c]quinoline derivatives. Indian Journal of Chemistry. 1987;26B:695-696.

Tomai et al., Imiquimod: in vivo and in vitro characteristics and toxicology. In: Cutaneous Infection and Therapy. Aly et al., eds. Marcel Dekkar, Inc., New York. 1997:405-15.

Tomic et al., Sensitization of IL-2 Signaling through TLR-7 Enhances B Lymphoma Cell Immunogenicity. J Immunol. 2006;176:3830-39.

Tomioka et al., Asymmetric Alkylation of α-Alkyl β-Keto Esters. J Am Chem Soc. 1984;106:2718-19.

Totterman et al., Phorbol ester-induced differentiation of chronic lymphocytic leukaemia cells. Nature. Nov. 13, 1980;288(5787):176-8.

Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.

Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.

Urosevic et al., Imiquimod treatment induces expression of opioid growth factor receptor: a novel tumor antigen induced by interferon-alpha? Clin Cancer Res. Aug. 1, 2004;10(15):4959-70.

Van De Kerhof, New Immunomodulatory Drugs. In: Skin and Environment: Perception and Protection. Ring et al., eds., 10th EADV Congress, Oct. 10-14, Munich, Germany. 2001:1:343-48.

Vasilakos et al., Adjuvant Activities of Immune Response Modifier R-848: Comparison with CoG ODN. Cell Immunol. 2000;204:64-74.

Vieweg et al., Tumor vaccines: from gene therapy to dendritic cells—the emerging frontier. Urol Clin North Am. Aug. 2003;30(3):633-43.

Vilcek, The cytokines: An overview. In: The Cytokine Handbook, Fourth Ed. M. Lotze and A.W. Thompson (eds.), 2003;1:3-14.

Volhardt, 18-5. Amides: The Least-Reactive Carboxylic Acid Derivatives. Organic Chemistry. 1987:813.

Vollmer et al., Highly immunostimulatory CpG-free oligodeoxynucleotides for activation of human leukocytes. Antisense Nucleic Acid Drug Dev. Jun. 2002;12(3):165-75.

Wagner et al., Induction of cytokines in cynomolgus monkeys by the immune response modifiers, imiquimod, S-27609 and S-28463. Cytokine. Nov. 1997;9(11):837-45.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-92.

(56) References Cited

OTHER PUBLICATIONS

Warren et al., Macrophage Growth Factor CSF-1 Stimulates Human Monocyte Production of Interferon, Tumor Necrosis Factor, and Colony Stimulating Activity. J Immunol. 1986;137(7):2281-85.

Wasserman et al., Loxoscelism and necrotic arachnidism. J Toxicol Clin Toxicol. 1983-1984;21(4-5):451-72.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-17.

Wermuth, Molecular Variations Based on Isosteric Replacements. Practice of Medicinal Chemistry.1996:203-37.

Wexler et al., Accurate identification of experimental pulmonary metastases. J Natl Cancer Inst. Apr. 1966;36(4):641-5.

Wibaut et al., Syntheses of 3,4-Dimethylpyridine, 2,3-Dimethylpridine and 2-Methyl-3-Ethylpyridine. Rec Trav Chim. 1944;63:231-38.

Wierda et al., CD40-ligand (CD154) gene therapy for chronic lymphocytic leukemia. Blood. Nov. 1, 2000;96(9):2917-24.

Wieseler-Frank et al., Central proinflammatory cytokines and pain enhancement. Neurosignals. 2005;14(4):166-74.

Williams et al., Grignard Reactions to Chiral Oxazolidine Aldehydes. Tetrahedron. 1996;52:11673-94.

Wilson et al., Spiders and spider bites. Dermatol Clin. Apr. 1990;8(2):277-86.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002;15(2):115-22.

Yutilov et al., Synthesis and some reactions of 4-nitroimidazo[4-5-c]pyridin-2-ones. CAPLUS English Abstract DN 91:175261. VINITI.1978:1193-78. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zambon, Periodontal diseases: microbial factors. Ann Periodontol. Nov. 1996;1(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.

Zhang et al., Structural features of azidopyridinyl neonicotinoid probes conferring high affinity and selectivity for mammalian alpha4beta2 and Drosophila nicotinic receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J Leukoc Biol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

Dvorakova, "*Synthesis and Biological Effects of Acyclic Analogs of Deazapurine Nucleosides*" Collect. Czech. Chem. Commun. vol. 58, pp. 629-630,1993.

\* cited by examiner

SUBSTITUTED IMIDAZO RING SYSTEMS AND METHODS

CROSS-REFERENCE TO RELATED APPLICATIONS

This application is the National Stage of International Application No. PCT/US2004/039512, filed Nov. 24, 2004, which claims priority to U.S. Provisional Application Ser. No. 60/524961, filed on Nov. 25, 2003, and to U.S. Provisional Application Ser. No. 60/580139, filed on Jun. 16, 2004, both of which are incorporated by reference herein in their entirety.

BACKGROUND

In the 1950's the 1H-imidazo[4,5-c]quinoline ring system was developed and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers (IRMs), rendering them useful in the treatment of a variety of disorders.

There continues to be interest in the imidazoquinoline ring system, and other ring systems, and there is a continuing need for compounds that have the ability to modulate the immune response, by induction of cytokine biosynthesis or other mechanisms.

SUMMARY

The present invention provides a new class of compounds that are useful in inducing cytokine biosynthesis in animals. Such compounds are of the following Formula (I):

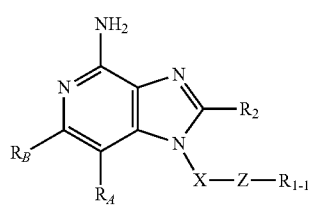

wherein: Z is —C(O)—, —C(O)O—, or —C(-Q-$R_{1-3}$)$_2$—; and
wherein: X, $R_A$, $R_B$, $R_2$, $R_{1-1}$, Q, and $R_{1-3}$ are as defined below.

The compounds of Formula I-1 are useful as immune response modifiers due to their ability to induce cytokine biosynthesis (e.g., induces the synthesis of at least one cytokine) and otherwise modulate the immune response when administered to animals. This makes the compounds useful in the treatment of a variety of conditions such as viral diseases and tumors that are responsive to such changes in the immune response.

The invention further provides pharmaceutical compositions containing an effective amount of a compound of Formula I-1 and methods of inducing cytokine biosynthesis in an animal, treating a viral infection and/or treating a neoplastic disease in an animal by administering an effective amount of a compound of Formula I-1 to the animal.

In addition, methods of synthesizing compounds of Formula I-1 and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formula (I-1):

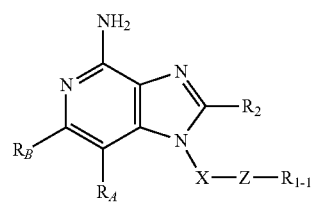

wherein: Z is —C(O)—, —C(O)O—, or —C(-Q-$R_{1-3}$)$_2$—;
and as well as more specific compounds of Formulas (I-2, I-3, and I-4), which represent different core ring structures:

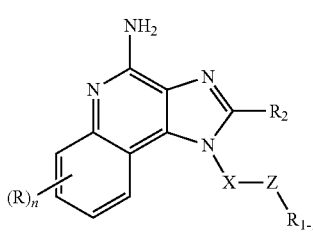

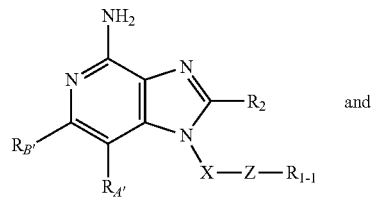

and

-continued

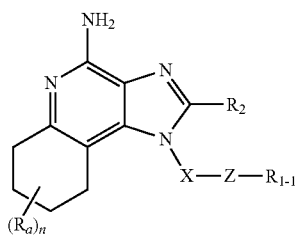
I-4 wherein: Z is —C(O)—, —C(O)O—, or —C(-Q-R$_{1-3}$)$_2$—;
and more specific compounds of the following Formulas (Ia, Ib, Id, and Ie):

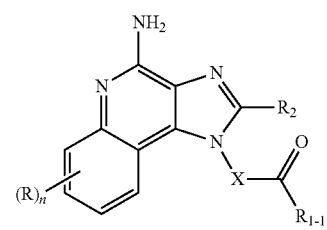
Ia

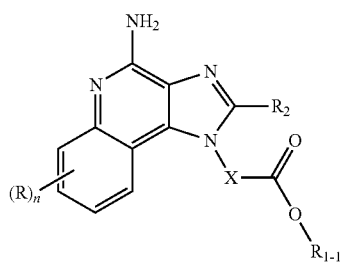
Ib

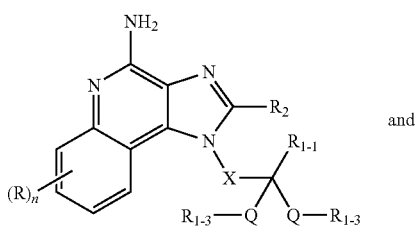
Id

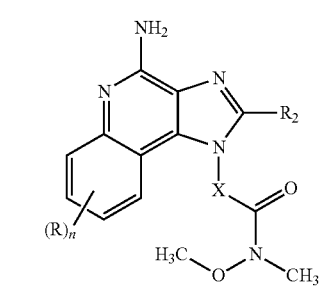
Ie wherein: X, R, R$_a$, R$_A$, R$_B$, R$_{A'}$, R$_{B'}$, R$_2$, R$_3$, R$_{1-1}$, Q, R$_{1-3}$, and n are as defined below;
and pharmaceutically acceptable salts thereof.

The present invention also provides compounds of the following Formulas (II, III, and IV):

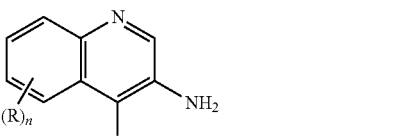
II wherein: Z is —C(O)—, —C(O)O—, or —C(-Q-R$_{1-3}$)$_2$—;

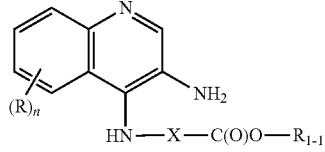
III and

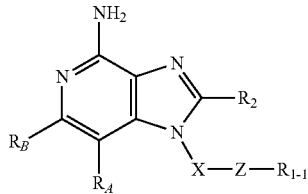
IV wherein: X, R, R$_2$, R$_{1-1}$, R$_{1-6}$, Q, R$_{1-3}$, and n are as defined below; and pharmaceutically acceptable salts thereof.

In one embodiment, there is provided a compound of the Formula (I-1):

I-1 wherein:
X is alkylene optionally interrupted by one or more —O— groups;
Z is —C(O)—, —C(O)O—, or —C(-Q-R$_{1-13}$)$_2$—;
R$_{1-1}$ is selected from the group consisting of:
hydrogen,
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, —NH—SO$_2$—R$_{1-4}$,
—NH—C(O)—R$_{1-4}$,
—NH—C(O)—NH$_2$,
—NH—C(O)—NH—R$_{1-4}$, and
—N$_3$;
with the proviso that if Z is —C(O)—, then R$_{1-1}$ may also be —N(CH$_3$)(OCH$_3$);
with the further proviso that if Z is —C(O)O—, then R$_{1-1}$ is not hydrogen;
with the further proviso that if Z is —C(O)O—, then X does not include —O— groups;
Q is O or S;
R$_{1-3}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—SO$_2$—R$_{1-4}$,
—NH—C(O)—R$_{1-4}$,
—NH—C(O)—NH$_2$,
—NH—C(O)—NH—R$_{1-4}$, and
—N$_3$;
or the R$_{1-3}$ groups can join together to form a ring system comprising a saturated or unsaturated 5-, 6-, or 7-membered ring;
R$_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—N$_3$; and
R$_2$ is selected from the group consisting of:
—R$_4$,
—X'—R$_4$,
—X'—Y'—R$_4$, and
—X'—R$_5$;
X' is selected from the group consisting of alkylene, alkenylene, alkynylene, arylene, and heteroarylene, wherein the alkylene, alkenylene, and alkynylene groups can be optionally interrupted or terminated with arylene, or heteroarylene, and optionally interrupted by one or more —O— groups;

Y' is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q'-,
—C(R$_6$)—N(R$_8$)—,
—O—C(R$_6$)—N(R$_8$)—,
—C(R$_6$)—N(OR$_9$)—,

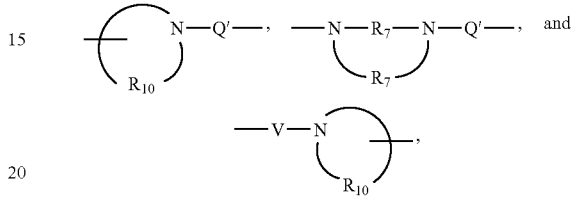

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, and alkynyl, oxo;
R$_5$ is selected from the group consisting of:

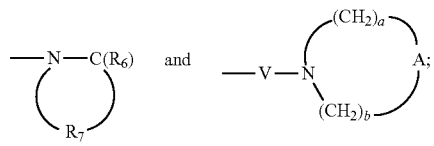

R$_6$ is selected from the group consisting of =O and =S;
R$_7$ is a C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, —CH$_2$—, and —N(R$_4$)—;
Q' is selected from the group consisting of a bond, —C(R$_6$)—, —C(R$_6$)—C(R$_6$)—, —S(O)$_2$—, and —S(O)$_2$—N(R$_8$)—;
V is selected from the group consisting of —C(R$_6$)—, —O—C(R$_6$)—, and —S(O)$_2$—;
a and b are independently integers from 1 to 6 with the proviso that a+b is ≤7;
R$_A$ and R$_B$ are each independently selected from the group consisting of:
hydrogen,
halogen,
alkyl, alkenyl,
alkoxy,
alkylthio, and
—N(R$_9$)$_2$;
or R$_A$ and R$_B$ taken together form either a fused aryl ring that is unsubstituted or substituted by one or more R groups, or a fused 5 to 7 membered saturated ring that is unsubstituted or substituted by one or more R$_a$ groups;
R is selected from the group consisting of:
fluoro,
alkyl,
haloalkyl,
alkoxy, and
—N(R$_9$)$_2$;
R$_a$ is selected from the group consisting of:
halogen,
hydroxy,
alkyl,
alkenyl,
haloalkyl,
alkoxy,
alkylthio, and
—N(R$_9$)$_2$;
or a pharmaceutically acceptable salt thereof In one embodiment, there is provided a compound of the Formula (I-2):

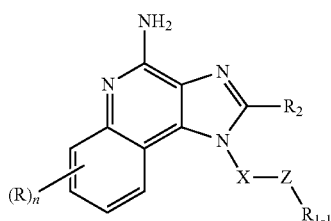

I-2 wherein:
X is alkylene optionally interrupted by one or more —O— groups;
n is an integer from 0 to 4;
Z is —C(O)—, —C(O)O—, or —C(-Q-R$_{1-3}$)$_2$—;
R$_{1-1}$ is selected from the group consisting of:
hydrogen,
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—SO$_2$—R$_{1-4}$,
—NH—C(O)—R$_{1-4}$,
—NH—C(O)—NH$_2$,
—NH—C(O)—NH—R$_{1-4}$, and
—N$_3$;
with the proviso that if Z is —C(O)—, then R$_{1-1}$ may also be —N(CH$_3$)(OCH$_3$);
with the further proviso that if Z is —C(O)O—, then R$_{1-1}$ is not hydrogen;
with the further proviso that if Z is —C(O)O—, then X does not include —O— groups;
Q is O or S;
R$_{1-3}$ is selected from the group consisting of:
alkyl,
aryl,
alkylene-aryl,
heteroaryl,
alkylene-heteroaryl; and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—SO$_2$—R$_{1-4}$,
—NH—C(O)—R$_{1-4}$,
—NH—C(O)—NH$_2$,
—NH—C(O)—NH—R$_{1-4}$, and
—N$_3$;
or the R$_{1-3}$ groups can join together to form a ring system comprising a saturated or unsaturated 5-, 6-, or 7-membered ring;
R$_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—N$_3$; and
R is selected from the group consisting of:
fluoro,
alkyl,
haloalkyl,
alkoxy, and
—N(R$_9$)$_2$;
R$_2$ is selected from the group consisting of:
—R$_4$,
—X'—R$_4$,
—X'—Y'—R$_4$, and
—X'—R$_5$;
X' is selected from the group consisting of alkylene, alkenylene, alkynylene, arylene, and heteroarylene, wherein the alkylene, alkenylene, and alkynylene groups can be optionally interrupted or terminated with arylene, or heteroarylene, and optionally interrupted by one or more —O— groups;

Y' is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q'-,
—C(R$_6$)—N(R$_8$)—,
—O—C(R$_6$)—N(R$_8$)—,
—C(R$_6$)—N(OR$_9$)—,

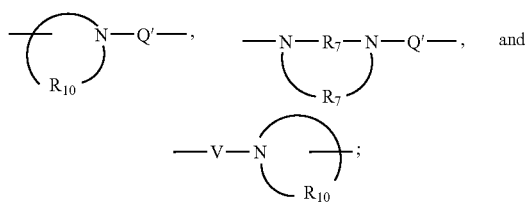

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, and alkynyl, oxo;

R$_5$ is selected from the group consisting of:

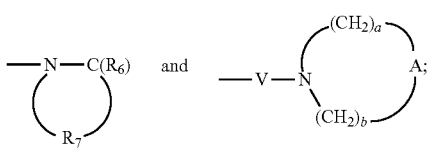

R$_6$ is selected from the group consisting of =O and =S;
R$_7$ is a C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, —CH$_2$—, and —N(R$_4$)—;
Q' is selected from the group consisting of a bond, —C(R$_6$)—, —C(R$_6$)—C(R$_6$)—, —S(O)$_2$—, and —S(O)$_2$—N(R$_8$);
V is selected from the group consisting of —C(R$_6$)—, —O—C(R$_6$)—, —N(R$_8$)—C(R$_6$)—, and —S(O)$_2$—; and
a and b are independently integers from 1 to 6 with the proviso that a+b is ≤7;
or a pharmaceutically acceptable salt thereof.

In another embodiment, there is provided a compound of the Formula (I-3):

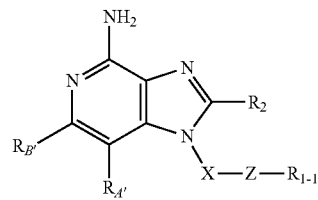

wherein:
X is alkylene optionally interrupted by one or more —O— groups;
Z is —C(O)—, —C(O)O—, or —C(-Q-R$_{1-3}$)$_2$—;
R$_{1-1}$ is selected from the group consisting of:
hydrogen,
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—SO$_2$—R$_{1-4}$,
—NH—C(O)—R$_{1-4}$,
—NH—C(O)—NH$_2$,
—NH—C(O)—NH—R$_{1-4}$, and
—N$_3$;
with the proviso that if Z is —C(O)—, then R$_{1-1}$ may also be —N(CH$_3$)(OCH$_3$);
with the further proviso that if Z is —C(O)O—, then R$_{1-1}$ is not hydrogen;
with the further proviso that if Z is —C(O)O—, then X does not include —O— groups;
Q is O or S;
R$_{1-3}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—SO$_2$—R$_{1-4}$,
—NH—C(O)—R$_{1-4}$,
—NH—C(O)—NH$_2$, —NH—C(O)—NH—R$_{1-4}$, and
—N$_3$;
or the R$_{1-3}$ groups can join together to form a ring system comprising a saturated or unsaturated 5-, 6-, or 7-membered ring;
R$_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—N$_3$; and
R$_2$ is selected from the group consisting of:
—R$_4$,
—X'—R$_4$,
—X'—Y'—R$_4$, and
—X'—R$_5$;
X' is selected from the group consisting of alkylene, alkenylene, alkynylene, arylene, and heteroarylene, wherein the alkylene, alkenylene, and alkynylene groups can be optionally interrupted or terminated with arylene, or heteroarylene, and optionally interrupted by one or more —O— groups;
Y' is selected from the group consisting of:
—S(O)$_{0-2}$—,
—S(O)$_2$—N(R$_8$)—,
—C(R)—,
—C(R)—O—,
—O—C(R)—,
—O—C(O)—O—,
—N(R$_8$)-Q'-,
—C(R$_6$)—N(R$_8$)—,
—O—C(R$_6$)—N(R$_8$)—,
—C(R$_6$)—N(OR$_9$)—,

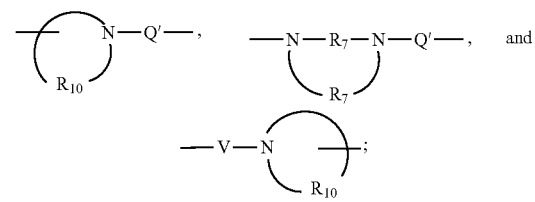

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, and alkynyl, oxo;
R$_5$ is selected from the group consisting of:

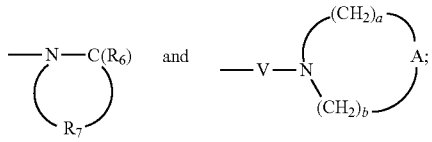

R$_6$ is selected from the group consisting of =O and =S;
R$_7$ is a C$_{2-7}$ alkylene;
R$_8$ is selected from the group consisting of hydrogen, alkyl, alkoxyalkylenyl, and arylalkylenyl;
R$_9$ is selected from the group consisting of hydrogen and alkyl;
R$_{10}$ is C$_{3-8}$ alkylene;
A is selected from the group consisting of —O—, —C(O)—, —S(O)$_{0-2}$—, —CH$_2$—, and —N(R$_4$)—;
Q' is selected from the group consisting of a bond, —C(R$_6$)—, —C(R$_6$)—C(R$_6$)—, —S(O)$_2$—, and —S(O)$_2$—N(R$_8$)—;
V is selected from the group consisting of —C(R$_6$)—, —O—C(R$_6$)—, and —S(O)$_2$—;
a and b are independently integers from 1 to 6 with the proviso that a+b is ≤7;
R$_{A'}$ and R$_{B'}$ are each independently selected from the group consisting of:
hydrogen,
halogen,
alkyl,
alkenyl,
alkoxy,
alkylthio, and
—N(R$_9$)$_2$;
or a pharmaceutically acceptable salt thereof.
In another embodiment, there is provided a compound of the Formula (I-4):

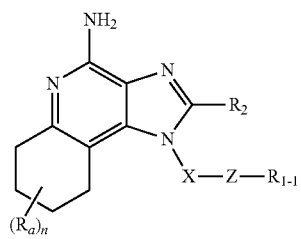

wherein:
X is alkylene optionally interrupted by one or more —O— groups;
n is an integer from 0 to 4;
Z is —C(O)—, —C(O)O—, or —C(-Q-R$_{1-3}$)$_2$—;
R$_{1-1}$ is selected from the group consisting of:
hydrogen,
alkyl,
aryl,
alkylene-aryl,
heteroaryl,
alkylene-heteroaryl, and alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—SO$_2$—R$_{1-4}$,
—NH—C(O)—R$_{1-4}$,
—NH—C(O)—NH$_2$,
—NH—C(O)—NH—R$_{1-4}$, and
—N$_3$;
with the proviso that if Z is —C(O)—, then R$_{1-1}$ may also be —N(CH$_3$)(OCH$_3$);
with the further proviso that if Z is —C(O)O—, then R$_{1-1}$ is not hydrogen;
with the further proviso that if Z is —C(O)O—, then X does not include —O— groups;
Q is O or S;
R$_{1-3}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—SO$_2$—R$_{1-4}$,
—NH—C(O)—R$_{1-4}$,
—NH—C(O)—NH$_2$,
—NH—C(O)—NH—R$_{1-4}$, and
—N$_3$;
or the R$_{1-3}$ groups can join together to form a ring system comprising a saturated or unsaturated 5-, 6-, or 7-membered ring;
R$_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy, alkyl, and
—N$_3$; and
R$_a$ is selected from the group consisting of:
halogen,
hydroxy,
alkyl,
alkenyl,
haloalkyl,
alkoxy,
alkylthio, and
—N(R$_9$)$_2$;
R$_2$ is selected from the group consisting of:
—R$_4$,
—X'—R$_4$,
—X'—Y'—R$_4$, and
—X'—R$_5$;
X' is selected from the group consisting of alkylene, alkenylene, alkynylene, arylene, and heteroarylene, wherein the alkylene, alkenylene, and alkynylene groups can be optionally interrupted or terminated with arylene, or heteroarylene, and optionally interrupted by one or more —O— groups;
Y' is selected from the group consisting of:
—S(O)$_{0-2}$—,
—S(O)$_2$—N(R$_8$)—,
—C(R$_6$)—,
—C(R$_6$)—O—,
—O—C(R$_6$)—,
—O—C(O)—O—,
—N(R$_8$)-Q'-,
—C(R$_6$)—N(R$_8$)—,
—O—C(R$_6$)—N(R$_8$)—,
—C(R$_6$)—N(OR$_9$)—,

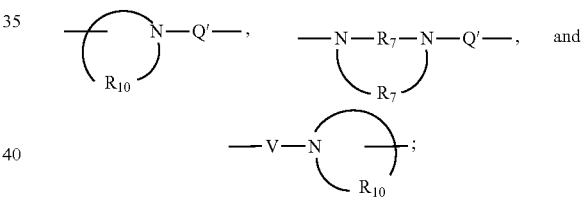

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, and alkynyl, oxo;
R$_5$ is selected from the group consisting of:

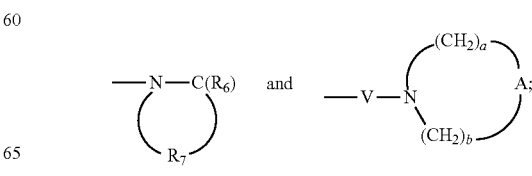

R₆ is selected from the group consisting of =O and =S;
R₇ is a $C_{2-7}$ alkylene;
R is selected from the group consisting of hydrogen, alkyl, alkoxyalkylenyl, and arylalkylenyl;
R₉ is selected from the group consisting of hydrogen and alkyl;
R₁₀ is $C_{3-8}$ alkylene;
A is selected from the group consisting of —O—, —C(O)—, —S(O)₀₋₂—, —CH₂—, and —N(R₄)—;
Q' is selected from the group consisting of a bond, —C(R₆)—, —C(R₆)—C(R₆)—, —S(O)₂—, and —S(O)₂—N(R₈)—;
V is selected from the group consisting of —C(R₆)—, —O—C(R₆)—, and —S(O)₂—; and
a and b are independently integers from 1 to 6 with the proviso that a +b is ≤7;
or a pharmaceutically acceptable salt thereof. P In another embodiment, there is provided a compound of the Formula (Ia):

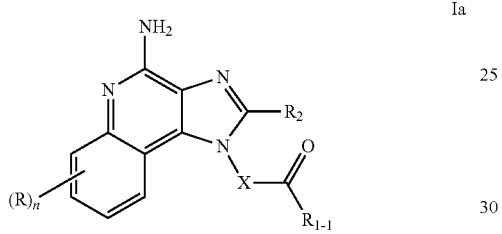

Ia wherein:
X is alkylene optionally interrupted by one or more —O— groups;
n is an integer from 0 to 4;
$R_{1-1}$ is selected from the group consisting of:
hydrogen,
alkyl,
aryl,
alkylene-aryl,
heteroaryl,
alkylene-heteroaryl,
—N(CH₃)(OCH₃), and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—SO₂—$R_{1-4}$,
—NH—C(O)—$R_{1-4}$,
—NH—C(O)—NH₂,
—NH—C(O)—NH—$R_{1-4}$, and
—N₃;
$R_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—N₃;
R is selected from the group consisting of:
fluoro,
alkyl,
haloalkyl,
alkoxy, and
N(R₉)₂; and
R₂ is selected from the group consisting of:
hydrogen,
alkyl,
alkenyl,
aryl,
heteroaryl,
heterocyclyl,
alkylene-Y-alkyl,
alkylene-Y-alkenyl, alkylene-Y-aryl, and
alkyl or alkenyl substituted by one or more substituents selected from the group consisting of:
hydroxy,
halogen,
—N(R₃)₂,
—C(O)—$C_{1-10}$alkyl,
—C(O)—O—$C_{1-10}$alkyl,
—N(R₃)—C(O)—$C_{1-10}$alkyl,
—N₃,
aryl,
heteroaryl,
heterocyclyl,
—C(O)-aryl, and
—C(O)-heteroaryl;
wherein:
Y is —O— or —S(O)₀₋₂—; and
R₃ is selected from the group consisting of:
hydrogen,
$C_{1-10}$alkyl, and
$C_{2-10}$alkenyl, and
R₉ is selected from the group consisting of hydrogen and alkyl; or a pharmaceutically acceptable salt thereof.
In another embodiment, there is provided a compound of the Formula (Ib):

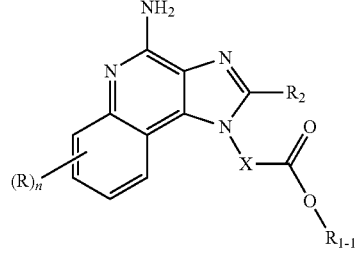

Ib wherein:
X is alkylene;
n is an integer from 0 to 4;
R$_{1-1}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—S)$_2$—R$_{1-4}$,
—NH—C(O)—R$_{1-4}$,
—NH—C(O)—NH$_2$,
—NH—C(O)—NH—R$_{1-4}$, and
—N$_3$;
R$_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—N$_3$;
R is selected from the group consisting of:
fluoro,
alkyl,
alkoxy,
haloalkyl, and
—N(R$_9$)$_2$, and
R$_2$ is selected from the group consisting of:
hydrogen,
alkyl,
alkenyl,
aryl,
heteroaryl,
heterocyclyl,
alkylene-Y-alkyl,
alkylene-Y-alkenyl,
alkylene-Y-aryl, and
alkyl or alkenyl substituted by one or more substituents selected from the group consisting of:
hydroxy,
halogen,
—N(R$_3$)$_2$,
—C(O)—C$_{1-10}$alkyl,
—C(O)—O—C$_{1-10}$alkyl,
—N(R$_3$)—C(O)—C$_{1-10}$alkyl,
—N$_3$,
aryl,
heteroaryl,
heterocyclyl,
—C(O)-aryl, and
—C(O)-heteroaryl;
wherein:
Y is —O— or —S(O)$_{0-2}$—; and
R$_3$ is selected from the group consisting of:
hydrogen,
C$_{1-10}$alkyl, and
C$_{2-10}$alkenyl; and
R$_9$ is selected from the group consisting of hydrogen and alkyl; or a pharmaceutically acceptable salt thereof.
In another embodiment, the present invention provides a compound of the Formula (Id):

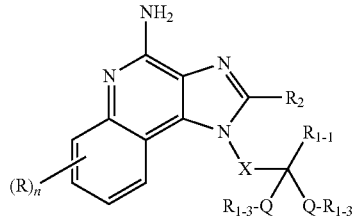

wherein:
X is alkylene optionally interrupted by one or more —O— groups;
n is an integer from 0 to 4;
R$_{1-1}$ is selected from the group consisting of:
hydrogen,
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—S)$_2$—R$_{1-4}$,
—NH—C(O)—R$_{1-4}$,
—NH—C(O)—NH$_2$,
—NH—C(O)—NH—R$_{1-4}$, and
—N$_3$;
Q is O or S;
R$_{1-3}$ is selected from the group consisting of:
alkyl,
aryl,
alkylene-aryl,
heteroaryl,
alkylene-heteroaryl, and alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—SO$_2$—R$_{1-4}$,
—NH—C(O)—R$_{1-4}$,
—NH—C(O)—NH$_2$,
—NH—C(O)—NH—R$_{1-4}$, and
—N$_3$;
or the R$_{1-3}$ groups can join together to form a ring system comprising a saturated or unsaturated 5-, 6-, or 7-membered ring;
R$_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—N$_3$;
R is selected from the group consisting of:
fluoro,
alkyl,
alkoxy,
haloalkyl, and
—N(R$_9$)$_2$, and
R$_2$ is selected from the group consisting of:
hydrogen,
alkyl,
alkenyl,
aryl,
heteroaryl,
heterocyclyl,
alkylene-Y-alkyl,
alkylene-Y-alkenyl,
alkylene-Y-aryl, and
alkyl or alkenyl substituted by one or more substituents selected from the group consisting of:
hydroxy,
halogen,
—N(R$_3$)$_2$,
—C(O)—C$_{1-10}$alkyl,
—C(O)—O—C$_{1-10}$alkyl,
—N(R$_3$)—C(O)—C$_{1-10}$alkyl,
—N$_3$,
aryl,
heteroaryl,
heterocyclyl, —C(O)-aryl, and
—C(O)-heteroaryl;
wherein:
Y is —O— or —S(O)$_{0-2}$—; and
R$_3$ is selected from the group consisting of:
hydrogen,
C$_{1-10}$alkyl, and
C$_{2-10}$alkenyl; and
R$_9$ is selected from the group consisting of hydrogen and alkyl; or a pharmaceutically acceptable salt thereof In another embodiment, there is provided a compound of the Formula (Ie):

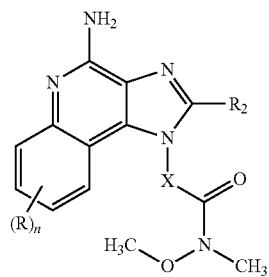

wherein:
X is alkylene optionally interrupted by one or more —O— groups;
n is an integer from 0 to 4;
R is selected from the group consisting of:
fluoro,
alkyl,
alkoxy,
haloalkyl, and
—N(R$_9$)$_2$, and
R$_2$ is selected from the group consisting of:
hydrogen,
alkyl,
alkenyl,
aryl,
heteroaryl,
heterocyclyl,
alkylene-Y-alkyl,
alkylene-Y-alkenyl,
alkylene-Y-aryl, and
alkyl or alkenyl substituted by one or more substituents selected from the group consisting of:
hydroxy,
halogen,
—N(R$_3$)$_2$,
—C(O)—C$_{1-10}$alkyl,
—C(O)—O—C$_{1-10}$alkyl,
—N(R$_3$)—C(O)—C$_{1-10}$alkyl,
—N$_3$,
aryl,
heteroaryl,
heterocyclyl,
—C(O)-aryl, and
—C(O)-heteroaryl;
wherein:
Y is —O— or —S(O)$_{0-2}$—; and
R$_3$ is selected from the group consisting of:
hydrogen,
C$_{1-10}$alkyl, and
C$_{2-10}$alkenyl; and $R_3$ is selected from the group consisting of hydrogen and alkyl; or a pharmaceutically acceptable salt thereof.

In another embodiment, there is provided a compound of the Formula (II):

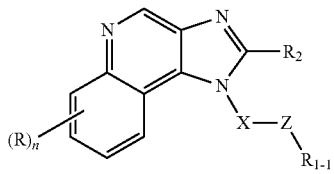

wherein:

X is alkylene optionally interrupted by one or more —O— groups;

n is an integer from 0 to 4;

Z is —C(O)—, —C(O)O—, or —C(-Q-$R_{1-3}$)$_2$—;

$R_{1-1}$ is selected from the group consisting of:
hydrogen,
alkyl,
aryl,
alkylene-aryl,
heteroaryl,
alkylene-heteroaryl, and
alkyl aryl, alkylene-aryl, heteroaryl, or alkylene-heteroaryl substituted by one or more substituents selected from the group consisting of:
  halogen,
  cyano,
  nitro,
  alkoxy,
  dialkylamino,
  alkylthio,
  haloalkyl,
  haloalkoxy,
  alkyl,
  —NH—SO$_2$—$R_{1-4}$,
  —NH—C(O)—$R_{1-4}$,
  —NH—C(O)—NH$_2$,
  —NH—C(O)—NH—$R_{1-4}$, and
  —N$_3$;
with the proviso that if Z is —C(O)—, then $R_{1-1}$ may also be —N(CH$_3$)(OCH$_3$);
with the further proviso that if Z is —C(O)O—, then $R_{1-1}$ is not hydrogen;
with the further proviso that if Z is —C(O)O—, then X does not include —O— groups;

Q is O or S;

$R_{1-3}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
  halogen,
  cyano,
  nitro,
  alkoxy,
  dialkylamino,
  alkylthio,
  haloalkyl,
  haloalkoxy,
  alkyl,
  —NH—SO$_2$—$R_{1-4}$,
  —NH—C(O)—$R_{1-4}$,
  —NH—C(O)—NH$_2$,
  —NH—C(O)—NH—$R_{1-4}$, and
  —N$_3$;
or the $R_{1-3}$ groups can join together to form a ring system comprising a saturated or unsaturated 5-, 6-, or 7-membered ring;

$R_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
  halogen,
  cyano,
  nitro,
  alkoxy,
  dialkylamino,
  alkylthio,
  haloalkyl,
  haloalkoxy,
  alkyl, and
  —N$_3$;

R is selected from the group consisting of:
fluoro,
alkyl,
alkoxy,
haloalkyl, and
—N($R_9$)$_2$;

$R_2$ is selected from the group consisting of:
hydrogen,
alkyl,
alkenyl,
aryl,
heteroaryl,
heterocyclyl,
alkylene-Y-alkyl,
alkylene-Y-alkenyl,
alkylene-Y-aryl, and
alkyl or alkenyl substituted by one or more substituents selected from the group consisting of:
  hydroxy,
  halogen,
  —N($R_3$)$_2$,
  —C(O)—C$_{1-10}$alkyl,
  —C(O)—O—C$_{1-10}$alkyl,
  —N($R_3$)—C(O)—C$_{1-10}$alkyl,
  —N$_3$,
  aryl,
  heteroaryl,
  heterocyclyl,
  —C(O)-aryl, and
  —C(O)-heteroaryl;
wherein:
Y is —O— or —S(O)$_{0-2}$—; and
$R_3$ is selected from the group consisting of:
  hydrogen,
  C$_{1-10}$alkyl, and
  C$_{2-10}$alkenyl, and
$R_9$ is selected from the group consisting of hydrogen and alkyl; or a pharmaceutically acceptable salt thereof.

In another embodiment, there is provided a compound of the Formula (III):

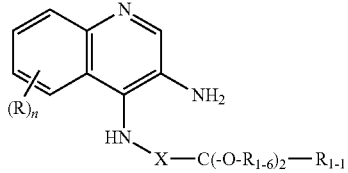

III wherein:
X is alkylene optionally interrupted by one or more —O— groups;
n is an integer from 0 to 4;
$R_{1-1}$ is selected from the group consisting of:
hydrogen,
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—$SO_2$—$R_{1-4}$,
—NH—C(O)—$R_{1-4}$,
—NH—C(O)—$NH_2$,
—NH—C(O)—NH—$R_{1-4}$, and
—$N_3$;
$R_{1-6}$ is alkyl or the $R_{1-6}$ groups can join together to form a ring system comprising a saturated 5- or 6-membered ring;
$R_{1-6}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—$N_3$;
R is selected from the group consisting of:
fluoro,
alkyl,
alkoxy,
haloalkyl, and
—$N(R_9)_2$; and
$R_9$ is selected from the group consisting of hydrogen and alkyl; or a pharmaceutically acceptable salt thereof.

In another embodiment, there is provided a compound of the Formula (IV):

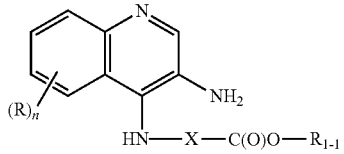

IV wherein:
X is alkylene;
n is an integer from 0 to 4;
$R_{1-1}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl,
—NH—$SO_2$—$R_{1-4}$,
—NH—C(O)—$R_{1-4}$,
—NH—C(O)—$NH_2$,
—NH—C(O)—NH—$R_{1-4}$, and
—$N_3$;
$R_{1-4}$ is selected from the group consisting of:
alkyl,
aryl,
alkylene-aryl,
heteroaryl,
alkylene-heteroaryl, and
alkyl, aryl, alkylene-aryl, heteroaryl, or alkylene-heteroaryl substituted by one or more substituents selected from the group consisting of:
halogen,
cyano,
nitro,
alkoxy,
dialkylamino,
alkylthio,
haloalkyl,
haloalkoxy,
alkyl, and
—$N_3$;
R is selected from the group consisting of:
fluoro,
alkyl,
alkoxy,
haloalkyl, and
—$N(R_9)_2$; and $R_9$ is selected from the group consisting of hydrogen and alkyl; or a pharmaceutically acceptable salt thereof.

As used herein, the terms "alkyl," "alkenyl," "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornyl.

Unless otherwise specified, "alkylene," "alkenylene," and "alkynylene" are the divalent forms of the "alkyl," "alkenyl," and "alkynyl" groups defined above. The terms, "alkylenyl," "alkenylenyl," and "alkynylenyl" are use when "alkylene," "alkenylene," and "alkynylene," respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl (azepanyl), homopiperazinyl (diazepanyl), 1,3-dioxolanyl, aziridinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, and the like. When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. The terms, "arylenyl," "heteroarylenyl," and "heterocyclylenyl" are used when "arylene," "heteroarylene," and "heterocyclylene," respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —$N(R_3)_2$ each $R_3$ group is independently selected. In a further example, when more than one $R_{1-3}$ group is present and each $R_{1-3}$ group contains one or more $R_{1-4}$ groups, then each $R_{1-3}$ group is independently selected, and each $R_{1-4}$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

For any of the compounds presented herein, each one of the following variables (e.g., Z, X, Y, Y', $R_4$, $R_B$, $R_2$, $R_{1-1}$, Q, $R_{1-3}$, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, A is selected from the group consisting of —O—, —C(O)—, —S(O)$_{0-2}$—, —$CH_2$—, and —$N(R_4)$—.

For certain embodiments, Q is —O— or —S—. For certain embodiments, Q is —O—.

For certain embodiments, Q' is selected from the group consisting of a bond, —$C(R_6)$—, —$C(R_6)$—$C(R_6)$—, —$S(O)_2$—, and —$S(O)_2$—$N(R_8)$—.

For certain embodiments, V is selected from the group consisting of —$C(R_6)$—, —O—$C(R_6)$—, and —$S(O)_2$—.

For certain embodiments, X is alkylene optionally interrupted by one or more —O— groups. For certain embodiments, X is a $C_{1-6}$ alkylene or —$(CH_2)_{2-4}$—O—$(CH_2)_{1-3}$—. For certain embodiments, X is alkylene. For certain embodiments, X is selected from the group consisting of —$(CH_2)_{1-6}$—, —$CH_2$—$C(CH_3)_2$—, —$(CH_2)_2$—O—$CH_2$—, —$(CH_2)_3$—O—$CH_2$—, and —$CH_2$—$C(CH_3)_2$—. For certain embodiments, X is selected from the group consisting of —$CH_2$—, —$(CH_2)_2$—, —$(CH_2)_3$—, —$(CH_2)_4$—, —$(CH_2)_5$—, —$(CH_2)_6$—, —$CH_2C(CH_3)_2$—, —$CH_2C(CH_3)_2CH_2$—, and —$(CH_2)_2OCH_2$—.

For certain embodiments, X' is selected from the group consisting of alkylene, alkenylene, alkynylene, arylene, and heteroarylene, wherein the alkylene, alkenylene, and alkynylene groups can be optionally interrupted or terminated with arylene, or heteroarylene, and optionally interrupted by one or more —O— groups.

For certain embodiments, Y is —O— or —$S(O)_{0-2}$—.

For certain embodiments, Y' is selected from the group consisting of —$S(O)_{0-2}$—, —$S(O)_2$—$N(R_8)$—, —$C(R_6)$—, —$C(R_6)$—O—, —O—$C(R_6)$—, —O—C(O)—O—, —$N(R_8)$-Q'-, —$C(R_6)$—$N(R_8)$—, —O—$C(R_6)$—$N(R_8)$—, —$C(R_6)$—$N(OR_9)$—,

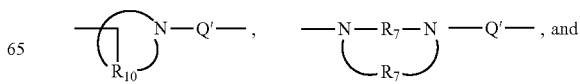

-continued

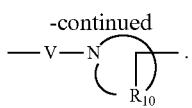

For certain embodiments, Z is —C(O)—, —C(O)O—, or —C(-Q-$R_{1-3}$)$_2$—. For certain embodiments, Z is —C(O)—. For certain embodiments, Z is —C(O)O—. For certain embodiments, Z is —C(-Q-$R_{1-3}$)$_2$—.

For certain embodiments, R is selected from the group consisting of fluoro, alkyl, alkoxy, haloalkyl, and —N($R_9$)$_2$. In certain of these embodiments, $R_9$ is selected from the group consisting of hydrogen and alkyl.

For certain embodiments, $R_A$ and $R_B$ are each independently selected from the group consisting of: hydrogen, halogen, alkyl, alkenyl, alkoxy, alkylthio, and —N($R_9$)$_2$. For certain embodiments, $R_A$ and $R_B$ are each independently selected from the group consisting of hydrogen and alkyl. For certain embodiments, $R_A$ and $R_B$ are both methyl.

For certain alternative embodiments, $R_A$ and $R_B$ form a fused aryl ring that is unsubstituted or substituted by one or more R groups.

For certain alternative embodiments, $R_A$ and $R_B$ form a fused 5 to 7 membered saturated ring, which is unsubstituted or substituted by one or more $R_a$ groups.

For certain embodiments, $R_a$ is selected from the group consisting of halogen, hydroxy, alkyl, alkenyl, haloalkyl, alkoxy, alkylthio, and —N($R_9$)$_2$.

For certain embodiments, $R_{A'}$ and $R_{B'}$ are each independently selected from the group consisting of: hydrogen, halogen, alkyl, alkenyl, alkoxy, alkylthio, and —N($R_9$)$_2$. For certain embodiments, $R_{A'}$ and $R_{B'}$ are independently selected from the group consisting of hydrogen and alkyl. For certain embodiments, $R_{A'}$ and $R_{B'}$ are both methyl.

For certain embodiments, $R_{1-1}$ is selected from the group consisting of hydrogen, alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of halogen, cyano, nitro, alkoxy, dialkylamino, alkylthio, haloalkyl, haloalkoxy, alkyl, —NH—$SO_2$—$R_{1-4}$, —NH—C(O)—$R_{1-4}$, —NH—C(O)—$NH_2$, —NH—C(O)—NH—$R_{1-4}$, and —$N_3$.

For certain embodiments, $R_{1-1}$ is selected from the group consisting of aryl, alkyl, and —N(CH$_3$)OCH$_3$. For certain embodiments, $R_{1-1}$ is selected from the group consisting of aryl, alkyl, and hydrogen. For certain embodiments, $R_{1-1}$ is selected from the group consisting of alkyl and aryl. For certain embodiments, $R_{1-1}$ is selected from the group consisting of methyl, ethyl, n-propyl, isopropyl, cyclopropyl, n-butyl, sec-butyl, isobutyl, tert-butyl, n-pentyl, cyclopentyl, n-hexyl, cyclohexyl, phenyl, 4-chlorophenyl and 2,4-dichlorophenyl.

For certain embodiments, $R_{1-3}$ is selected from the group consisting of alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of halogen, cyano, nitro, alkoxy, dialkylamino, alkylthio, haloalkyl, haloalkoxy, alkyl, —NH—$SO_2$—$R_{1-4}$, —NH—C(O)—$R_{1-4}$, —NH—C(O)—$NH_2$, —NH—C(O)—NH—$R_{1-4}$, and —$N_3$. For certain embodiments, the $R_{1-3}$ groups can join together to form a ring system. The ring system includes a 5-, 6-, or 7-membered ring. One of skill in the art would understand that the size and components of the ring system are not limiting as long as they do not destroy the immunomodulator activity of the compound (i.e., it is non-interfering). Typically, this means that the 5-, 6-, or 7-membered ring is unsubstituted or is optionally fused to one or two saturated or unsaturated 5-, 6-, or 7-membered rings or is substituted by one or more substituents selected from the group consisting of aryl, heteroaryl, halogen, haloalkyl, alkylene-O-alkyl, and substituted aryl. For certain embodiments, $R_{1-3}$ is alkyl, or the $R_{1-3}$ groups join to form a 5-membered ring.

For certain embodiments, $R_{1-4}$ is selected from the group consisting of alkyl, aryl, alkylene-aryl, heteroaryl, alkylene-heteroaryl, and alkyl, aryl, alkylene-aryl, heteroaryl, or alkylene-heteroaryl substituted by one or more substituents selected from the group consisting of halogen, cyano, nitro, alkoxy, dialkylamino, alkylthio, haloalkyl, haloalkoxy, alkyl, and —$N_3$.

For certain embodiments, $R_{1-6}$ is alkyl or the $R_{1-6}$ groups can join together to form a ring system comprising a saturated 5- or 6-membered ring.

For certain embodiments, $R_2$ is selected from the group consisting of hydrogen, alkyl, alkenyl, aryl, heteroaryl, heterocyclyl, alkylene-Y-alkyl, alkylene-Y-alkenyl, alkylene-Y-aryl, and alkyl or alkenyl substituted by one or more substituents selected from the group consisting of hydroxy, halogen, —N($R_3$)$_2$, —C(O)—$C_{1-10}$alkyl, —C(O)—O—$C_{1-10}$alkyl, —N($R_3$)—C(O)—$C_{1-10}$alkyl, —$N_3$, aryl, heteroaryl, heterocyclyl, —C(O)-aryl, and —C(O)-heteroaryl. In certain of these embodiments, Y is —O— or —S(O)$_{0-2}$—; and $R_3$ is selected from the group consisting of hydrogen, $C_{1-10}$alkyl, and $C_{2-10}$alkenyl.

For certain embodiments, $R_2$ is selected from the group consisting of hydrogen, alkyl, hydroxyalkyl, and alkoxyalkyl. For certain embodiments, $R_2$ is selected from the group consisting of hydrogen, alkyl, and alkoxyalkyl. For certain embodiments, $R_2$ is selected from the group consisting of hydrogen, hydroxymethyl, methyl, ethyl, n-propyl, n-butyl, ethoxymethyl, and 2-methoxyethyl.

For certain embodiments, particularly embodiments of Formula I-1, $R_2$ is selected from the group consisting of: —$R_4$, —X'—$R_4$, —X'—Y'—$R_4$, and —X'—$R_5$.

For certain embodiments, $R_3$ is selected from the group consisting of hydrogen, $C_{1-10}$alkyl, and $C_{2-10}$alkenyl.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl, wherein the alkyl, alkenyl, alkynyl, aryl, arylalkylenyl, aryloxyalkylenyl, alkylarylenyl, heteroaryl, heteroarylalkylenyl, heteroaryloxyalkylenyl, and alkylheteroarylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, and alkynyl, oxo.

For certain embodiments, $R_4$ is alkyl which may be unsubstituted or substituted by hydroxy or alkoxy.

For certain embodiments, $R_5$ is selected from the group consisting of:

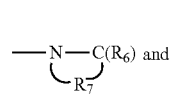 and 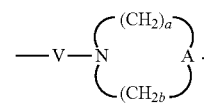

For certain embodiments, $R_6$ is selected from the group consisting of =O and =S.

For certain embodiments, $R_7$ is a $C_{2-7}$ alkylene.

For certain embodiments, $R_8$ is selected from the group consisting of hydrogen, alkyl, alkoxyalkylenyl, and arylalkylenyl. For certain embodiments, $R_8$ is H or $CH_3$.

For certain embodiments, $R_9$ is selected from the group consisting of hydrogen and alkyl.

For certain embodiments, $R_{10}$ is $C_{3-8}$ alkylene.

For certain embodiments, a and b are independently integers from 1 to 6 with the proviso that a+b is ≤7.

For certain embodiments, n is an integer from 0 to 4. For certain embodiments, n is 0.

For certain embodiments, particularly embodiments of Formula (I-1): if Z is —C(O)—, then $R_{1-1}$ may also be —N(CH$_3$)(OCH$_3$); if Z is —C(O)O—, then $R_{1-1}$ is not hydrogen; and if Z is —C(O)O—, then X does not include —O— groups.

For certain embodiments, particularly embodiments of Formula (I-2): if Z is —C(O)—, then $R_{1-1}$ may also be —N(CH$_3$)(OCH$_3$); if Z is —C(O)O—, then $R_{1-1}$ is not hydrogen; and if Z is —C(O)O—, then X does not include —O— groups. wherein:

For certain embodiments, particularly embodiments of Formula (I-3): if Z is —C(O)—, then $R_{1-1}$ may also be —N(CH$_3$)(OCH$_3$); if Z is —C(O)O—, then $R_{1-1}$ is not hydrogen; and if Z is —C(O)O—, then X does not include —O— groups.

For certain embodiments, particularly embodiments of Formula (I-4): if Z is —C(O)—, then $R_{1-1}$ may also be —N(CH$_3$)(OCH$_3$); if Z is —C(O)O—, then $R_{1-1}$ is not hydrogen; and if Z is —C(O)O—, then X does not include —O— groups.

For certain embodiments, particularly embodiments of Formula (II): if Z is —C(O)—, then $R_{1-1}$ may also be —N(CH$_3$)(OCH$_3$); if Z is —C(O)O—, then $R_{1-1}$ is not hydrogen; and if Z is —C(O)O—, then X does not include —O— groups.

For certain embodiments, Z is —C(O)— and preferably $R_{1-1}$ is selected from the group consisting of aryl, alkyl, and —N(CH$_3$)OCH$_3$. For certain other embodiments, $R_{1-1}$ is selected from the group consisting of methyl, ethyl, n-propyl, isopropyl, cyclopropyl, n-butyl, sec-butyl, isobutyl, tert-butyl, n-pentyl, cyclopentyl, n-hexyl, cyclohexyl, phenyl, 4-chlorophenyl and 2,4-dichlorophenyl.

For certain embodiments, Z is —C(O)O— and preferably $R_{1-1}$ is selected from the group consisting of alkyl and aryl.

For certain embodiments, Z is —C(-Q-R$_{1-3}$)$_2$— and preferably $R_{1-1}$ is selected from the group consisting of alkyl, aryl, and hydrogen. For certain of these embodiments, Q is —O—.

For certain embodiments, Z is —C(-Q-R$_{1-3}$)$_2$— and preferably the 5-, 6-, or 7-membered ring formed by the joining of the $R_{1-3}$ groups is optionally fused to one or two saturated or unsaturated 5-, 6-, or 7-membered rings or is substituted by one or more substituents selected from the group consisting of aryl, heteroaryl, halogen, haloalkyl, alkylene-O-alkyl, and substituted aryl. For certain of these embodiments, $R_{1-3}$ is alkyl, or the $R_{1-3}$ groups join to form a 5-membered ring.

Preparation of the Compounds

Compounds of the invention can be prepared according to the routes shown herein where $R_{1-1}$, $R_{1-3}$, $R_{1-6}$, $R_2$, R, Q, X, and n are as defined above except that $R_{1-1}$ is other than —N(CH$_3$)(OCH$_3$). In Reaction Schemes 1a, 1b, 2b, 4, and 6, R is not hydroxy, $R_{1-1}$ is not hydrogen, and $R_{1-1}$ and $R_2$ do not contain substituents that one skilled in the art would recognize as being reactive with Grignard reagents. These substituents include, for example, ketone, ester, hydroxy, and cyano (i.e., nitrile) groups as well as groups containing —NH—.

Ketones of the present invention of Formula Ia can be prepared by one of two routes where the ketone group is derived from an alcohol intermediate, as shown in Reaction Schemes 1a and 1b. Alternatively, ketones of the present invention can be prepared by routes where the ketone group is derived from a ketal or acetal intermediate as shown in Reaction Schemes 2a and 2b. In another alternative embodiment, they can be prepared by a route where the ketone group is derived from an ester intermediate, as shown in Reaction Scheme 4.

Ketals or acetals of the present invention of Formula XXI can be prepared by the route shown in Reaction Scheme 2a, which also outlines the preparation of compounds of Formula III. Ketals or acetals of the present invention of Formula Id can be prepared by the route shown in Reaction Scheme 3.

Esters of the present invention of Formula Ib can be prepared as shown in Reaction Scheme 5 starting with a compound of Formula XXV, the preparation of which is shown in Reaction Scheme 4.

Weinreb amides of the present invention of Formula Ie can be prepared by a route where the amide group is derived from an ester intermediate, as shown in Reaction Scheme 4.

Reaction Scheme 1a

In step (1) of Reaction Scheme 1a, a 4-chloro-3-nitroquinoline of Formula VI is treated with an amino alcohol in the presence of triethylamine in a suitable solvent such as dichloromethane, wherein the amino alcohol is of the general formula H$_2$N—X—CH$_2$—OH and X is as defined herein. Numerous amino alcohols of the formula H$_2$N—X—CH$_2$—OH are commercially available; others can be readily synthesized using well-known methods. Many 4-chloro-3-nitroquinolines of Formula VI are known or can be prepared using known synthetic methods, see for example, U.S. Pat. Nos. 4,689,338; 5,175,296; 5,367,076; and 5,389,640; and the references cited therein.

The resultant compound of Formula VII can be reduced in step (2) of Reaction Scheme 1a using a variety of methods to provide a quinoline-3,4-diamine of Formula VIII. The reaction can be carried out by hydrogenation using a heterogeneous hydrogenation catalyst such as platinum on carbon. The hydrogenation is conveniently carried out in a Parr apparatus in a suitable solvent such as toluene or ethanol. The reaction can be carried out at ambient temperature, and the product can be isolated using conventional methods.

Alternatively, step (2) can be carried out using a one- or two-phase sodium dithionite reduction. The reaction is conveniently carried out using the conditions described by Park, K. K.; Oh, C. H.; and Joung, W. K.; *Tetrahedron Lett.* 1993, 34, 7445-7446 by adding sodium dithionite to a compound of Formula VII in a mixture of dichloromethane and water at ambient temperature in the presence of potassium carbonate and ethyl viologen dibromide. The product can be isolated using conventional methods.

In step (3) of Reaction Scheme 1a, a quinoline-3,4-diamine of Formula VIII is treated with a carboxylic acid equivalent to provide a 1H-imidazo[4,5-c]quinoline of Formula IX. Suitable carboxylic acid equivalents include orthoesters of Formula R$_2$C(O-alkyl)$_3$, 1,1-dialkoxyalkyl alkanoates of Formula R$_2$C(O-alkyl)$_2$(O—C(O)-alkyl), and acid chlorides of Formula R$_2$C(O)Cl. The selection of the carboxylic acid equivalent is determined by the desired substituent at $R_2$. For example, triethyl orthoformate will provide a compound where $R_2$ is hydrogen, and trimethyl orthovalerate will provide a compound where $R_2$ is a butyl group. The reaction is conveniently carried out by adding the carboxylic acid equivalent to a quinoline-3,4-diamine of Formula VIII in a suitable solvent such as toluene or xylenes. Optionally, catalytic pyridine hydrochloride or pyridium p-toluenesulfonate can be added. The reaction is carried out at a temperature high enough to drive off alcohol or water formed during the reaction. Conveniently, a Dean-Stark trap can be used to collect the volatiles.

Optionally, the alcohol group on the compound of Formula VII can be protected with a suitable alcohol protecting group prior to step (2), and this protecting group can be removed prior to step (4). Suitable protecting groups include the tert-butyldimethylsilyl group, which can be introduced and removed using conventional methods.

In step (4) of Reaction Scheme 1a, the alcohol-substituted 1H-imidazo[4,5-c]quinoline of Formula IX is oxidized to an aldehyde-substituted 1H-imidazo[4,5-c]quinoline of Formula X using conventional methods, for example, Swern conditions. The Swern oxidation is conveniently carried out by adding the compound of Formula IX followed by triethylamine to a mixture of oxalyl chloride and dimethylsulfoxide in a suitable solvent, such as dichloromethane. The reaction can be carried out at sub-ambient temperatures, such as −78° C., and the product can be isolated using conventional methods.

The aldehyde-substituted 1H-imidazo[4,5-c]quinoline of Formula X is then treated with a Grignard reagent in step (5) of Reaction Scheme 1a. The Grignard reagent is of the formula $R_{1-1}$MgHalide to form a compound of Formula XI. Several of these reagents are commercially available; others can be prepared using known synthetic methods. The reaction is conveniently carried out by adding a solution of the Grignard reagent to a solution of the compound of Formula X in a suitable solvent such as tetrahydrofuran. The reaction can be carried out at ambient temperature, and the product can be isolated using conventional methods.

In step (6) of Reaction Scheme 1a, an alcohol-substituted 1H-imidazo[4,5-c]quinoline of Formula XI is oxidized to a ketone of Formula XII using conventional methods. The reaction is conveniently carried out under Swern conditions, described in step (4) above.

In step (7) of Reaction Scheme 1a, a ketone-substituted 1H-imidazo[4,5-c]quinoline of Formula XII is oxidized to provide an N-oxide of Formula XIII using a conventional oxidizing agent capable of forming such compounds. For example, the reaction can be conveniently carried out by adding 3-chloroperoxybenzoic acid to a solution of a compound of Formula XII in a solvent, such as chloroform or dichloromethane, at ambient temperature.

In step (8) of Reaction Scheme 1a, the N-oxide of Formula XIII is aminated to provide a ketone-substituted 1H-imidazo[4,5-c]quinolin-4-amine of Formula Ia. Step (8) involves the activation of an N-oxide of Formula XIII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula XIII in a suitable solvent, such as dichloromethane or chloroform, and then adding p-toluenesulfonyl chloride. The reaction can be carried out at ambient temperature. The resultant ketone-substituted 1H-imidazo[4,5-c]quinolin-4-amines of Formula Ia or pharmaceutically acceptable salt thereof can be isolated from the reaction mixture using conventional methods.

Reaction Scheme 1a

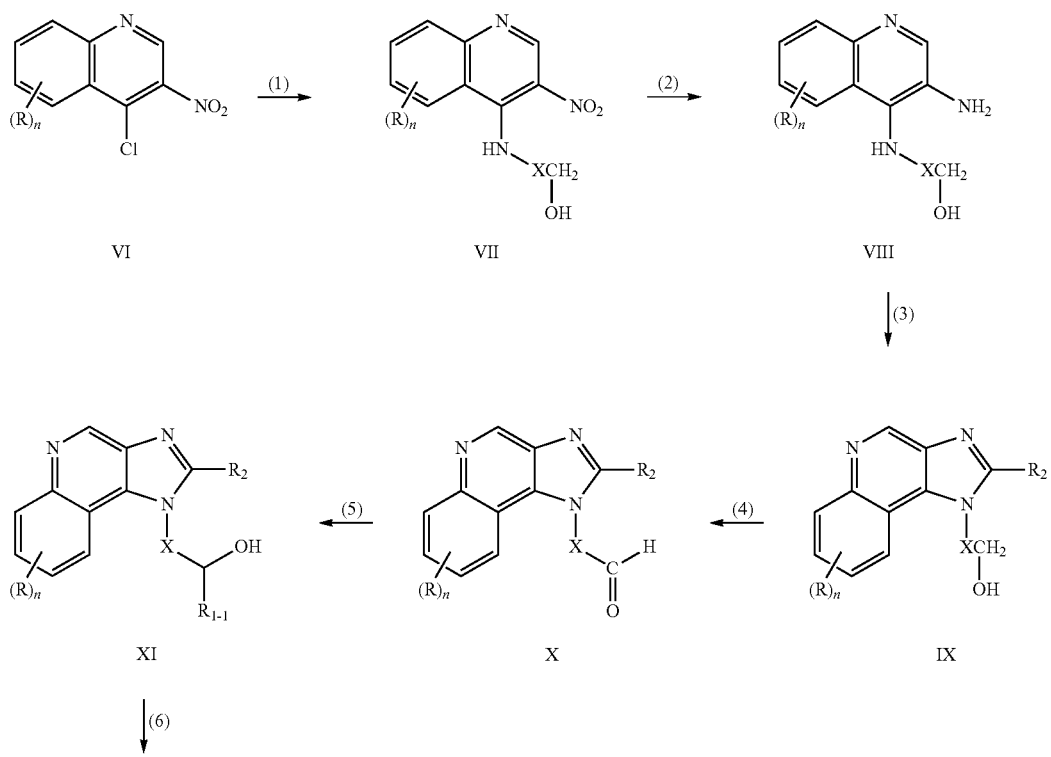

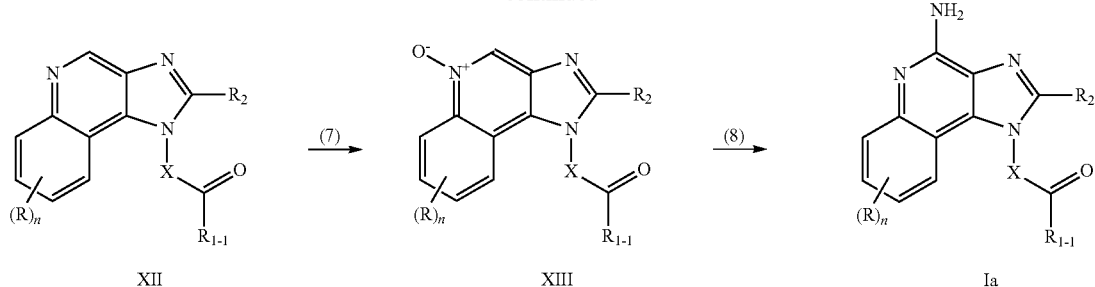

Reaction Scheme 1b

In Reaction Scheme 1b, the reactions are very similar to those of Reaction Scheme 1a but in a different order. In step (1) of Reaction Scheme 1b, a 4-chloro-3-nitroquinoline of Formula VI is treated with an amino alcohol as in step (1) of Reaction Scheme 1a. In step (2), the resultant compound of Formula VII is oxidized using conventional methods as in step (4) of Reaction Scheme 1a to form an aldehyde of Formula XIV. In step (3), the resultant aldehyde of Formula XIV is treated with a Grignard reagent as in step (5) of Reaction Scheme 1a to form a compound of Formula XV. In step (4), the compound of Formula XV is oxidized as in step (6) of Reaction Scheme 1a to form a compound of Formula XVI. In step (5), the compound of Formula XVI is reduced as in step (2) of Reaction Scheme 1a to form a ketone-substituted quinoline-3,4-diamine of Formula XVII. In step (6), the quinoline-3,4-diamine of Formula XVII is cyclized using, for example, an ortho ester, as in step (3) in Reaction Scheme 1a to form a ketone-substituted 1H-imidazo[4,5-c]quinoline of Formula XII. In step (7), the compound of Formula XII is oxidized to the N-oxide as in step (7) of Reaction Scheme 1a to form a compound of Formula XIII. In step (8), the N-oxide of Formula XIII can be aminated as in step (8) of Reaction Scheme 1a to provide the ketone-substituted 1H-imidazo[4,5-c]quinolin-4-amine of Formula Ia.

Reaction Scheme 1b

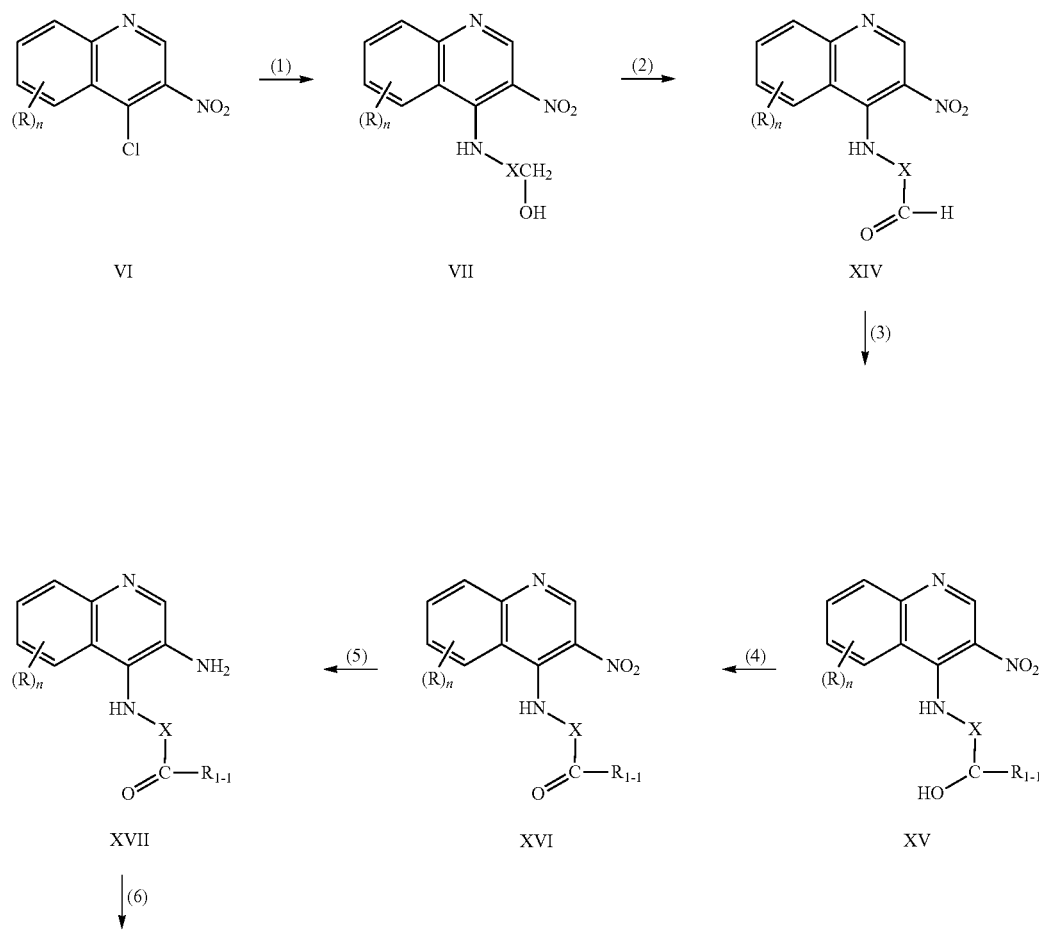

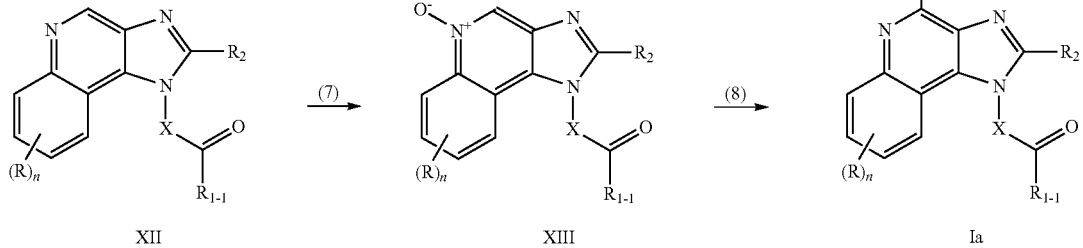

Reaction Scheme 2a

Ketones of the invention of Formula Ia and ketals and acetals of the invention of Formula XXI can be prepared according to Reaction Scheme 2a. In step (1) of Reaction Scheme 2a, a 4-chloro-3-nitroquinoline of Formula VI is reacted with a compound of the formula $H_2N-X-C(R_{1-1})(O-R_{1-4})_2$, such as an amino ketal of this formula, wherein $R_{1-1}$ is methyl and $R_{1-6}$ is ethylene, in the presence of triethylamine in a suitable solvent, such as chloroform or dichloromethane. Compounds of the formula $H_2N-X-C(R_{1-1})(O-R_{1-6})_2$ can be commercially obtained or readily synthesized using conventional methods. For example, see C. J. Stewart et al., *J. Liebigs Ann. der Chem.*, 1978, 57-65 and PCT Publication WO 01/51486.

Ketals of Formula $H_2NCH_2C(CH_3)_2CH_2C(O-R_{1-6})_2CH_3$ can be prepared according to referenced methods by the reaction of nitromethane and mesityl oxide, conversion of the resulting ketone to a ketal, and reduction of the nitro group to an amine.

The resultant compound of Formula XVIII can be reduced using a variety of methods in step (2) of Reaction Scheme 2a to form a ketal- or acetal-substituted quinoline-3,4-diamine of Formula III. The reduction can be carried out as described for step (2) of Reaction Scheme 1a.

In step (3) of Reaction Scheme 2a, the quinoline-3,4-diamine of Formula III is treated with a carboxylic acid equivalent to form a ketal- or acetal-substituted 1H-imidazo[4,5-c]quinoline of Formula XIX. The reaction can be carried out as described for step (3) of Reaction Scheme 1a.

In step (4) of Reaction Scheme 2a, the 1H-imidazo[4,5-c]quinoline of Formula XIX can be converted to the N-oxide of Formula XX using the method outlined in step (7) of Reaction Scheme 1a. In step (5), the N-oxide of Formula XX can be aminated to the compound (e.g., ketal) of Formula XXI (a subset of the compounds of Formula Id) as described in step (8) of Reaction Scheme 1a. The product or pharmaceutically acceptable salt thereof can be isolated using conventional methods.

In step (6), compounds of Formula XXI can be converted to ketones of Formula Ia by acid-catalyzed hydrolysis. The reaction is conveniently carried out by adding a strong acid, such as hydrochloric acid, to a ketal of Formula XXI. The reaction may be carried out at ambient temperature in a suitable solvent such as water. The product or pharmaceutically acceptable salt thereof can be isolated using conventional methods.

Reaction Scheme 2a

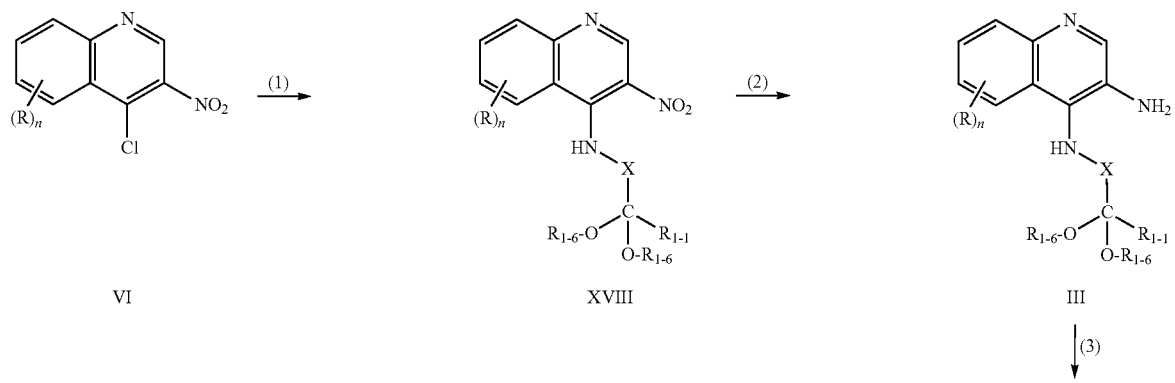

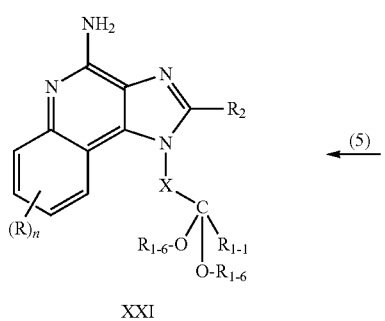 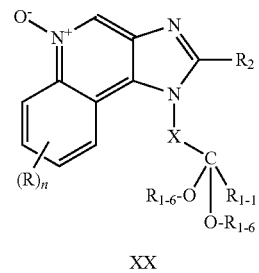 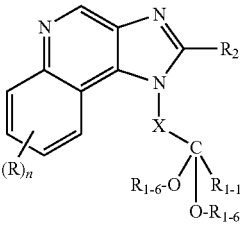

XXI                    XX                     XIX

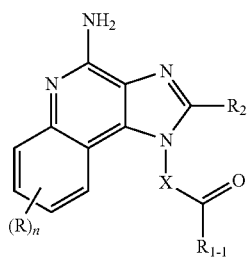

Ia

Reaction Scheme 2b

Compounds of Formula Ia can also be prepared according to Reaction Scheme 2b. In step (1) of Reaction Scheme 2b, an acetal of Formula XIX-B, which is a subset of Formula XIX where $R_{1-1}$ is hydrogen, undergoes acid-catalyzed hydrolysis to provide an aldehyde of Formula X. The reaction can be carried out as described for step (6) of Reaction Scheme 2a.

In step (2) of Reaction Scheme 2b, an aldehyde of Formula X reacts with a Grignard reagent of Formula $R_{1-1}$MgHalide. The reaction can be carried out as described in step (5) of Reaction Scheme 1a to provide an alcohol of Formula XI.

In steps (3) through (5) of Reaction Scheme 2b, an alcohol of Formula XI is oxidized using conventional methods to a ketone-substituted 1H-imidazo[4,5-c]quinoline of Formula XII, which is converted to a N-oxide of Formula XIII. The compound of Formula XIII is then aminated to provide a ketone-substituted 1H-imidazo[4,5-c]quinolin-4-amine of Formula Ia. Steps (3), (4), and (5) of Reaction Scheme 2b can be carried out as described for steps (6), (7), and (8) of Reaction Scheme 1a.

Reaction Scheme 2b

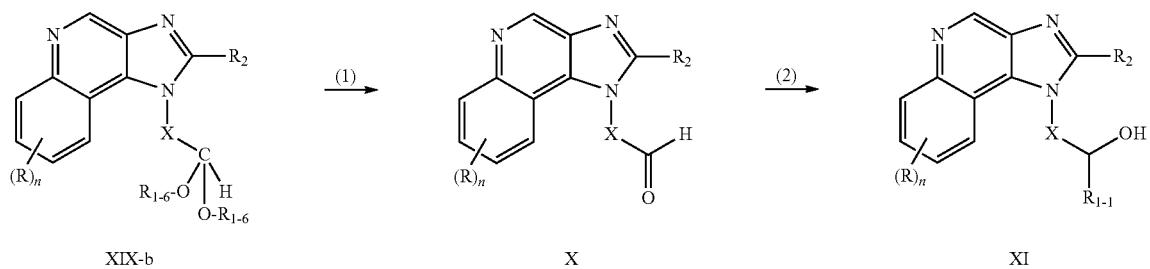

XIX-b                    X                    XI

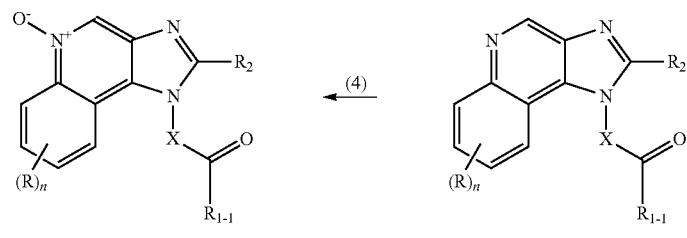

Ia             XIII             XII

Reaction Scheme 3

Ketals and acetals of the invention can be prepared according to Reaction Scheme 3. Step (1) of Reaction Scheme 3 involves the conversion of a ketone or aldehyde of Formula XII to a ketal or acetal of Formula XIX by reaction with a compound of Formula H-Q-$R_{1-3}$ or H-Q-$R_{1-3}$-Q-H. The reaction can be carried out by treating a ketone or aldehyde of Formula XII with a compound of Formula H-Q-$R_{1-3}$-Q-H or two equivalents of a compound of Formula H-Q-$R_{1-3}$ in the presence of an acid catalyst. Conditions for this reaction are well known to one skilled in the art. See, for example, Greene, T. W.; Wuts, P. G. M. *Protective Groups in Organic Synthesis*; John Wiley & Sons, Inc.: New York, $2^{nd}$ Ed, 1991, p. 178.

In step (2) of Reaction Scheme 3, a compound of Formula XXII is oxidized to a 1H-imidazo[4,5-c]quinoline-5N-oxide of Formula XXIII, which is then aminated to a 1H-imidazo[4,5-c]quinolin-4-amine of Formula Id. Steps (2) and (3) of Reaction Scheme 3 can be carried out as steps (7) and (8) of Reaction Scheme 1a. The product or pharmaceutically acceptable salt thereof can be isolated using conventional methods.

Alternatively, ketones of Formula Ia can be converted to ketals of Formula Id by the reaction described in step (1) of Reaction Scheme 3.

Reaction Scheme 3

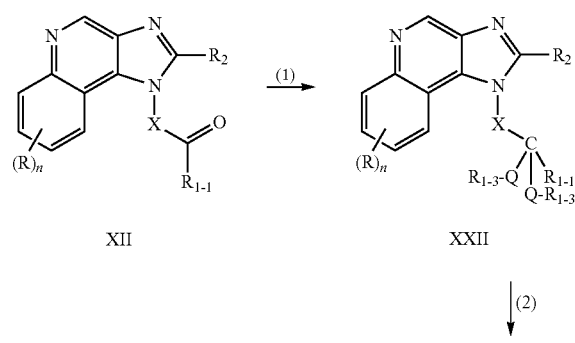

XII             XXII

-continued

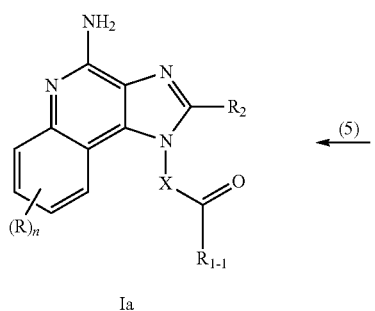

Id             XXIII

Reaction Scheme 4

Compounds of Formula Ia and Formula Ie can be prepared according to Reaction Scheme 4. In step (1) of Reaction Scheme 4, a 4-chloro-3-nitroquinoline of Formula VI is reacted with a compound of the formula $H_2N-X-C(O)(O-R_{1-1})$—HCl to form a compound of Formula XXIV. This reaction is conveniently carried out in the presence of triethylamine in a suitable solvent, such as dichloromethane. Compounds of the formula $H_2N-X-C(O)(O-R_{1-1})$—HCl can be commercially obtained or readily synthesized using conventional methods. For example, the amino ester wherein $R_{1-1}$ is ethyl and X is propylene or dodecylene can be synthesized according to the procedure of C. Temple et al., *J. Med. Chem.*, 1988, 31, 697-700.

In steps (2) and (3) of Reaction Scheme 4, a compound of Formula XXIV is reduced to form a quinoline-3,4-diamine of Formula IV, which can be cyclized with a carboxylic acid equivalent to form a 1H-imidazo[4,5-c]quinoline of Formula XXV. Steps (2) and (3) of Reaction Scheme 4 can be carried out as described for steps (2) and (3) of Reaction Scheme 1a.

In step (4), the ester group of a 1H-imidazo[4,5-c]quinoline Formula XXV is converted to a Weinreb amide to provide a 1H-imidazo[4,5-c]quinoline of Formula XXVI. The transformation can be carried out by base-promoted hydrolysis of the ester to form a carboxylic acid, conversion to an acid chloride using conventional methods, and finally treating the acid chloride with N,O-dimethylhydroxylamine hydrochloride to form a Weinreb amide of Formula XXVI. The base-promoted hydrolysis is conveniently carried out by adding sodium hydroxide to an ester-substituted 1H-imidazo[4,5-c]quinoline Formula XXV in a suitable solvent such as ethanol. The reaction can be carried out at ambient temperature, and the product can be isolated using conventional methods. The conversion of the resulting carboxylic acid to an acid chloride is conveniently carried out by slowly adding oxalyl chloride to a solution of the carboxylic acid in a suitable solvent such as dichloromethane. The reaction can be carried out at a sub-ambient temperature, such as 0° C. The resulting acid chloride can then be treated with N,O-dimethylhydroxylamine hydrochloride followed by triethylamine in a suitable solvent such as dichloromethane. The reaction can be run at ambient temperature, and the product of Formula XXVI can be isolated using conventional methods.

Alternatively, step (4) can be carried out in one step by treating an ester-substituted 1H-imidazo[4,5-c]quinoline Formula XXV with an aluminum reagent made from trimethylaluminum and N,O-dimethylhydroxylamine hydrochloride. The reaction is conveniently carried out by adding a solution of an ester-substituted 1H-imidazo[4,5-c]quinoline of Formula XXV in a suitable solvent such as dichloromethane to a pre-reacted mixture of trimethylaluminum and N,O-dimethylhydroxylamine hydrochloride in a suitable solvent such as dichloromethane. The reaction can then be heated at an elevated temperature, for example, the reflux temperature of the solvent. The product can be isolated using conventional methods.

In steps (5) and (6) of Reaction Scheme 4, a 1H-imidazo[4,5-c]quinoline of Formula XXVI is converted to a N-oxide of Formula XXVII, which is aminated to provide a 1H-imidazo[4,5-c]quinolin-4-amine of Formula Ie. Steps (5) and (6) of Reaction Scheme 4 can be carried out as described for steps (7) and (8) of Reaction Scheme 1a. The product or pharmaceutically acceptable salt thereof can be isolated using conventional methods.

Compounds of Formula Ia are available using an alternative route shown in Reaction Scheme 4 steps (7), (8), and (9). The Weinreb amide of Formula XXVI is treated with a Grignard reagent of Formula $R_{1-1}$MgHalide in step (7) to form a ketone of Formula XII. The Grignard reaction can be carried out as described in step (5) of Reaction Scheme 1a. In step (8), the ketone-substituted 1H-imidazo[4,5-c]quinoline of Formula XII is oxidized to an N-oxide of Formula XIII as described in step (7) of Reaction Scheme 1a. In step (9), the N-oxide of Formula XIII is aminated as described in step (8) of Reaction Scheme 1a to provide the ketone-substituted 1H-imidazo[4,5-c]quinolin-4-amine of Formula Ia.

Reaction Scheme 4

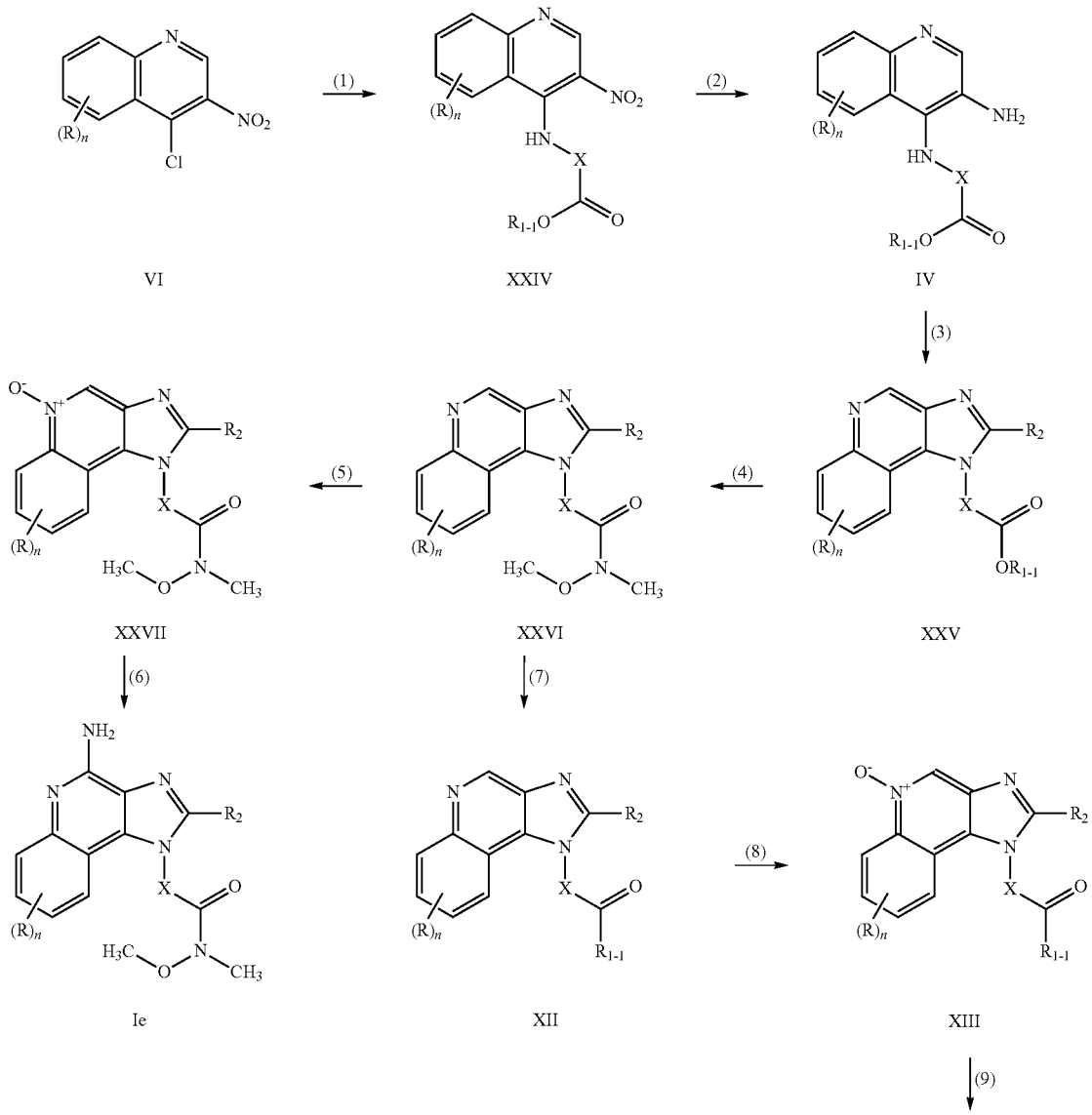

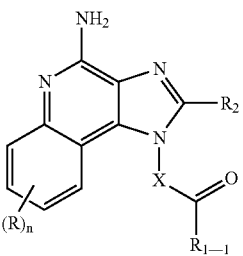

Ia

Reaction Scheme 5

In Reaction Scheme 5, a 1H-imidazo[4,5-c]quinoline of Formula XXV, prepared as described in steps (1) through (3) of Reaction Scheme 5, is converted to a compound of Formula Ib. In step (1), the 1H-imidazo[4,5-c]quinoline of Formula XXV is oxidized to an N-oxide as in step (7) of Reaction Scheme 1a to form a compound of Formula XXVIII. In step (2), the N-oxide of Formula XXVIII is aminated as in step (8) of Reaction Scheme 1a to provide the ester-substituted 1H-imidazo[4,5-c]quinolin-4-amine of Formula Ib. The product or pharmaceutically acceptable salt thereof can be isolated using conventional methods.

Reaction Scheme 5

In Reaction Scheme 5 a 1H-imidazo [4,5-c]quinoline of Formula XXV, prepared as described in steps (1) through (3) of Reaction Scheme 5, is converted to a compound of Formula Ib. In step (1), the 1H-imidazo[4,5-c]quinoline of Formula XXV is oxidized to an N-oxide as in step (7) of Reaction Scheme 1a to form a compound of Formula XXVII. In step (2), the N-oxide of Formula XXVIII is aminated as in step (8) of Reaction Scheme 1a to provide the ester-sustituted 1H-imidazo[4,5-c]quinolin-4-amine of Formula Ib. The product of pharmaceutically acceptable salt thereof can be isolated using conventional methods.

Reaction Scheme 5

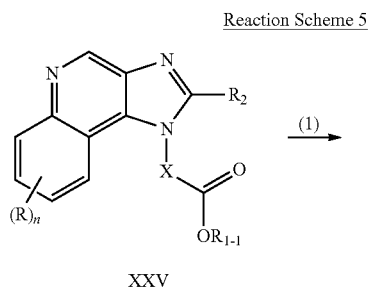

XXV

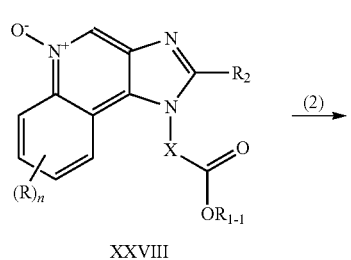

XXVIII

-continued

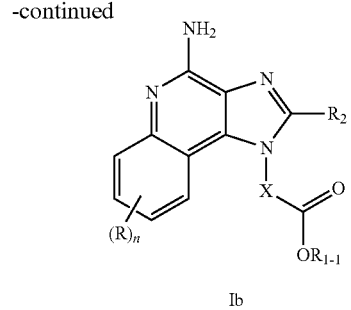

Ib

Reaction Scheme 6

Ketones of Formula I-3b can be prepared according to Reaction Scheme 6, where $R_{1-1}$, $R_2$, $R_{A'}$, $R_{B'}$, and X are as defined above and Ph is phenyl. In step (1) of Reaction Scheme 6, a 2,4-dichloro-3-nitropyridine of Formula XXX is reacted with an amino ester of the Formula $H_2N$—X—C(O)—O-alkyl or a hydrochloride salt thereof to form a 2-chloro-3-nitropyridine of Formula XXXI. The reaction is conveniently carried out by combining an amino ester of Formula $H_2N$—X—C(O)—O-alkyl-HCl and a 2,4-dichloro-3-nitropyridine of Formula XXX in the presence of a base such as triethylamine in an inert solvent such as N,N-dimethylformamide (DMF). The reaction can be carried out at ambient temperature, and the product can be isolated from the reaction mixture using conventional methods. Many 2,4-dichloro-3-nitropyridines of the Formula XXX are known and can be readily prepared using known synthetic methods. (See, for example, Dellaria et al, U.S. Pat. No. 6,525,064 and the references cited therein.)

In step (2) of Reaction Scheme 6, a 2-chloro-3-nitropyridine of Formula XXXI is reacted with an alkali metal azide to provide an 8-nitrotetrazolo[1,5-a]pyridin-7-amine of Formula XXXII. The reaction can be carried out by combining the compound of Formula XXXI with an alkali metal azide, for example, sodium azide, in a suitable solvent such as acetonitrile/water, preferably 90/10 acetonitrile/water, in the presence of cerium III chloride, preferably cerium III chloride heptahydrate. Optionally, the reaction can be carried out with heating, for example, at the reflux temperature. Alternatively, the reaction can be carried out by combining the compound of Formula XXXI with an alkali metal azide, for example, sodium azide, in a suitable solvent such as DMF and heating, for example to about 50-60° C., optionally in the presence of ammonium chloride. The product can be isolated from the reaction mixture using conventional methods.

In step (3) of Reaction Scheme 6, an 8-nitrotetrazolo[1,5-a]pyridin-7-amine of Formula XXXVI is reduced to provide a tetrazolo[1,5-a]pyridine-7,8-diamine of Formula XXXIII.

The reduction can be carried out by hydrogenation using a conventional heterogeneous hydrogenation catalyst, for example, platinum on carbon or palladium on carbon. The reaction can conveniently be carried out on a Parr apparatus in a suitable solvent such as acetonitrile or ethyl acetate. The product can be isolated from the reaction mixture using conventional methods. Alternatively, the reduction can be carried out using the one- to two-phase sodium dithionite reduction described in step (2) of Reaction Scheme 1a.

In step (4) of Reaction Scheme 6, a tetrazolo[1,5-a]pyridine-7,8-diamine of Formula XXXIII is reacted with a carboxylic acid equivalent to provide a 7H-imidazo[4,5-c]tetrazolo[1,5-a]pyridine of Formula XXXIV. The reaction can be carried out as described in step (3) of Reaction Scheme 1a, and the product can be isolated from the reaction mixture using conventional methods.

In step (5) of Reaction Scheme 6, the ester group of the 7H-imidazo[4,5-c]tetrazolo[1,5-a]pyridine of Formula XXXIV is converted to a Weinreb amide to provide a 7H-imidazo[4,5-c]tetrazolo[1,5-a]pyridine of Formula XXXV. The conversion can be carried out as described in step (4) of Reaction Scheme 4, and the product can be isolated from the reaction mixture using conventional methods.

In step (6) of Reaction Scheme 6, the Weinreb amide of Formula XXXV is treated with a Grignard reagent of Formula $R_{1-1}$MgHalide to form a ketone of Formula XXXVI. The Grignard reaction can be carried out as described in step (5) of Reaction Scheme 1a, and the product can be isolated from the reaction mixture using conventional methods.

In step (7) of Reaction Scheme 6, a 7H-imidazo[4,5-c]tetrazolo[1,5-a]pyridine of Formula XXXVI is reacted with triphenylphosphine to form an N-triphenylphosphinyl intermediate of Formula XXXVII. The reaction with triphenylphosphine can be run in a suitable solvent such as toluene or 1,2-dichlorobenzene under an atmosphere of nitrogen with heating, for example at the reflux temperature. The product can be isolated from the reaction mixture using conventional methods.

In step (8) of Reaction Scheme 6, an N-triphenylphosphinyl intermediate of Formula XXXVII is hydrolyzed to provide a ketone substituted 1H-imidazo[4,5-c]pyridin-4-amine of Formula I-3b. The hydrolysis can be carried out by general methods well known to those skilled in the art, for example, by heating in a lower alkanol in the presence of an acid. The product can be isolated from the reaction mixture using conventional methods as the compound of Formula I-3b or as a pharmaceutically acceptable salt thereof.

Esters of Formula I-3 (Z is —C(O)O—) can be prepared by omitting steps (5) and (6).

Weinreb amides of Formula I-3 (Z is —C(O)— and $R_{1-1}$ is —N(CH$_3$)(OCH$_3$)) can be prepared from esters of Formula I-3 using the method of step (5).

Reaction Scheme 6

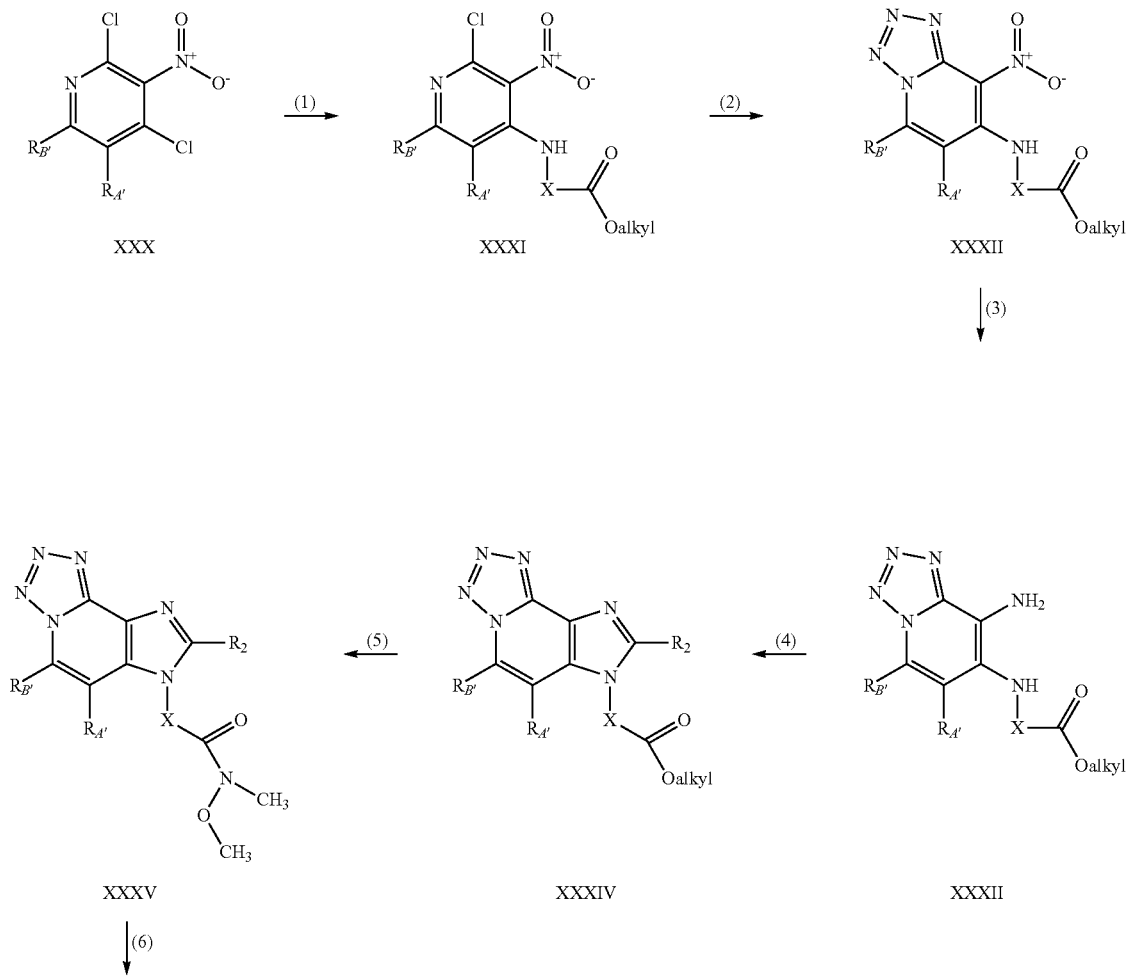

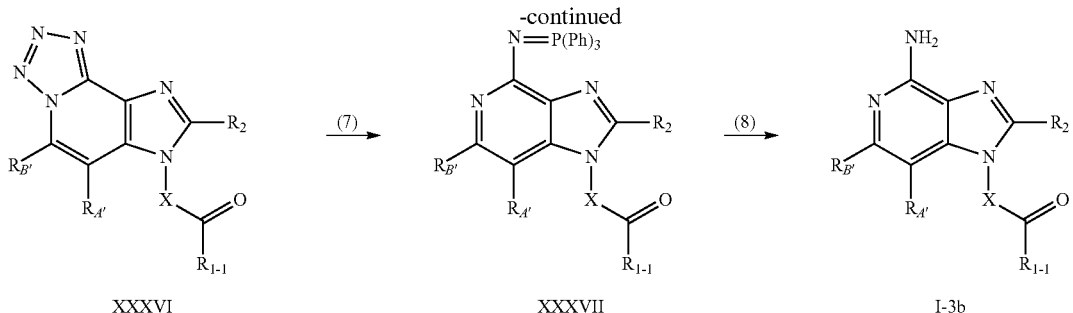

XXXVI     XXXVII     I-3b

Reaction Scheme 7

Ketones of Formula I-4b can be prepared according to Reaction Scheme 7, wherein $R_b$ is alkyl, alkoxy, or $-NR_9)_2$ and R2b, $R_{1-1}b$, and Xb are subsets of $R_2$, $R_{1-1}$, and X as defined above that do not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents.

In step (I) of Reaction Scheme 7, a 1H-imidazo[4,5-c]quinoline of Formula XIb is converted to a 1H-imidazo[4,5-c]quinolin-4-amine of Formula XXXVIIIb. The conversion can be carried out as described in steps (7) and (8) of Reaction Scheme 1a, and the product can be isolated from the reaction mixture using conventional methods.

num (IV) oxide to a solution of the compound of Formula XXXVIIIb in trifluoroacetic acid and placing the reaction under hydrogen pressure. The reaction can be carried out on a Parr apparatus at ambient temperature. The product can be isolated from the reaction mixture using conventional methods.

In step (3) of Reaction Scheme 7, the alcohol-substituted 6,7,8,9-tetrahydro-1H-imidazo[4,5-c]quinolin-4-amine of Formula XXXIXb is oxidized to a ketone-substituted 6,7,8,9-tetrahydro-1H-imidazo[4,5-c]quinolin-4-amine of Formula I-4b. The oxidation can be carried out as described in step (4) of Reaction Scheme 1a. The product or pharmaceutically acceptable salt thereof can be isolated by conventional methods.

Reaction Scheme 7

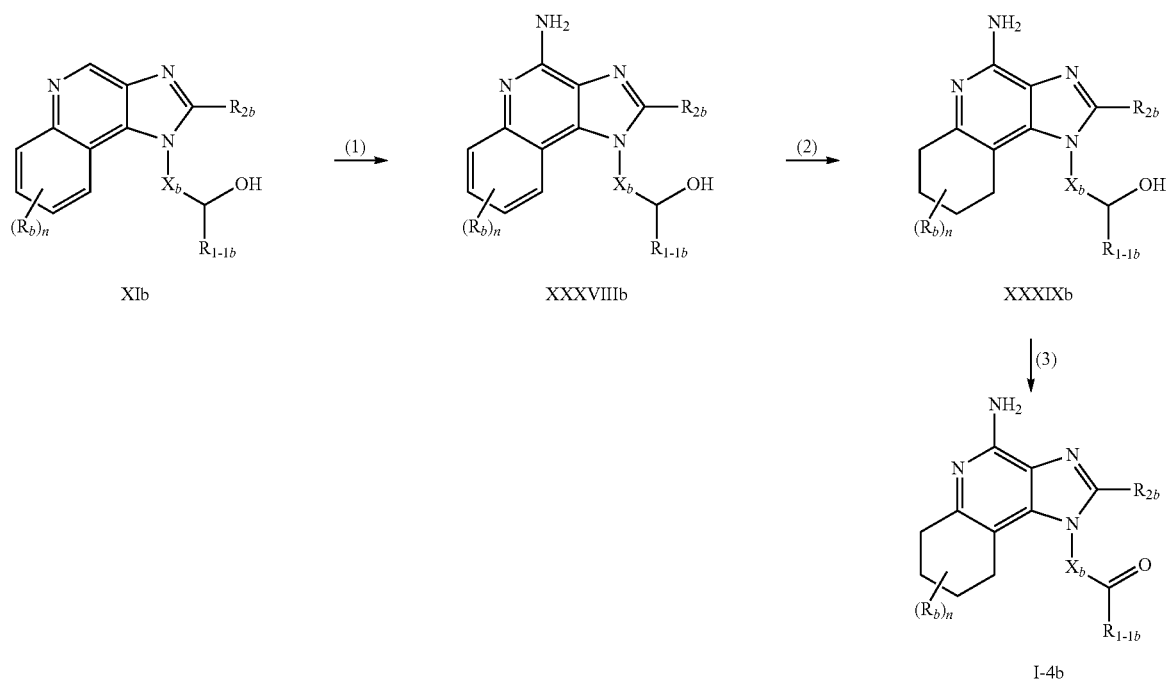

In step (2) of Reaction Scheme 7, a 1H-imidazo[4,5-c]quinolin-4-amine of Formula XXXVIIIb is reduced to a 6,7,8,9-tetrahydro-1H-imidazo[4,5-c]quinolin-4-amine of Formula XXXIXb. The reaction is conveniently carried out under hetereogeneous hydrogenation conditions by adding plati- Compounds of the invention can also be prepared using variations of the synthetic routes shown in Reaction Schemes 1 through 7 that would be apparent to one of skill in the art. For example, the ketones of Formulas Ia, I-3b, and I-4b can be converted to ketals using the method described in step (1) of Reaction Scheme (3). Compounds of the invention can also be prepared using the synthetic routes described in the EXAMPLES below.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (82 g/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the test set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-$\alpha$ (IFN-$\alpha$) and/or tumor necrosis factor-$\alpha$ (TNF-$\alpha$) as well as certain interleukins (IL). Cytokines whose biosynthesis may be induced by compounds or salts of the invention include IFN-$\alpha$, TNF-$\alpha$, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-$\gamma$ may be induced indirectly and the production of the T helper type 2 ($T_H2$) cytokines IL-4, IL-5 and IL-13 may be inhibited upon administration of the compounds or salts.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fingal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, compounds or salts of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) over a background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 µg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 µg/kg to about 5 mg/kg.

EXAMPLES

Objects and advantages of this invention are further illustrated by the following examples, but the particular materials and amounts thereof recited in these examples, as well as other conditions and details, should not be construed to unduly limit this invention.

Example 1

4-(4-Amino-2-butyl-1H-imidazo[4,5-c]quinolin-1-yl)-1-phenylbutan-1-one

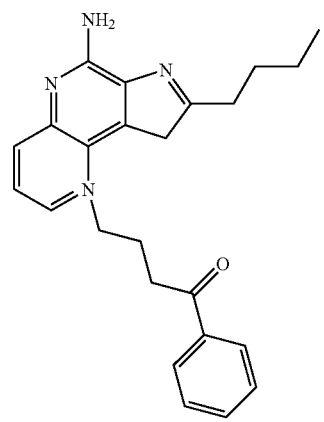

Step 1:

To a stirred mixture of 4-chloro-3-nitroquinoline (100.0 g, 479 mmol) and triethylamine (72.8 g, 719 mmol) in dichloromethane (700 mL) was added dropwise 4-amino-1-butanol (42.7 g, 479 mmol). After the addition was complete, water (500 mL) was added to the reaction mixture to cause the product to precipitate. More water (2 L) was added, and the mixture was stirred overnight and then filtered. The organic solution was dried over sodium sulfate, concentrated under reduced pressure, and combined with the product isolated by filtration to provide 4-(3-nitroquinolin-4-ylamino)butan-1-ol (113 g) as a bright yellow solid.

Step 2:

To a stirred solution of 4-(3-nitroquinolin-4-ylamino)butan-1-ol (70.0 g, 268 mmol) and triethylamine (54.2 g, 536 mmol) in chloroform (900 mL) was added tert-butyldimethylsilyl chloride (TBDMSCl, 60.6 g, 402 mmol). After 3.5 hours, additional triethylamine (19.0 g, 188 mmol) and TBDMSCl (20.2 g, 134 mmol) were added and the mixture stirred overnight. After the addition of additional TBDMSCl (4.0 g, 27 mmol), the reaction was complete as judged by thin layer chromatography (TLC). Chloroform (900 mL) was added and the mixture washed successively with 360 mL each of a 0.10 N hydrochloric acid solution, a saturated aqueous sodium bicarbonate solution, and brine; dried over sodium sulfate; filtered; and solvent evaporated to leave a mixture of [4-(tert-butyldimethylsilanyloxy)butyl](3-nitro-quinolin-4-yl)amine and tert-butyldimethylsilanol (117 g total, about 65:35 mol:mol) which was used in the next step without further purification.

Step 3:

The mixture of [4-(tert-butyldimethylsilanyloxy)butyl](3-nitro-quinolin-4-yl)amine and tert-butyldimethylsilanol (110 g) from the previous step was dissolved in toluene (880 mL) and placed in a Parr hydrogenation vessel along with 5% platinum on carbon catalyst (3.0 g). The vessel was pressurized to 50 psi ($3.4 \times 10^5$ Pa) hydrogen and shaken on the Parr apparatus for 1.5 hours, occasionally adding additional hydrogen to maintain a pressure of 50 psi ($3.4 \times 10^5$ Pa). After 3 hours, the reaction mixture was filtered through CELITE filter agent and concentrated under reduced pressure to provide $N^4$-[4-(tert-butyldimethylsilanyloxy)butyl]quinoline-3,4-diamine as a dark oil that was used directly in the next step without further purification.

Step 4:

A solution of $N^4$-[4-(tert-butyldimethylsilanyloxy)butyl]quinoline-3,4-diamine (62.9 g, 182 mmol) and trimethyl orthovalerate (45.2 g, 278 mmol) in toluene (200 mL) was heated at reflux for 2 hours and then concentrated under reduced pressure to provide 2-butyl-1-[4-(tert-butyldimethylsilanyloxy)butyl]-1H-imidazo[4,5-c]quinoline as an oil that was used directly in the next step without further purification.

Step 5:

The 2-butyl-1-[4-(tert-butyldimethylsilanyloxy)butyl]-1H-imidazo[4,5-c]quinoline from the previous step and tetrabutylammonium fluoride (142 mL of a 1 M solution in tetrahydrofuran) were dissolved in tetrahydrofuran (THF) (400 mL) and stirred for 1 hour, then concentrated under reduced pressure to provide 4-(2-butyl-1H-imidazo[4,5-c]quinolin-1-yl)butan-1-ol (20.0 g) as a light brown solid after chromatography on silica gel (elution with 10% methanol in dichloromethane).

Step 6:

A solution of dimethyl sulfoxide (DMSO, 7.88 g, 101 mmol) in dichloromethane (130 mL) was cooled in a dry ice/acetone bath and stirred. Oxalyl chloride (9.40 g, 74 mmol) was added dropwise, followed by a solution of 4-(2-butyl-1H-imidazo[4,5-c]quinolin-1-yl)butan-1-ol (20.0 g, 67.3 mmol) in dichloromethane (320 mL). After five minutes triethylamine (20.42 g, 202 mmol) was added, and the mixture was allowed to warm to room temperature. After the addition of chloroform (500 mL), the mixture was washed successively with a saturated ammonium chloride solution (200 mL) and a saturated aqueous sodium bicarbonate solution (200 mL), dried over sodium sulfate, filtered, and concentrated to a dark solid. This solid was slurried in diethyl ether until a fine solid resulted. The product was filtered and dried to provide 4-(2-butyl-1H-imidazo[4,5-c]quinolin-1-yl)butyraldehyde (17.9 g) as a light brown solid.

Step 7:

To a stirred solution of 4-(2-butyl-1H-imidazo[4,5-c]quinolin-1-yl)butyraldehyde (8.0 g, 27.1 mmol) in anhydrous THF (270 mL) was added dropwise a solution of phenylmagnesium bromide (27.08 mL of a 1 M solution in THF). After 30 minutes, the solution was quenched with saturated ammonium chloride (100 mL), diluted with ethyl acetate (300 mL), and the layers separated. The organic solution was washed successively with a saturated aqueous sodium bicarbonate solution (100 mL) and brine (100 mL), dried over sodium sulfate, filtered, and concentrated to a light orange oil. Chromatography on silica gel (elution with 5% methanol in dichloromethane) provided 4-(2-butyl-1H-imidazo[4,5-c]quinolin-1-yl)-1-phenylbutan-1-ol (4.3 g) as a light orange, gummy solid.

Step 8:

A solution of DMSO (1.35 g, 17.3 mmol) in dichloromethane (22 mL) was cooled in a dry ice/acetone bath and stirred. Oxalyl chloride (1.61 g, 12.7 mmol) was added dropwise, followed by a solution of 4-(2-butyl-1H-imidazo[4,5-c]quinolin-1-yl)-1-phenylbutan-1-ol (4.3 g, 11.5 mmol) in dichloromethane (55 mL). After five minutes, triethylamine (3.49 g, 34.5 mmol) was added, and the mixture was allowed to warm to room temperature. After the addition of chloroform (300 mL), the mixture was washed successively with a saturated ammonium chloride solution (100 mL) and a saturated aqueous sodium bicarbonate solution (100 mL), dried over sodium sulfate, filtered, and concentrated to provide 4-(2-butyl-1H-imidazo[4,5-c]quinolin-1-yl)-1-phenylbutan-1-one (4.15 g) as an off-white solid.

Step 9:

To a stirred solution of 4-(2-butyl-1H-imidazo[4,5-c]quinolin-1-yl)-1-phenylbutan-1-one (4.15 g, 11.2 mmol) in chloroform (56 mL) was added 3-chloroperoxybenzoic acid (m-CPBA, approximately 77% purity, 2.75 g, 12.3 mmol) portionwise over a several minute period. After 1 hour, the reaction was not complete as judged by TLC, so an additional charge of m-CPBA (1.0 g) was added. After stirring for 30 minutes, the mixture was diluted with chloroform (200 mL), washed successively with a saturated aqueous sodium bicarbonate solution (2×100 mL) and brine (100 mL), dried over sodium sulfate, filtered, and concentrated to provide 4-(2-butyl-5-oxido-1H-imidazo[4,5-c]quinolin-1-yl)-1-phenylbutan-1-one as a dark oil that was used directly in the next step without further purification.

Step 10:

To a vigorously stirred mixture of the 4-(2-butyl-5-oxido-1H-imidazo[4,5-c]quinolin-1-yl)-1-phenylbutan-1-one from the previous step in dichloromethane (49 mL) and ammonium hydroxide (16 mL) was added p-toluenesulfonyl chloride (2.34 g, 12.3 mmol) portionwise over several minutes. After 15 minutes the reaction mixture was diluted with chloroform (200 mL) and saturated aqueous sodium bicarbonate solution (100 mL). The layers were separated and the organic phase was washed again with a saturated aqueous sodium bicarbonate solution (100 mL). The aqueous portions were then back extracted with chloroform (50 mL). The organics were combined, dried over sodium sulfate, filtered, and concentrated to a dark yellow solid. The dark yellow solid was slurried in diethyl ether and filtered to form a fine off-white solid. This solid was recrystallized from N,N-dimethylformamide (DMF) and water to afford 4-(4-amino-2-butyl-1H-imidazo[4,5-c]quinolin-1-yl)-1-phenylbutan-1-one as an off-white fluffy solid, mp 178-180° C.

MS (APCI) m/z 387 (M+H)$^+$;

Anal. calcd for $C_{24}H_{26}N_4O$: C, 74.58; H, 6.78; N, 14.50. Found: C, 74.45; H, 6.77; N, 14.47.

Example 2

5-(4-Amino-2-butyl-1H-imidazo[4,5-c]quinolin-1-yl)pentan-2-one

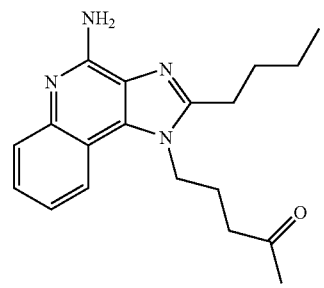

Steps 1-6 were carried out as described above for the Preparation of Example 1.

Step 7:

The general method described in Step 7 of Example 1 was used to react 4-(2-butyl-1H-imidazo[4,5-c]quinolin-1-yl)butyraldehyde (8.5 g, 28.8 mmol) with methylmagnesium bromide (20.6 mL of a 1.4 M solution in toluene/THF, 28.8 mmol) to provide 5-(2-butyl-1H-imidazo[4,5-c]quinolin-1-yl)pentan-2-ol (3.54 g) as an off-white solid after chromatography on silica gel (elution with 5% methanol in dichloromethane).

Step 8:

The general method described in Step 8 of Example 1 was used to oxidize 5-(2-butyl-1H-imidazo[4,5-c]quinolin-1-yl)pentan-2-ol (3.54 g, 11.4 mmol) with DMSO (1.33 g, 17.1 mmol), oxalyl chloride (1.59 g, 12.5 mmol), and triethylamine (3.45 g, 34.1 mmol) to provide 5-(2-butyl-1H-imidazo[4,5-c]quinolin-1-yl)pentan-2-one (2.15 g) as a dark solid.

Steps 9 and 10:

The general method described in Steps 9 and 10 of Example 1 was used to aminate 5-(2-butyl-1H-imidazo[4,5-c]quinolin-1-yl)pentan-2-one (2.15 g, 6.95 mmol) by reaction with m-CPBA (1.71 g, 7.64 mmol) to provide 5-(2-butyl-5-oxido-1H-imidazo[4,5-c]quinolin-1-yl)pentan-2-one followed by reaction with p-toluenesulfonyl chloride (1.46 g, 7.64 mmol) and ammonium hydroxide solution (10 mL) to provide 5-(4-amino-2-butyl-1H-imidazo[4,5-c]quinolin-1-yl)pentan-2-one as an off-white solid, mp 173-176° C.

MS (APCI) m/z 325 (M+H)$^+$;

Anal. calcd for $C_{19}H_{24}N_4O$: C, 70.34; H, 7.46; N, 17.27. Found: C, 70.24; H, 7.37; N, 17.25.

Example 3

4-(4-Amino-1H-imidazo[4,5-c]quinolin-1-yl)-1-phenylbutan-1-one

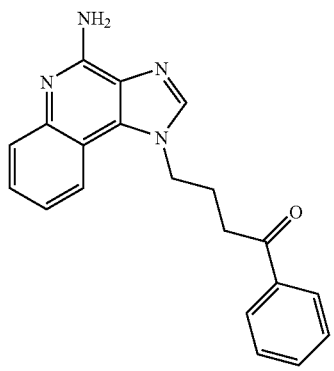 [SMILES: Nc1nc2ccccc2c2c1ncn2CCCC(=O)c1ccccc1]

Steps 1-3 were carried out as described above for the Preparation of Example 1.

Step 4:

A mixture of N$^4$-[4-(tert-butyldimethylsilanyloxy)butyl]quinoline-3,4-diamine (101 g, 293 mmol) and triethyl orthoformate (43.4 g, 293 mmol) in toluene (200 mL) was heated at reflux for 2 hours and then concentrated under reduced pressure to provide 1-[4-(tert-butyldimethylsilanyloxy)butyl]-1H-imidazo[4,5-c]quinoline as an oil that was used directly in the next step without further purification.

Step 5:

The 1-[4-(tert-butyldimethylsilanyloxy)butyl]-1H-imidazo[4,5-c]quinoline (46.0 g, 129 mmol) from the previous step and tetrabutylammonium fluoride (142 mL of a 1 M solution in THF) were dissolved in THF (400 mL) and stirred for 1 hour, then concentrated under reduced pressure to provide 4-(1H-imidazo[4,5-c]quinolin-1-yl)butan-1-ol (20.0 g) as a light brown solid after chromatography on silica gel (elution with 10% methanol in dichloromethane).

Step 6:

The general method described in Step 6 of Example 1 was used to oxidize 4-(1H-imidazo[4,5-c]quinolin-1-yl)butan-1-ol (20.0 g, 82.9 mmol) with DMSO (48.6 g, 620 mmol), oxalyl chloride (58.0 g, 456 mmol), and triethylamine (126 g, 1.25 mol) to provide 4-(1H-imidazo[4,5-c]quinolin-1-yl)butyraldehyde (10.0 g) as a light orange oil after chromatography on silica gel (elution with 10% methanol in dichloromethane) followed by brief treatment with trifluoroacetic acid (0.10 g, 1 mmol) in a mixture of THF (50 mL) and water (20 mL).

Step 7:

The general method described in Step 7 of Example 1 was used to react 4-(1H-imidazo[4,5-c]quinolin-1-yl)butyraldehyde (7.94 g, 33.2 mmol) with phenylmagnesium bromide (33.2 mL of a 1 M solution in THF, 33.2 mmol) to provide 4-(1H-imidazo[4,5-c]quinolin-1-yl)-1-phenylbutan-1-ol (7.2 g) as an off-white solid that was used directly in the next step without further purification.

Step 8:

By the general method described in Step 6 of Example 1, 4-(1H-imidazo[4,5-c]quinolin-1-yl)-1-phenylbutan-1-ol) (7.2 g, 22.7 mmol) was oxidized with DMSO (2.70 g, 34.0 mmol), oxalyl chloride (3.20 g, 25.0 mmol), and triethylamine (6.90 g, 68.1 mmol) to provide 4-(1H-imidazo[4,5-c]quinolin-1-yl)-1-phenylbutan-1-one (4.08 g) as a light yellow solid after chromatography on silica gel (elution with 10% methanol in dichloromethane).

Step 9:

The general method described in Steps 9 and 10 of Example 1 was used to aminate 4-(1H-imidazo[4,5-c]quinolin-1-yl)-1-phenylbutan-1-one (4.08 g, 12.9 mmol) by reaction with m-CPBA (3.20 g, 14.2 mmol) to provide 4-(5-oxido-1H-imidazo[4,5-c]quinolin-1-yl)-1-phenylbutan-1-one followed by reaction with p-toluenesulfonyl chloride (2.71 g, 14.2 mmol) and ammonium hydroxide solution (22 mL) to provide 4-(4-amino-1H-imidazo[4,5-c]quinolin-1-yl)-1-phenylbutan-1-one) as white needles, mp 209-211° C.

MS (APCI) m/z 331 (M+H)$^+$;

Anal. calcd for $C_{20}H_{18}N_4O$: C, 72.71; H, 5.49; N, 16.96. Found: C, 72.60; H, 5.39; N, 16.98.

Example 4

6-(4-Amino-2-butyl-1H-imidazo[4,5-c]quinolin-1-yl)-1-phenylhexan-1-one

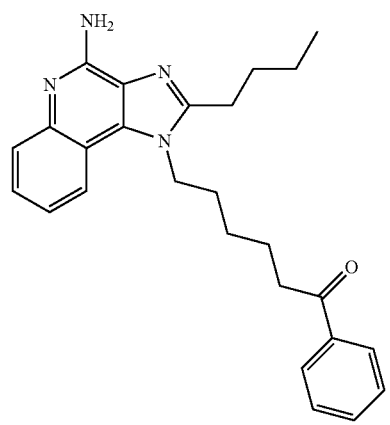 [SMILES: CCCCc1nc2c(N)nc3ccccc3c2n1CCCCCC(=O)c1ccccc1]

Step 1:
To a stirred mixture of 4-chloro-3-nitroquinoline (50.0 g, 240 mmol) and triethylamine (36.4 g, 360 mmol) in dichloromethane (370 mL) was added 6-amino-1-hexanol (28.1 g, 240 mmol) portionwise over a ten-minute period. The mixture was heated at reflux for 35 minutes, cooled, and diluted with chloroform (300 mL). The solution was washed successively with water (200 mL), a saturated aqueous sodium bicarbonate solution (200 mL), and brine (200 mL); dried over sodium sulfate; filtered; and concentrated to a bright yellow solid, 6-(3-nitroquinolin-4-ylamino)hexan-1-ol (68.3 g), that was used directly in the next step without further purification.

Step 2:
The alcohol from Step 1, 6-(3-nitro-quinolin-4-ylamino)hexan-1-ol (10.0 g, 34.6 mmol), was oxidized by the general method described in Step 6 of Example 1 with DMSO (4.05 g, 51.8 mmol), oxalyl chloride (4.83 g, 38.0 mmol), and triethylamine (10.5 g, 104 mmol) to provide 6-(3-nitroquinolin-4-ylamino)hexanal (9.9 g) as a bright yellow solid that was used directly in the next step without further purification.

Step 3:
By the general method described in Step 7 of Example 1, 6-(3-nitroquinolin-4-ylamino)hexanal (9.9 g, 34.5 mmol) was reacted with phenylmagnesium bromide (36.2 mL of a 1 M solution in THF, 36.2 mmol) to provide 6-(3-nitroquinolin-4-ylamino)-1-phenylhexan-1-ol (4.4 g) as a bright yellow solid after chromatography on silica gel (elution with ethyl acetate and hexane, 1:1, volume:volume).

Step 4:
By the general method described in Step 6 of Example 1, 6-(3-nitroquinolin-4-ylamino)-1-phenylhexan-1-ol (4.0 g, 11 mmol) was oxidized with DMSO (1.28 g, 16.4 mmol), oxalyl chloride (1.53 g, 12.0 mmol), and triethylamine (3.32 g, 32.8 mmol) to provide 6-(3-nitroquinolin-4-ylamino)-1-phenylhexan-1-one (2.27 g) as light orange crystals after recrystallization from ethyl acetate.

Step 5:
A mixture of 6-(3-nitroquinolin-4-ylamino)-1-phenylhexan-1-one (2.27 g, 6.25 mmol) and 5% platinum on carbon catalyst (0.50 g) in toluene (60 mL) was hydrogenated on a Parr shaker at 50 psi (3.4×10$^5$ Pa) for 3 hours. After filtration through CELITE filter agent and concentration under reduced pressure, 6-(3-aminoquinolin-4-ylamino)-1-phenylhexan-1-one (2.09 g) was obtained as a dark yellow oil that was used directly in the next step without further purification.

Step 6:
A solution of 6-(3-aminoquinolin-4-ylamino)-1-phenylhexan-1-one (2.09 g, 6.25 mmol) and trimethyl orthovalerate (1.52 g, 9.37 mmol) in toluene (50 mL) was heated at reflux under a Dean-Stark trap for 2 hours, then concentrated under reduced pressure to provide 6-(2-butyl-1H-imidazo[4,5-c]quinolin-1-yl)-1-phenylhexan-1-one (2.19 g) as a dark red oil that was used directly in the next step without further purification.

Steps 7 and 8:
The general method described in Steps 9 and 10 of Example 1 was used to aminate 6-(2-butyl-1H-imidazo[4,5-c]quinolin-1-yl)-1-phenylhexan-1-one (2.19 g, 5.48 mmol) by reaction with m-CPBA (1.35 g, 6.03 mmol) to provide 6-(2-butyl-5-oxido-1H-imidazo[4,5-c]quinolin-1-yl)-1-phenylhexan-1-one followed by reaction with p-toluenesulfonyl chloride (1.15 g, 6.03 mmol) and ammonium hydroxide solution (9 mL) to provide 6-(4-amino-2-butyl-1H-imidazo[4,5-c]quinolin-1-yl)-1-phenylhexan-1-one (0.50 g) as a white solid after chromatography on silica gel (elution with 10% methanol in dichloromethane) and recrystallization from ethanol, mp 149-151° C.

MS (APCI) m/z 415 (M+H)$^+$;

Anal. calcd for $C_{26}H_{30}N_4O$: C, 75.33; H, 7.29; N, 13.52. Found: C, 75.14; H, 7.13; N, 13.48.

Example 5

6-(4-Amino-1H-imidazo[4,5-c]quinolin-1-yl)-1-phenylhexan-1-one

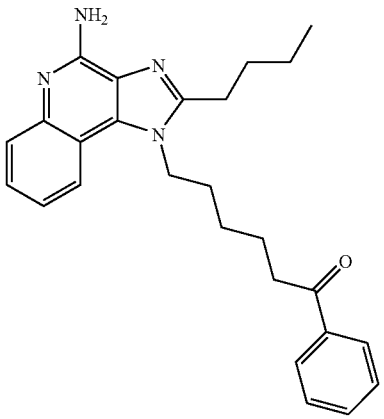 [SMILES: CCCCc1nc2c(N)nc3ccccc3c2n1CCCCCC(=O)c1ccccc1]

Step 1:
By the general method described in Step 6 of Example 4, a solution of 6-(3-aminoquinolin-4-ylamino)-1-phenylhexan-1-one (2.76 g, 8.25 mmol), trimethyl orthoformate (1.5 g, 9.9 mmol), and pyridine hydrochloride (95 mg, 0.83 mmol) in toluene (26 mL) was heated at reflux under a Dean-Stark trap for 2 hours, then concentrated under reduced pressure to provide 6-(1H-imidazo[4,5-c]quinolin-1-yl)-1-phenylhexan-1-one as a dark oil that was used directly in the next step without further purification.

Step 2:
The general method described in Steps 9 and 10 of Example 1 was used to aminate 6-(1H-imidazo[4,5-c]quinolin-1-yl)-1-phenylhexan-1-one (2.0 g, 5.8 mmol) by reaction with m-CPBA (1.44 g, 6.41 mmol) to provide 6-(5-oxido-1H-imidazo[4,5-c]quinolin-1-yl)-1-phenylhexan-1-one followed by reaction with p-toluenesulfonyl chloride (1.22 g, 6.41 mmol) and ammonium hydroxide solution (10 mL) to provide 6-(4-amino-1H-imidazo[4,5-c]quinolin-1-yl)-1-phenylhexan-1-one (0.29 g) as an off-white solid after chromatography on silica gel (elution with 5% methanol in dichloromethane) and recrystallization from dichloroethane, mp 163-165° C.

MS (APCI) m/z 359 (M+H)$^+$;

Anal. calcd for $C_{22}H_{22}N_4O$: C, 73.72; H, 6.19; N, 15.63. Found: C, 73.66; H, 5.88; N, 15.55.

Example 6

2-Methyl-1-[3-(2-methyl-[1,3]dioxolan-2-yl)propyl]-1H-imidazo[4,5-c]quinolin-4-amine

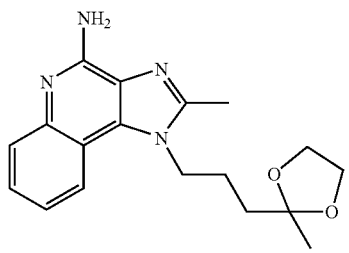 [SMILES: Cc1nc2c(N)nc3ccccc3c2n1CCCC1(C)OCCO1]

Step 1:

The general method described in Step 1 of Example 1 was used to react 4-chloro-3-nitroquinoline (45.0 g, 216 mmol), 3-(2-methyl-[1,3]dioxolan-2-yl)propylamine (37.0 g, 255 mmol, prepared as described in PCT Publication WO 01/51486) and triethylamine (37.0 g, 366 mmol) in dichloromethane for 15 hours to provide [3-(2-methyl-[1,3]dioxolan-2-yl)propyl]-(3-nitroquinolin-4-yl)amine (44.1 g) as a yellow solid after recrystallization from a toluene/hexane mixture.

Step 2:

The product from the previous step, [3-(2-methyl-[1,3]dioxolan-2-yl)propyl](3-nitro-quinolin-4-yl)amine (29.5 g, 93.0 mmol), was stirred with sodium dithionite (67.0 g, approximately 85% pure), potassium carbonate (51.4 g, 372 mmol), and ethyl viologen dibromide (0.37 g, 1 mmol) in a mixture of dichloromethane and water (375 mL each) for 15 hours. The layers were then separated, and the organic phase was washed successively with a saturated aqueous sodium bicarbonate solution and water (250 mL each), dried over potassium carbonate, filtered, and concentrated under reduced pressure to provide $N^4$-[3-(2-methyl-[1,3]dioxolan-2-yl)-propyl]quinoline-3,4-diamine (26.0 g) as a dark solid that was used directly in the next step without further purification.

Step 3:

A solution of $N^4$-[3-(2-methyl-[1,3]dioxolan-2-yl)propyl]quinoline-3,4-diamine (6.20 g, 21.6 mmol), triethyl orthoacetate (3.10 g, 25.8 mmol) and pyridinium p-toluenesulfonate (0.18 g, 0.71 mmol) in toluene (250 mL) was heated at reflux under a Dean-Stark trap for 2 hours, periodically draining off the distillate and adding fresh toluene to the reaction mixture. The solution was concentrated under reduced pressure, and the residue was taken up in dichloromethane (150 mL), washed successively with a saturated aqueous sodium bicarbonate solution and water (100 mL each), dried over potassium carbonate, filtered, and concentrated under reduced pressure to provide 2-methyl-1-[3-(2-methyl-[1,3]dioxolan-2-yl)propyl]-1H-imidazo[4,5-c]quinoline (6.70 g) as a dark oil that was used directly in the next step without further purification.

Step 4:

The general method described in Steps 9 and 10 of Example 1 was used to aminate 2-methyl-1-[3-(2-methyl-[1,3]dioxolan-2-yl)propyl]-1H-imidazo[4,5-c]quinoline (6.70 g, 21.5 mmol) by reaction with m-CPBA (9.4 g) to provide 2-methyl-1-[3-(2-methyl-[1,3]dioxolan-2-yl)-propyl]-5-oxido-1H-imidazo[4,5-c]quinoline followed by reaction with p-toluenesulfonyl chloride (7.20 g, 37.8 mmol) and ammonium hydroxide solution (100 mL) to provide 2-methyl-1-[3-(2-methyl-[1,3]dioxolan-2-yl)propyl]-1H-imidazo[4,5-c]quinolin-4-amine (3.9 g) as an off-white solid after recrystallization from toluene, mp 193-195° C.

MS (APCI) m/z 327 (M+H)$^+$;

Anal. calcd for $C_{18}H_{22}N_4O_2$: C, 66.24; H, 6.79; N, 17.17. Found: C, 66.07; H, 6.58; N, 16.91.

Examples 7, 8, 9, and 10 were prepared by the general method described above for Example 6, wherein the orthoester or acid chloride described below was substituted for triethyl orthoacetate in Step 3 of the synthesis.

Example 7

2-Ethyl-1-[3-(2-methyl-[1,3]dioxolan-2-yl)propyl]-1H-imidazo[4,5-c]quinolin-4-amine

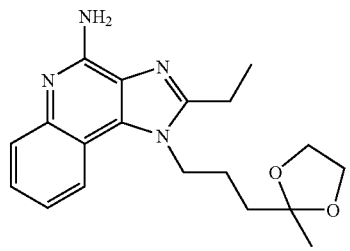 [SMILES: CCc1nc2c(N)nc3ccccc3c2n1CCCC1(C)OCCO1]

By utilizing triethyl orthopropionate in Step 3 of Example 6, 2-ethyl-1-[3-(2-methyl-[1,3]dioxolan-2-yl)propyl]-1H-imidazo[4,5-c]quinolin-4-amine was prepared, mp 195-196.5° C.

MS (APCI) m/z 341 (M+H)$^+$;

Anal. calcd for $C_{19}H_{24}N_4O_2$: C, 67.04; H, 7.1 1; N, 16.46. Found C, 66.77; H, 7.20; N, 16.41.

Example 8

1-[3-(2-Methyl-[1,3]dioxolan-2-yl)propyl]-2-propyl-1H-imidazo[4,5-c]quinolin-4-amine

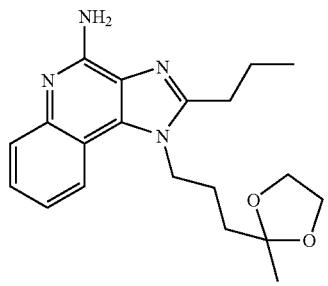 [SMILES: CCCc1nc2c(N)nc3ccccc3c2n1CCCC1(C)OCCO1]

By utilizing trimethyl orthobutyrate in Step 3 of Example 6, 1-[3-(2-methyl-[1,3]dioxolan-2-yl)propyl]-2-propyl-1H-imidazo[4,5-c]quinolin-4-amine was prepared, mp 184-186° C.

MS (APCI) m/z=355 (M+H)$^+$;

Anal. calcd for $C_{20}H_{26}N_4O_2$: C, 67.77; H, 7.39; N, 15.81. Found C, 67.55; H, 7.45; N, 15.74.

Example 9

2-Butyl-1-[3-(2-methyl-[1,3]dioxolan-2-yl)propyl]-1H-imidazo[4,5-c]quinolin-4-amine

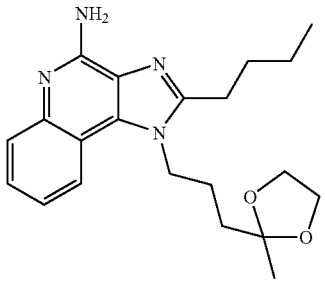 [SMILES: CCCCc1nc2c(N)nc3ccccc3c2n1CCCC1(C)OCCO1]

By utilizing trimethyl orthovalerate in Step 3 of Example 6, 2-butyl-1-[3-(2-methyl-[1,3]dioxolan-2-yl)propyl]-1H-imidazo[4,5-c]quinolin-4-amine was prepared, mp 169-171.5° C.

MS (APCI) m/z=369 (M+H)$^+$;

Anal. calcd for $C_{21}H_{28}N_4O_2 \cdot 0.9\ H_2O$: C, 68.17; H, 7.67; N, 15.14. Found C, 67.84; H, 7.69; N, 14.99.

Example 10

2-Ethoxymethyl-1-[3-(2-methyl-[1,3]dioxolan-2-yl)propyl]-1H-imidazo[4,5-c]quinolin-4-amine

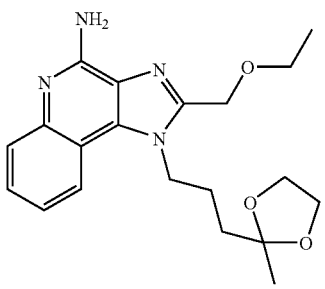 [SMILES: CCOCc1nc2c(N)nc3ccccc3c2n1CCCC1(C)OCCO1]

By utilizing ethoxyacetyl chloride (1.1 equivalents) and triethylamine (1.1 equivalents) instead of triethyl orthoacetate and pyridinium p-toluenesulfonate in Step 3 of Example 6, 2-ethoxymethyl-1-[3-(2-methyl-[1,3]dioxolan-2-yl)propyl]-1H-imidazo[4,5-c]quinolin-4-amine was prepared, mp 150-152° C.

MS (APCI) m/z 371 (M+H)$^+$;

Anal. calcd for $C_{20}H_{26}N_4O_3$: C, 64.84; H, 7.07; N, 15.12. Found: C, 64.65; H, 7.13; N, 15.01.

Example 11

5-(4-Amino-2-methyl-1H-imidazo[4,5-c]quinolin-1-yl)pentan-2-one

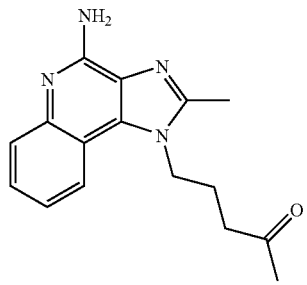 [SMILES: CC(=O)CCCn1c(C)nc2c(N)nc3ccccc3c21]

Concentrated hydrochloric acid (3 mL) was added to 2-methyl-1-[3-(2-methyl-[1,3]dioxolan-2-yl)propyl]-1H-imidazo[4,5-c]quinolin-4-amine (1.0 g, 2.7 mmol), and the mixture stirred for a few minutes until everything was in solution. Water (5 mL) was then added and the solution stirred for one hour at room temperature. After the addition of dichloromethane (75 mL) and water (25 mL), the solution was made basic by the slow addition of potassium carbonate (10.0 g). The layers were separated, and the organic layer was washed with a saturated aqueous sodium bicarbonate solution (25 mL), dried over potassium carbonate, filtered, and concentrated under reduced pressure to provide 5-(4-amino-2-methyl-1H-imidazo[4,5-c]quinolin-1-yl)pentan-2-one, mp 194-196° C.

MS (APCI) m/z 283 (M+H)$^+$;

Anal. calcd for $C_{16}H_{18}N_4O \cdot 0.44\ H_2O$: C, 66.20; H, 6.56; N, 19.30. Found: C, 66.23; H, 6.52; N, 19.35.

Examples 12, 13, 14 were prepared by the general method described above for Example 11 by acid-catalyzed hydrolysis of the appropriate ketal.

Example 12

5-(4-Amino-2-ethyl-1H-imidazo[4,5-c]quinolin-1-yl)pentan-2-one

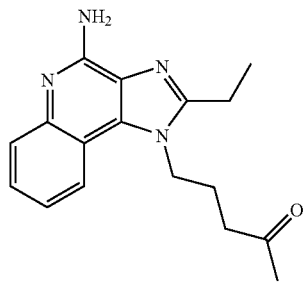 [SMILES: CCc1nc2c(N)nc3ccccc3c2n1CCCC(C)=O]

2-Ethyl-1-[3-(2-methyl-[1,3]dioxolan-2-yl)propyl]-1H-imidazo[4,5-c]quinolin-4-amine was hydrolyzed to 5-(4-amino-2-ethyl-1H-imidazo[4,5-c]quinolin-1-yl)pentan-2-one, mp 206-208° C.

MS (APCI) m/z=297 (M+H)$^+$;

Anal. calcd for $C_{17}H_{20}N_4O$: C, 68.90; H, 6.80; N, 18.9. Found C, 68.66; H, 6.84; N, 18.62.

Example 13

5-(4-Amino-2-propyl-1H-imidazo[4,5-c]quinolin-1-yl)pentan-2-one

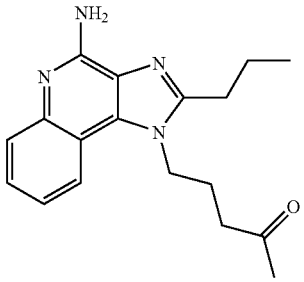 [SMILES: CCCc1nc2c(N)nc3ccccc3c2n1CCCC(C)=O]

1-[3-(2-Methyl-[1,3]dioxolan-2-yl)propyl]-2-propyl-1H-imidazo[4,5-c]quinolin-4-amine was hydrolyzed to 5-(4-amino-2-propyl-1H-imidazo[4,5-c]quinolin-1-yl)pentan-2-one, mp 176-177° C.

MS (APCI) m/z=311 (M+H)$^+$;

Anal. calcd for $C_{18}H_{22}N_4O \cdot 0.0125\ CH_2Cl_2$: C, 69.46; H, 7.13; N, 17.99. Found C, 69.12; H, 7.15; N, 17.71.

Example 14

5-(4-Amino-2-ethoxymethyl-1H-imidazo[4,5-c]quinolin-1-yl)pentan-2-one

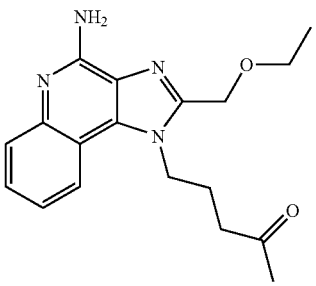 [SMILES: CCOCc1nc2c(N)nc3ccccc3c2n1CCCC(C)=O]

2-Ethoxymethyl-1-[3-(2-methyl-[1,3]dioxolan-2-yl)propyl]-1H-imidazo[4,5-c]quinolin-4-amine was hydrolyzed to 5-(4-amino-2-ethoxymethyl-1H-imidazo[4,5-c]quinolin-1-yl)pentan-2-one, mp 173-175° C.

MS (APCI) m/z 327 (M+H)$^+$;

Anal. calcd for $C_{18}H_{22}N_4O_2$: C, 66.24; H, 6.79; N, 17.17. Found: C, 66.05; H, 6.94; N, 16.89.

Example 15

7-(4-Amino-2-propyl-1H-imidazo[4,5-c]quinolin-1-yl)heptan-2-one

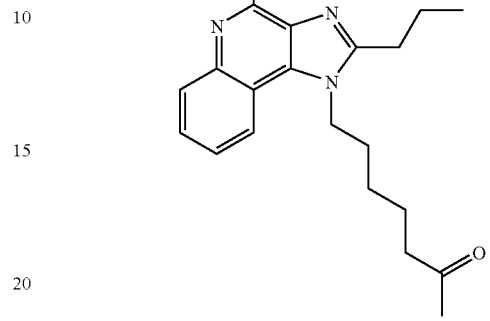

Step 1:

Ethyl 6-aminocaproate hydrochloride was prepared from 6-aminocaproic acid, thionyl chloride, and ethanol by the general method of C. Temple, Jr., R. D. Elliott, and J. A. Montgomery, *J. Med. Chem.*, 1988, 31, 697-700. The general method described in Step 1 of Example 1 was used to react 4-chloro-3-nitroquinoline (41.7 g, 200 mmol), ethyl 6-aminocaproate hydrochloride (46.9 g, 240 mmol) and triethylamine (50.6 g, 500 mmol) in dichloromethane for 15 hours to provide ethyl 6-(3-nitroquinolin-4-ylamino)hexanoate (60.6 g) as a yellow solid.

Step 2:

A Parr hydrogenation vessel was charged with ethyl 6-(3-nitroquinolin-4-ylamino)hexanoate (14.4 g, 43.2 mmol), 10% palladium on carbon catalyst (1.0 g), and ethanol (250 mL); placed on a Parr shaker; and the system pressurized to 40 psi ($2.7 \times 10^5$ Pa) hydrogen. After shaking for 15 hours, the reaction mixture was filtered through CELITE filter agent and concentrated under reduced pressure to provide ethyl 6-(3-aminoquinolin-4-ylamino)hexanoate as a dark oil (9.8 g) that was used directly in the next step without further purification. This step was repeated several times to provide material for the subsequent step.

Step 3:

A solution of ethyl 6-(3-aminoquinolin-4-ylamino)hexanoate (34.3 g, 114 mmol), trimethyl orthobutyrate (19.5 g, 131 mmol), and pyridinium p-toluenesulfonate (1.0 g, 4.0 mmol) in toluene (250 mL) was heated at reflux under a Dean-Stark trap for 5 hours, periodically draining off the distillate and adding fresh toluene to the reaction mixture. The solution was concentrated under reduced pressure, and the residue was taken up in dichloromethane (150 mL), washed successively with a saturated aqueous sodium bicarbonate solution and water (100 mL each), dried over potassium carbonate, filtered, and concentrated under reduced pressure to provide ethyl 6-(2-propyl-1H-imidazo[4,5-c]quinolin-1-yl)hexanoate (36.0 g) as a dark oil that was used directly in the next step without further purification.

Step 4:

To a solution of ethyl 6-(2-propyl-1H-imidazo[4,5-c]quinolin-1-yl)hexanoate (39.0 g, 110 mmol) in ethanol (100 mL) was added a solution of sodium hydroxide (5.73 g, 143 mmol) in water (100 mL). After stirring at room temperature overnight, the volatiles were removed under reduced pressure, the residue taken up in water (200 mL), the solution washed with dichloromethane (3×75 mL) and then acidified to about pH 6. The aqueous mixture was extracted with dichloromethane (3×75 mL), and then the combined organic fractions were dried over magnesium sulfate, filtered, and concentrated under reduced pressure to provide 6-(2-propyl-1H-imidazo[4,5-c]quinolin-1-yl)hexanoic acid (31.0 g) as a solid that was used directly in the next step without further purification.

Step 5:

To a solution of 6-(2-propyl-1H-imidazo[4,5-c]quinolin-1-yl)hexanoic acid (31.0 g, 95.3 mmol) in dichloromethane (200 mL) in an ice bath was added oxalyl chloride (21.9 g, 172 mmol) dropwise over a 30 minute period. The reaction mixture was then stirred for one hour at room temperature then concentrated under reduced pressure, and dichloromethane (400 mL) and N,O-dimethylhydroxylamine hydrochloride (18.6 g, 190 mmol) were added to the residue followed by the dropwise addition of triethylamine (38.5 g, 380 mmol). After stirring at room temperature overnight, the reaction mixture was washed successively with a saturated aqueous sodium bicarbonate solution and brine (100 mL each), dried over potassium carbonate, filtered, and concentrated under reduced pressure to provide N-methoxy-N-methyl-6-(2-propyl-1H-imidazo[4,5-c]quinolin-1-yl)hexanamide (28.0 g) as a dark oil that was used directly in the next step without further purification.

Step 6:

To a solution of N-methoxy-N-methyl-6-(2-propyl-1H-imidazo[4,5-c]quinolin-1-yl)hexanamide (22.0 g, 59.7 mmol) in chloroform (20 mL) and THF (200 mL) in an ice bath was added dropwise a solution of methylmagnesium bromide (40 mL of a 3 M solution in diethyl ether, 120 mmol). After 1 hour another charge of methylmagnesium bromide (40 mL of a 3 M solution in diethyl ether, 120 mmol) was added, the reaction mixture stirred at room temperature for 1 more hour and then quenched by the addition of a 10% solution of hydrochloric acid (about 10 mL). The mixture was concentrated under reduced pressure, the residue taken up in dichloromethane (200 mL), and the solution washed successively with a saturated aqueous sodium bicarbonate solution and brine (100 mL each), dried over potassium carbonate, and filtered. The solution was concentrated under reduced pressure and chromatographed on silica gel (elution with 3% methanol in dichloromethane) to provide 7-(2-propyl-1H-imidazo[4,5-c]quinolin-1-yl)heptan-2-one (12.6 g) as an oil that was used directly in the next step without further purification.

Step 7:

The general method described in Steps 9 and 10 of Example 1 was used to aminate 7-(2-propyl-1H-imidazo[4,5-c]quinolin-1-yl)heptan-2-one (5.0 g, 15.5 mmol) by reaction with m-CPBA (8.0 g) to provide 7-(5-oxido-2-propyl-1H-imidazo[4,5-c]quinolin-1-yl)heptan-2-one followed by reaction with p-toluenesulfonyl chloride (4.42 g, 23.2 mmol) and ammonium hydroxide solution (50 mL) to provide 7-(4-amino-2-propyl-1H-imidazo[4,5-c]quinolin-1-yl)heptan-2-one) as an off-white solid after recrystallization from a mixture of acetonitrile, ethyl acetate, and hexane, mp 161-163° C.

MS (APCI) m/z=339 (M+H)$^+$;

Anal. calcd for $C_{20}H_{26}N_4O$: C, 70.98; H, 7.74; N, 16.55. Found C, 70.62; H, 7.91; N, 16.37.

Example 16

12-(4-Amino-2-propyl-1H-imidazo[4,5-c]quinolin-1-yl)-1-phenyldodecan-1-one hydrochloride

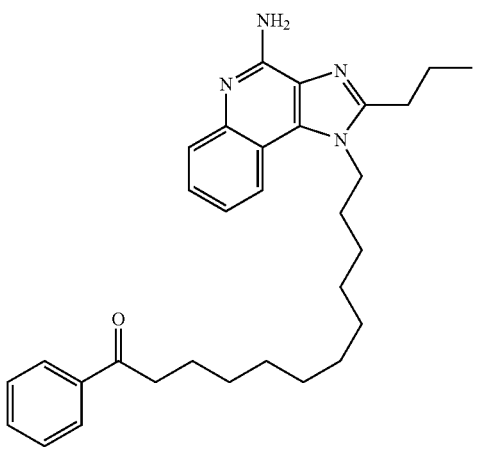 [SMILES: CCCc1nc2c(N)nc3ccccc3c2n1CCCCCCCCCCCC(=O)c1ccccc1]

Step 1:

Ethyl 12-aminododecanoate hydrochloride was prepared from 12-aminododecanoic acid, thionyl chloride, and ethanol by the general method of C. Temple, Jr., R. D. Elliott, and J. A. Montgomery, *J. Med. Chem.*, 1988, 31, 697-700. The general method described in Step 1 of Example 15 was used to react 4-chloro-3-nitroquinoline (15.5 g, 74.4 mmol), ethyl 12-aminododecanoate hydrochloride (25.0 g, 89.3 mmol), and triethylamine (18.8 g, 186 mmol) in dichloromethane for 15 hours to provide ethyl 12-(3-nitroquinolin-4-ylamino) dodecanoate (30.0 g) as a yellow solid that was used directly in the next step without further purification.

Step 2:

The general method described in Step 2 of Example 15 was used to reduce ethyl 12-(3-nitroquinolin-4-ylamino)dodecanoate (30.0 g, 77.0 mmol) to provide ethyl 12-(3-aminoquinolin-4-ylamino)dodecanoate (30.4 g) as a solid that was used directly in the next step without further purification.

Step 3:

The general method described in Step 3 of Example 15 was used to cyclize ethyl 12-(3-aminoquinolin-4-ylamino)dodecanoate (30.4 g, 78.8 mmol) by reaction with trimethyl orthobutyrate (13.4 g, 90.6 mmol) to provide ethyl 12-(2-propyl-1H-imidazo[4,5-c]quinolin-1-yl)dodecanoate (32.1 g) as a solid that was used directly in the next step without further purification.

Steps 4 and 5:

The general method described in Step 4 of Example 15 was used to provide 12-(2-propyl-1H-imidazo[4,5-c]quinolin-1-yl)dodecanoic acid (33.6 g) which was converted to N-methoxy-N-methyl-12-(2-propyl-1H-imidazo[4,5-c]quinolin-1-yl)dodecanamide (36.8 g) by the general method described in Step 5 of Example 15.

Step 6:

The general method described in Step 6 of Example 15 was used to react N-methoxy-N-methyl-12-(2-propyl-1H-imidazo[4,5-c]quinolin-1-yl)dodecanamide (6.0 g, 13.3 mmol) with phenylmagnesium bromide (26.5 mmol, 26.5 mL of a 1 M solution in THF) to provide 1-phenyl-12-(2-propyl-1H-imidazo[4,5-c]quinolin-1-yl)dodecan-1-one (6.0 g).

Step 7:

The general method described in Steps 9 and 10 of Example 1 was used to aminate 1-phenyl-12-(2-propyl-1H-imidazo[4,5-c]quinolin-1-yl)dodecan-1-one (6.0 g, 12.8 mmol) by reaction with m-CPBA (8.18 g) to provide 12-(5-oxido-2-propyl-1H-imidazo[4,5-c]quinolin-1-yl)-1-phenyl-dodecan-1-one followed by reaction with p-toluenesulfonyl chloride (3.65 g, 19.2 mmol) and ammonium hydroxide solution (40 mL). The product was dissolved a mixture of ethanol and diethyl ether, and a solution of hydrogen chloride (1 equivalent of a 1.0 M solution in diethyl ether) was added. A precipitate formed, and the solvents were removed under reduced pressure. The resulting solid was recrystallized from a mixture of isopropanol and hexane to provide 12-(4-amino-2-propyl-1H-imidazo[4,5-c]quinolin-1-yl)-1-phenyldodecan-1-one hydrochloride as an off-white solid, mp 195-196° C.

MS (APCI) m/z=485 (M+H)$^+$;

Anal. calcd for $C_{31}H_{40}N_4O \cdot 1.20\ HCl \cdot 0.17\ H_2O$: C, 70.05; H, 7.87; N, 10.52. Found C, 69.97; H, 7.70; N, 10.46.

Example 17

1-(4-Amino-2-propyl-1H-imidazo[4,5-c]quinolin-1-yl)-6-methylheptan-4-one

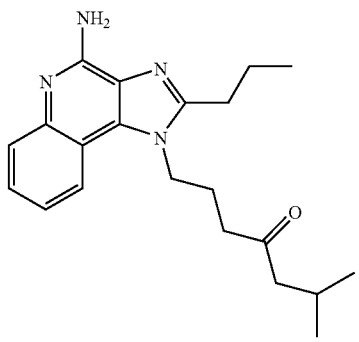 [SMILES: CCCc1nc2c(N)nc3ccccc3c2n1CCCC(=O)CC(C)C]

Step 1:

The general method described in Step 1 of Example 15 was used to react 4-chloro-3-nitroquinoline (49.6 g, 238 mmol), ethyl 4-aminobutyrate hydrochloride (43.8 g, 262 mmol), and triethylamine (36.1 g, 357 mmol) in dichloromethane for 15 hours to provide ethyl 4-(3-nitroquinolin-4-ylamino)butyrate (63.8 g) as a yellow solid that was used directly in the next step without further purification.

Step 2:

The general method described in Step 2 of Example 6 was used to reduce ethyl 4-(3-nitroquinolin-4-ylamino)butyrate (37.0 g, 122 mmol) to provide ethyl 4-(3-aminoquinolin-4-ylamino)butyrate (24.9 g) as a dark oil that was used directly in the next step without further purification.

Step 3:

The general method described in Step 3 of Example 15 was used to cyclize ethyl 4-(3-aminoquinolin-4-ylamino)butyrate (18.0 g, 65.9 mmol) by reaction with trimethyl orthobutyrate (10.4 g, 70.2 mmol) to provide ethyl 4-(2-propyl-1H-imidazo[4,5-c]quinolin-1-yl)butyrate (14.2 g) as a solid after chromatography on silica gel (elution with 5% methanol in dichloromethane).

Step 4:

A solution of trimethylaluminum in toluene (80 mL of a 2 M solution, 160 mmol) was added dropwise to a stirred suspension of N,O-dimethylhydroxylamine hydrochloride (15.6 g, 160 mmol) in dichloromethane (150 mL) at 0° C. After 15 minutes, the reaction flask was removed from bath and the solution stirred for 15 minutes at room temperature. The flask was then cooled in ice bath, and a solution of ethyl 4-(2-propyl-1H-imidazo[4,5-c]quinolin-1-yl)butyrate (34.7 g, 107 mmol) in dichloromethane (100 mL) was added rapidly dropwise. After 15 minutes, the ice bath was removed and the solution heated at reflux to cause considerable gas evolution. After 20 hours, a 10% solution of hydrochloric acid in water (15 mL) was added slowly, followed by a saturated solution of sodium bicarbonate in water (50 mL). The layers were separated, and the aqueous mixture was extracted with dichloromethane (2×50 mL). The combined organic solutions were washed successively with a 5% solution of sodium hydroxide in water (2×50 mL) and a saturated solution of sodium bicarbonate in water (1×50 mL), dried over potassium carbonate, filtered, and concentrated under reduced pressure to provide N-methoxy-N-methyl-4-(2-propyl-1H-imidazo[4,5-c]quinolin-1-yl)butyramide (35.9 g) as a dark oil that was used directly in the next step without further purification.

Step 5:

To a stirred solution of N-methoxy-N-methyl-4-(2-propyl-1H-imidazo[4,5-c]quinolin-1-yl)butyramide (4.80 g, 14.1 mmol) in THF (100 mL) in a dry ice/isopropanol bath was added a solution of isobutylmagnesium chloride (28 mL of a 2 M solution in diethyl ether, 56 mmol) over a period of several minutes. When addition was complete, the reaction flask was removed from the cold bath and the mixture stirred for 4 hours at room temperature. A 10% solution of hydrochloric acid in water (3 mL) was added slowly, followed by a saturated solution of sodium bicarbonate in water (15 mL) and dichloromethane (100 mL). The layers were separated, the aqueous phase extracted with dichloromethane (1×75 mL), and the combined organics dried over potassium carbonate, filtered, and concentrated under reduced pressure. After chromatography on silica gel (elution with 5% methanol in dichloromethane) 6-methyl-1-(2-propyl-1H-imidazo[4,5-c]quinolin-1-yl)heptan-4-one (2.40 g) was obtained as an oil.

Step 6:

The general method described in Steps 9 and 10 of Example 1 was used to aminate 6-methyl-1-(2-propyl-1H-imidazo[4,5-c]quinolin-1-yl)heptan-4-one (2.40 g, 7.10 mmol) by reaction with m-CPBA (3.9 g) to provide 6-methyl-1-(5-oxido-2-propyl-1H-imidazo[4,5-c]quinolin-1-yl)heptan-4-one followed by reaction with p-toluenesulfonyl chloride (2.0 g, 10.5 mmol) and ammonium hydroxide solution (75 mL) to provide 1-(4-amino-2-propyl-1H-imidazo[4,5-c]quinolin-1-yl)-6-methylheptan-4-one as tan crystals after recrystallization from aqueous methanol, mp 136-138° C.

MS (APCI) m/z 353 (M+H)$^+$;

Anal. calcd for $C_{21}H_{28}N_4O$: C, 71.56; H, 8.01; N, 15.90. Found: C, 71.33; H, 8.09; N, 15.69.

Example 18

1-(4-Amino-2-propyl-1H-imidazo[4,5-c]quinolin-1-yl)decan-4-one

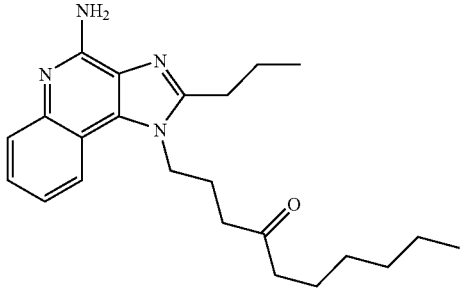 [SMILES: CCCCCCC(=O)CCCn1c(CCC)nc2c(N)nc3ccccc3c21]

Steps 1 through 4:
The general method described in Steps 1 through 4 of Example 17 was used to prepare N-methoxy-N-methyl-4-(2-propyl-1H-imidazo[4,5-c]quinolin-1-yl)butyramide.

Step 5:
The general method described in Step 5 of Example 17 was used to react N-methoxy-N-methyl-4-(2-propyl-1H-imidazo[4,5-c]quinolin-1-yl)butyramide (6.10 g, 17.9 mmol) with n-hexylmagnesium bromide (13.5 mL of a 2 M solution in diethyl ether, 27 mmol) to provide 1-(2-propyl-1H-imidazo[4,5-c]quinolin-1-yl)decan-4-one (6.10 g) as a yellow oil that was used directly in the next step without further purification.

Step 6:
The general method described in Steps 9 and 10 of Example 1 was used to aminate 1-(2-propyl-1H-imidazo[4,5-c]quinolin-1-yl)decan-4-one (6.10 g, 17.2 mmol) by reaction with m-CPBA (8.50 g) to provide 1-(5-oxido-2-propyl-1H-imidazo[4,5-c]quinolin-1-yl)decan-4-one followed by reaction with p-toluenesulfonyl chloride (4.90 g, 25.8 mmol) and ammonium hydroxide solution (100 mL) to provide 1-(4-amino-2-propyl-1H-imidazo[4,5-c]quinolin-1-yl)decan-4-one) as a white solid after recrystallization from aqueous methanol, mp 111-113° C.

MS (APCI) m/z 381 (M+H)$^+$;

Anal. calcd for $C_{23}H_{32}N_4O$: C, 72.59; H, 8.48; N, 14.72. Found: C, 72.53; H, 8.59; N, 14.63.

Example 19

6-(4-Amino-2-propyl-1H-imidazo[4,5-c]quinolin-1-yl)-N-methoxy-N-methylhexanamide

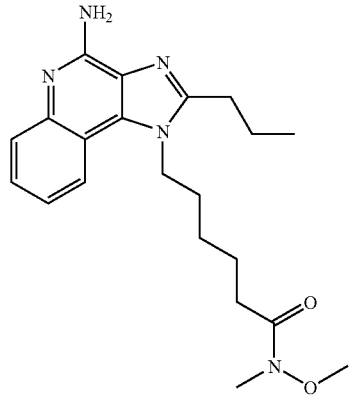 [SMILES: CCCc1nc2c(N)nc3ccccc3c2n1CCCCCC(=O)N(C)OC]

Steps 1 through 5:
The method described in Steps 1 through 5 of Example 15 was used to prepare N-methoxy-N-methyl-6-(2-propyl-1H-imidazo[4,5-c]quinolin-1-yl)hexanamide.

Step 6:
The general method described in Steps 9 and 10 of Example 1 was used to aminate N-methoxy-N-methyl-6-(2-propyl-1H-imidazo[4,5-c]quinolin-1-yl)hexanamide (4.01 g, 10.9 mmol) by reaction with m-CPBA (6.13 g) to provide N-methoxy-N-methyl-6-(5-oxido-2-propyl-1H-imidazo[4,5-c]quinolin-1-yl)hexanamide followed by reaction with p-toluenesulfonyl chloride (2.53 g, 13.3 mmol) and ammonium hydroxide solution (40 mL) to provide 6-(4-amino-2-propyl-1H-imidazo[4,5-c]quinolin-1-yl)-N-methoxy-N-methylhexanamide) as an off-white solid after recrystallization from a mixture of ethyl acetate and hexane, mp 134-135° C.

MS (APCI) m/z=384 (M+H)$^+$;

Anal. calcd for $C_{21}H_{29}N_5O_2 \cdot 0.023\ C_4H_8O_2$: C, 65.71; H, 7.63; N, 18.17. Found C, 65.44; H, 7.77; N, 17.88.

Example 20

4-(4-Amino-2-propyl-1H-imidazo[4,5-c]quinolin-1-yl)-N-methoxy-N-methylbutyramide

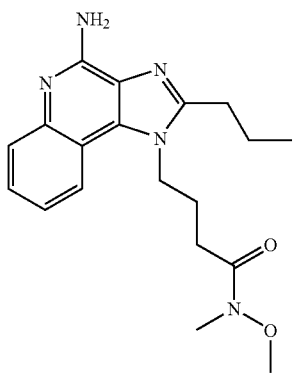 [SMILES: CCCc1nc2c(N)nc3ccccc3c2n1CCCC(=O)N(C)OC]

Steps 1 through 4:
The method of Steps 1 through 4 of Example 17 was used to prepare N-methoxy-N-methyl-4-(2-propyl-1H-imidazo[4,5-c]quinolin-1-yl)butyramide.

Step 5:
The general method described in Steps 9 and 10 of Example 1 was used to aminate N-methoxy-N-methyl-4-(2-propyl-1H-imidazo[4,5-c]quinolin-1-yl)butyramide (7.4 g, 21.7 mmol) by reaction with m-CPBA (9.50 g) to provide N-methoxy-N-methyl-4-(5-oxido-2-propyl-1H-imidazo[4,5-c]quinolin-1-yl)butyramide followed by reaction with p-toluenesulfonyl chloride (7.20 g, 37.8 mmol) and ammonium hydroxide solution (200 mL) to provide 4-(4-amino-2-propyl-1H-imidazo[4,5-c]quinolin-1-yl)-N-methoxy-N-methyl-butyramide as white crystals after recrystallization from aqueous methanol, mp 163-165° C.

MS (APCI) m/z 356 (M+H)$^+$;

Anal. calcd for $C_{19}H_{25}N_5O_2$: C, 64.20; H, 7.09; N, 19.70. Found: C, 64.10; H, 6.91; N, 19.57.

Example 21

12-(4-Amino-2-propyl-1H-imidazo[4,5-c]quinolin-1-yl)-N-methoxy-N-methyldodecanamide hydrochloride

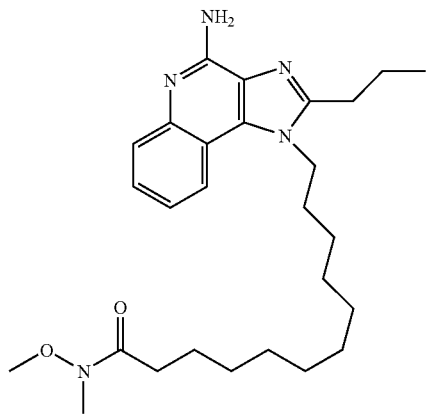 [SMILES: CCCc1nc2c(N)nc3ccccc3c2n1CCCCCCCCCCCC(=O)N(C)OC]

Steps 1 through 5:

The method of Steps 1 through 5 of Example 16 was used to prepare N-methoxy-N-methyl-12-(2-propyl-1H-imidazo[4,5-c]quinolin-1-yl)dodecanamide.

Step 6:

The general methods described in Steps 9 and 10 of Example 1 and Step 7 of Example 16 was used to aminate N-methoxy-N-methyl-12-(2-propyl-1H-imidazo[4,5-c]quinolin-1-yl)dodecanamide (4.01 g, 8.86 mmol) by reaction with m-CPBA (6.13 g) to provide N-methoxy-N-methyl-12-(5-oxido-2-propyl-1H-imidazo[4,5-c]quinolin-1-yl)dodecanamide followed by reaction with p-toluenesulfonyl chloride (2.53 g, 13.3 mmol) and ammonium hydroxide solution (40 mL) to provide 2-(4-amino-2-propyl-1H-imidazo[4,5-c]quinolin-1-yl)-N-methoxy-N-methyldodecanamide hydrochloride as an off-white solid after recrystallization of the hydrochloride salt from isopropanol, mp 156-158° C.

MS (APCI) m/z=468 (M+H)$^+$;

Anal. calcd for $C_{27}H_{41}N_5O_2 \cdot 1.20$ HCl: C, 63.41; H, 8.31; N, 13.69. Found C, 63.44; H, 8.24; N, 13.74.

Example 22

1-[2,2-Dimethyl-3-(2-methyl-[1,3]dioxolan-2-yl)propyl]-2-methyl-1H-imidazo[4,5-c]quinolin-4-amine

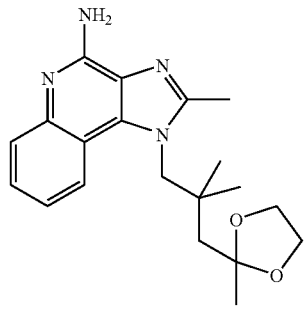 [SMILES: Cc1nc2c(N)nc3ccccc3c2n1CC(C)(C)CC1(C)OCCO1]

Step 1:

A mixture of nitromethane (36.3 g, 0.59 mol), mesityl oxide (53.0 g, 0.54 mol), and 1,5-diazabicyclo[5.4.0]undec7-ene (DBU, 1.5 g, 10 mmol) was allowed to stand at room temperature for 14 days. Dichloromethane (150 mL) was then added, and the solution was washed with a 10% hydrochloric acid solution (3×35 mL), dried over potassium carbonate, and filtered. The dichloromethane solution of 4,4-dimethyl-5-nitropentan-2-one was used directly in the next step without further purification.

Step 2:

A stirred solution of 1,2-bis(trirethylsilyloxy)ethane (26.5 g, 128 mmol) in dichloromethane (50 mL) was cooled in a dry ice/isopropanol bath, and trimethylsilyl trifluoromethanesulfonate (2.2 g, 1.0 mmol) was added, followed by the dichloromethane solution of 4,4-dimethyl-5-nitropentan-2-one (50 mL, 19.0 g, 119 mmol) from the previous step. After 30 minutes, the cooling bath was removed and the solution was allowed to warm to room temperature. The solution was filtered through a plug of potassium carbonate and concentrated under reduced pressure to provide 2-(2,2-dimethyl-3-nitropropyl)-2-methyl-[1,3]dioxolane (23.5 g) as a dark oil that was used directly in the next step without further purification.

Step 3:

A Parr hydrogenation vessel was charged with 2-(2,2-dimethyl-3-nitropropyl)-2-methyl-[1,3]dioxolane (23.1 g, 113 mmol), 5% platinum on carbon catalyst (3.0 g) and ethanol (250 mL); placed on a Parr shaker; and the system pressurized to 50 psi ($3.4 \times 10^5$ Pa) hydrogen. After shaking for 24 hours, the reaction mixture was filtered through CELITE filter agent and concentrated under reduced pressure to provide 2,2-dimethyl-3-(2-methyl-[1,3]dioxolan-2-yl)propylamine (19.8 g) as an oil that was used directly in the next step without further purification.

Step 4:

The general method described in Step 1 of Example 1 was used to react 4-chloro-3-nitroquinoline (21.8 g, 104 mmol), 2,2-dimethyl-3-(2-methyl-[1,3]dioxolan-2-yl)propylamine (19.8 g, 114 mmol) and triethylamine (15.2 g, 150 mmol) in dichloromethane for 75 hours to provide [2,2-dimethyl-3-(2-methyl-[1,3]dioxolan-2-yl)propyl]-(3-nitroquinolin-4-yl)amine (35.9 g) as a yellow solid that was used directly in the next step without further purification.

Step 5:

The general method described in Step 2 of Example 6 was used to reduce [2,2-dimethyl-3-(2-methyl-[1,3]dioxolan-2-yl)propyl]-(3-nitroquinolin-4-yl)amine (35.9 g, 104 mmol) to provide $N^4$-[2,2-dimethyl-3-(2-methyl-[1,3]dioxolan-2-yl)propyl]quinoline-3,4-diamine (25.2 g) as a dark oil that was used directly in the next step without further purification.

Step 6:

The general method described in Step 3 of Example 6 was used to cyclize $N^4$-[2,2-dimethyl-3-(2-methyl-[1,3]dioxolan-2-yl)propyl]quinoline-3,4-diamine (8.0 g, 25.4 mmol) by reaction with trimethyl orthoacetate (3.6 g, 30 mmol) to provide 1-[2,2-dimethyl-3-(2-methyl-[1,3]dioxolan-2-yl)propyl]-2-methyl-1H-imidazo[4,5-c]quinoline (5.80 g) as a solid after chromatography on silica gel (elution with a solution of 7% methanol in dichloromethane that contained about 5 mL of ammonium hydroxide solution per liter of eluent).

Step 7:

The general method described in Steps 9 and 10 of Example 1 was used to aminate 1-[2,2-dimethyl-3-(2-methyl-[1,3]dioxolan-2-yl)propyl]-2-methyl-1H-imidazo[4,5-c]quinoline (5.80 g, 17.1 mmol) by reaction with m-CPBA (7.5 g) to provide 1-[2,2-dimethyl-3-(2-methyl-[1,3]dioxolan-2-yl)propyl]-2-methyl-5-oxido-1H-imidazo[4,5-c]

quinoline followed by reaction with p-toluenesulfonyl chloride (5.7 g, 30 mmol) and ammonium hydroxide solution (150 mL) to provide 1-[2,2-dimethyl-3-(2-methyl-[1,3]dioxolan-2-yl)propyl]-2-methyl-1H-imidazo[4,5-c]quinolin-4-amine as a light brown solid after recrystallization from a mixture of acetonitrile, methanol, and water, mp 209-211° C.

MS (APCI) m/z 355 (M+H)$^+$;

Anal. calcd for $C_{20}H_{26}N_4O_2$: C, 67.77; H, 7.39; N, 15.81. Found: C, 67.68; H, 7.62; N, 15.87.

Example 23

1-[2,2-Dimethyl-3-(2-methyl-[1,3]dioxolan-2-yl)propyl]-2-propyl-1H-imidazo[4,5-c]quinolin-4-amine

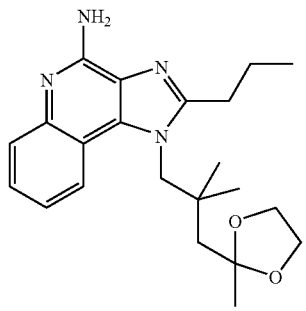 [SMILES: CCCc1nc2c(N)nc3ccccc3c2n1CC(C)(C)CC1(C)OCCO1]

Steps 1-5 were the same as described for Example 22.

Step 6:

The general method described in Step 6 of Example 22 was used to cyclize $N^4$-[2,2-dimethyl-3-(2-methyl-[1,3]dioxolan-2-yl)propyl]quinoline-3,4-diamine (9.1 g, 28.9 mmol) by reaction with trimethyl orthobutyrate (4.4 g, 30 mmol) to provide 1-[2,2-dimethyl-3-(2-methyl-[1,3]dioxolan-2-yl)propyl]-2-propyl-1H-imidazo[4,5-c]quinoline (3.10 g) as a solid after chromatography on silica gel (elution with a solution of 7% methanol in dichloromethane that contained about 5 mL of ammonium hydroxide solution per liter of eluent).

Step 7:

The general method described in Steps 9 and 10 of Example 1 was used to aminate 1-[2,2-dimethyl-3-(2-methyl-[1,3]dioxolan-2-yl)propyl]-2-propyl-1H-imidazo[4,5-c]quinoline (3.10 g, 8.44 mmol) by reaction with m-CPBA (3.70 g) to provide 1-[2,2-dimethyl-3-(2-methyl-[1,3]dioxolan-2-yl)propyl]-5-oxido-2-propyl-1H-imidazo[4,5-c]quinoline followed by reaction with p-toluenesulfonyl chloride (2.80 g, 14.7 mmol) and ammonium hydroxide solution (100 mL) to provide 1-[2,2-dimethyl-3-(2-methyl-[1,3]dioxolan-2-yl)propyl]-2-propyl-1H-imidazo[4,5-c]quinolin-4-amine as off-white needles after recrystallization from aqueous methanol, mp 186-188° C.

MS (APCI) m/z 383 (M+H)$^+$;

Anal. calcd for $C_{22}H_{30}N_4O_2$: C, 69.08; H, 7.91; N, 14.65. Found: C, 69.03; H, 8.15; N, 14.60.

Example 24

5-(4-Amino-2-methyl-1H-imidazo[4,5-c]quinolin-1-yl)-4,4-dimethylpentan-2-one

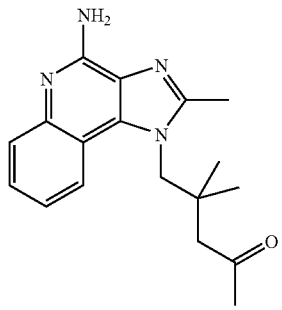 [SMILES: CC(=O)CC(C)(C)Cn1c(C)nc2c(N)nc3ccccc3c21]

By the general method of Example 11, 1-[2,2-dimethyl-3-(2-methyl-[1,3]dioxolan-2-yl)propyl]-2-methyl-1H-imidazo[4,5-c]quinolin-4-amine was hydrolyzed with aqueous hydrochloric acid to provide 5-(4-amino-2-methyl-1H-imidazo[4,5-c]quinolin-1-yl)-4,4-dimethylpentan-2-one as a light brown solid after recrystallization from aqueous acetonitrile, mp 223-225° C.

MS (APCI) m/z 311 (M+H)$^+$;

Anal. calcd for $C_{18}H_{22}N_4O$: C, 69.65; H, 7.14; N, 18.05. Found: C, 69.64; H, 7.42; N, 18.04.

Example 25

5-(4-Amino-2-propyl-1H-imidazo[4,5-c]quinolin-1-yl)-4,4-dimethylpentan-2-one

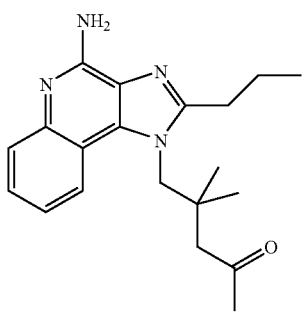 [SMILES: CCCc1nc2c(N)nc3ccccc3c2n1CC(C)(C)CC(C)=O]

By the general method of Example 11, 1-[2,2-dimethyl-3-(2-methyl-[1,3]dioxolan-2-yl)propyl]-2-propyl-1H-imidazo[4,5-c]quinolin-4-amine was hydrolyzed with aqueous hydrochloric acid to provide 5-(4-amino-2-propyl-1H-imidazo[4,5-c]quinolin-1-yl)-4,4-dimethylpentan-2-one as a light brown solid after recrystallization from aqueous acetonitrile, mp 178-180° C.

MS (APCI) m/z 339 (M+H)$^+$;

Anal. calcd for $C_{20}H_{26}N_4O$: C, 70.97; H, 7.74; N, 16.55. Found: C, 70.80; H, 7.89; N, 16.66.

Example 26

Ethyl 3-(4-amino-2-propyl-1H-imidazo[4,5-c]quinolin-1-yl)propionate

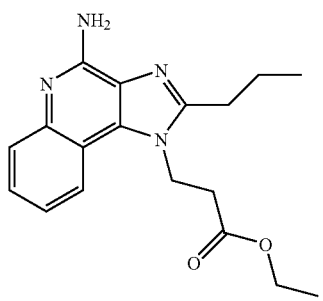 [SMILES: CCCc1nc2c(N)nc3ccccc3c2n1CCC(=O)OCC]

Step 1:

The general method described in Step 1 of Example 1 was used to react 4-chloro-3-nitroquinoline (45.3 g, 217 mmol), β-alanine ethyl ester hydrochloride (40.0 g, 240 mmol), and triethylamine (54.8 g, 542 mmol) in dichloromethane for 15 hours to provide ethyl 3-(3-nitroquinolin-4-ylamino)propionate (62.0 g) as a yellow solid.

Step 2:

The general method described in Step 2 of Example 6 was used to reduce ethyl 3-(3-nitroquinolin-4-ylamino)propionate to provide ethyl 3-(3-aminoquinolin-4-ylamino)propionate (40.2 g) as a dark oil that was used directly in the next step without further purification.

Step 3:

The general method described in Step 3 of Example 15 was used to cyclize ethyl 3-(3-aminoquinolin-4-ylamino)propionate (11.0 g, 42.4 mmol) by reaction with trimethyl orthobutyrate (7.22 g, 48.7 mmol) to provide ethyl 3-(2-propyl-1H-imidazo[4,5-c]quinolin-1-yl)propionate (10.6 g) as a dark oil that was used directly in the next step without further purification.

Step 4:

The general method described in Steps 9 and 10 of Example 1 was used to aminate ethyl 3-(2-propyl-1H-imidazo[4,5-c]quinolin-1-yl)propionate (3.30 g, 10.6 mmol) by reaction with m-CPBA (4.63 g) to provide ethyl 3-(5-oxido-2-propyl-1H-imidazo[4,5-c]quinolin-1-yl)propionate followed by reaction with p-toluenesulfonyl chloride (3.53 g, 18.6 mmol) and ammonium hydroxide solution (50 mL) to provide ethyl 3-(4-amino-2-propyl-1H-imidazo[4,5-c]quinolin-1-yl)propionate as an off-white solid after recrystallization from aqueous methanol, mp 156-157° C.

MS (APCI) m/z=327 (M+H)$^+$;

Anal. calcd for $C_{18}H_{22}N_4O_2$: C, 66.24; H, 6.79; N, 17.16. Found C, 65.98; H, 6.96; N, 17.29.

Example 27

Ethyl 4-(4-amino-2-propyl-1H-imidazo[4,5-c]quinolin-1-yl)butyrate

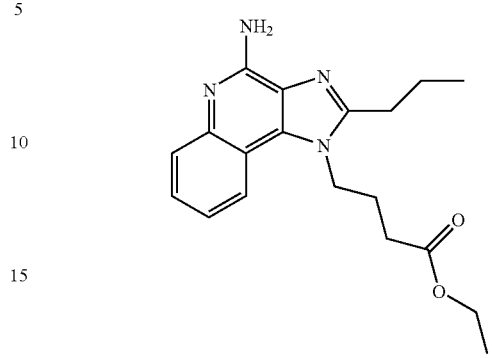

The general method described in Steps 9 and 10 of Example 1 was used to aminate ethyl 4-(2-propyl-1H-imidazo[4,5-c]quinolin-1-yl)butyrate (8.20 g, 25.2 mmol, available from Step 3 of Example 17) by reaction with m-CPBA (14.1 g) to provide ethyl 4-(5-oxido-2-propyl-1H-imidazo[4,5-c]quinolin-1-yl)butyrate followed by reaction with p-toluenesulfonyl chloride (8.40 g, 44.1 mmol) and ammonium hydroxide solution (150 mL) to provide ethyl 4-(4-amino-2-propyl-1H-imidazo[4,5-c]quinolin-1-yl)butyrate as an off-white solid after recrystallization from aqueous methanol, mp 154-156° C.

MS (APCI) m/z=341 (M+H)$^+$;

Anal. calcd for $C_{19}H_{24}N_4O_2$: C, 67.04; H, 7.1 1; N, 16.46. Found C, 66.68; H, 6.87; N, 16.51.

Example 28

Ethyl 6-(4-amino-2-propyl-1H-imidazo[4,5-c]quinolin-1-yl)hexanoate

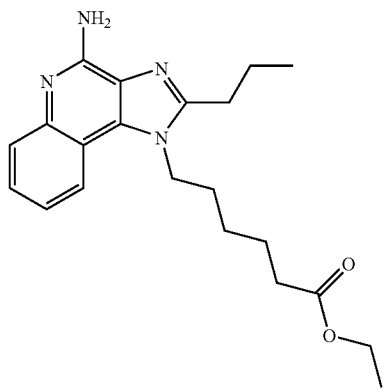 [SMILES: CCCc1nc2c(N)nc3ccccc3c2n1CCCCCC(=O)OCC]

The general method described in Steps 9 and 10 of Example 1 was used to aminate ethyl 6-(2-propyl-1H-imidazo[4,5-c]quinolin-1-yl)hexanoate (6.30 g, 17.8 mmol, available from Step 3 of Example 15) by reaction with m-CPBA (13.1 g) to provide ethyl 6-(5-oxido-2-propyl-1H-imidazo[4,5-c]quinolin-1-yl)hexanoate followed by reaction with p-toluenesulfonyl chloride (4.58 g, 24.0 mmol) and ammonium hydroxide solution (60 mL) to provide ethyl 6-(4-amino-2-propyl-1H-imidazo[4,5-c]quinolin-1-yl)hexanoate as a tan solid after recrystallization from aqueous methanol, mp 112-113° C.

MS (APCI) m/z=369 (M+H)$^+$;

Anal. calcd for $C_{21}H_{28}N_4O_2 \cdot 1.0\ H_2O$: C, 67.77; H, 7.69; N, 15.05. Found C, 67.39; H, 7.73; N, 14.79.

Example 29

1-(2,2-Diethoxyethyl)-2-propyl-1H-imidazo[4,5-c]quinolin-4-amine

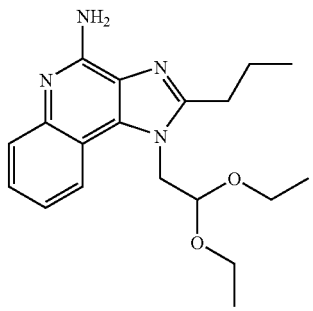 [SMILES: CCCc1nc2c(N)nc3ccccc3c2n1CC(OCC)OCC]

Step 1:

The general method described in Step 1 of Example 1 was used to react 4-chloro-3-nitroquinoline (20.9 g, 100 mmol), aminoacetaldehyde diethyl acetal (14.4 g, 110 mmol), and triethylamine (12.6 g, 125 mmol) in dichloromethane for 15 hours to provide (2,2-diethoxyethyl)-(3-nitroquinolin-4-yl)amine (29.7 g) as a yellow solid.

Step 2:

The general method described in Step 2 of Example 6 was used to reduce (2,2-diethoxyethyl)-(3-nitroquinolin-4-yl)amine to provide N-(2,2-diethoxyethyl)quinoline-3,4-diamine (26.5 g) as a dark oil that was used directly in the next step without further purification.

Step 3:

The general method described in Step 3 of Example 15 was used to cyclize $N^4$-(2,2-diethoxyethyl)quinoline-3,4-diamine (26.5 g, 96.2 mmol) by reaction with trimethyl orthobutyrate (15.9 g, 107 mmol) to provide 1-(2,2-diethoxyethyl)-2-propyl-1H-imidazo[4,5-c]quinoline (25.4 g) as a dark oil that was used directly in the next step without further purification.

Step 4:

The general method described in Steps 9 and 10 of Example 1 was used to aminate 1-(2,2-diethoxyethyl)-2-propyl-1H-imidazo[4,5-c]quinoline (4.50 g, 13.7 mmol) by reaction with m-CPBA (6.0 g) to provide 1-(2,2-diethoxyethyl)-5-oxido-2-propyl-1H-imidazo[4,5-c]quinoline followed by reaction with p-toluenesulfonyl chloride (4.60 g, 24.1 mmol) and ammonium hydroxide solution (130 mL) to provide 1-(2,2-diethoxyethyl)-2-propyl-1H-imidazo[4,5-c]quinolin-4-amine as an off-white solid after recrystallization from aqueous methanol, mp 148-150° C.

MS (APCI) m/z=343 (M+H)$^+$;

Anal. calcd for $C_{19}H_{26}N_4O_2$: C, 66.64; H, 7.65; N, 16.36. Found C, 66.62; H, 7.80; N, 16.43

Example 30

1-(3,3-Diethoxypropyl)-2-propyl-1H-imidazo[4,5-c]quinolin-4-amine

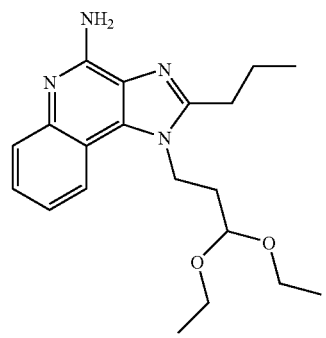 [SMILES: CCCc1nc2c(N)nc3ccccc3c2n1CCC(OCC)OCC]

Step 1:

The general method described in Step 1 of Example 1 was used to react 4-chloro-3-nitroquinoline (20.3 g, 97.1 mmol), 1-amino-3,3-diethoxypropane (25.0 g, 116 mmol) and triethylamine (33.8 g, 333 mmol) in dichloromethane for 15 hours to provide (3,3-diethoxypropyl)-(3-nitroquinolin-4-yl)amine (30.5 g) as a yellow solid.

Step 2:

The general method described in Step 2 of Example 6 was used to reduce (3,3-diethoxypropyl)-(3-nitroquinolin-4-yl)amine to provide $N^4$-(3,3-diethoxypropyl)quinoline-3,4-diamine (20.7 g) as a dark oil that was used directly in the next step without further purification.

Step 3:

The general method described in Step 3 of Example 15 was used to cyclize $N^4$-(3,3-diethoxypropyl)quinoline-3,4-diamine (20.7 g, 71.5 mmol) by reaction with trimethyl orthobutyrate (13.2 g, 89.4 mmol) to provide 1-(3,3-diethoxypropyl)-2-propyl-1H-imidazo[4,5-c]quinoline (22.3 g) as a dark oil that was used directly in the next step without further purification.

Step 4:

The general method described in Steps 9 and 10 of Example 1 was used to aminate 1-(3,3-diethoxyproyl)-2-propyl-1H-imidazo[4,5-c]quinoline (4.50 g, 13.2 mmol) by reaction with m-CPBA (5.3 g) to provide 1-(3,3-diethoxypropyl)-5-oxido-2-propyl-1H-imidazo[4,5-c]quinoline followed by reaction with p-toluenesulfonyl chloride (4.89 g, 25.7 mmol) and ammonium hydroxide solution (40 mL) to provide 1-(3,3-diethoxypropyl)-2-propyl-1H-imidazo[4,5-c]quinolin-4-amine as grey needles after recrystallization from methanol, mp 148-150° C.

MS (APCI) m/z=357 (M+H)$^+$;

Anal. calcd for $C_{20}H_{28}N_4O_2$: C, 67.39; H, 7.92; N, 15.72. Found C, 67.24; H, 8.05; N, 15.70.

Example 31

1-[2,2-Dimethyl-3-(2-methyl[1,3]dioxolan-2-yl)propyl]-1H-imidazo[4,5-c]quinolin-4-amine

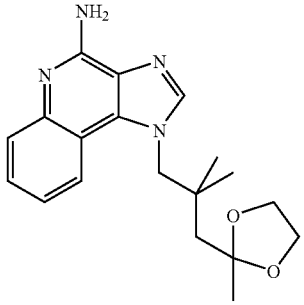 [SMILES: CC(C)(Cn1cnc2c(N)nc3ccccc3c21)CC1(C)OCCO1]

Steps 1-5 were the same as described for Example 22.

Step 6:

The general method described in Step 6 of Example 22 was used to cyclize $N^4$-[2,2-dimethyl-3-(2-methyl-[1,3]dioxolan-2-yl)propyl]quinoline-3,4-diamine (8.1 g, 25.7 mmol) by reaction with trimethyl orthoformate (3.3 g, 10 mmol) to provide 1-[2,2-dimethyl-3-(2-methyl[1,3]dioxolan-2-yl)propyl]-1H-imidazo[4,5-c]quinoline (8.8 g) as an oil that was used directly in the next step without further purification.

Step 7:

The general method described in Steps 9 and 10 of Example 1 was used to aminate 1-[2,2-dimethyl-3-(2-methyl[1,3]dioxolan-2-yl)propyl]-1H-imidazo[4,5-c]quinoline (8.8 g, 27 mmol) by reaction with m-CPBA (11.8 g) to provide 1-[2,2-dimethyl-3-(2-methyl-[1,3]dioxolan-2-yl)propyl]-5-oxido-1H-imidazo[4,5-c]quinoline followed by reaction with p-toluenesulfonyl chloride (9.1 g, 48 mmol) and ammonium hydroxide solution (100 mL) to provide 1-[2,2-dimethyl-3-(2-methyl[1,3]dioxolan-2-yl)propyl]-1H-imidazo[4,5-c]quinolin-4-amine as a light brown solid after chromatography on silica gel (elution with a solution of 7% methanol in dichloromethane that contained about 5 mL of ammonium hydroxide solution per liter of eluent) and recrystallization from aqueous methanol, mp 153-155° C.

MS (APCI) m/z 341 (M+H)$^+$;

Anal. calcd for $C_{19}H_{24}N_4O_2$: C, 67.04; H, 7.11; N, 16.46. Found: C, 66.76; H, 7.39; N, 16.41.

Example 32

5-(4-Amino-1H-imidazo[4,5-c]quinolin-1-yl)-4,4-dimethylpentan-2-one

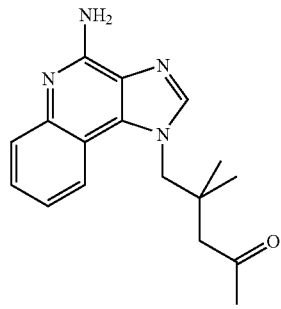 [SMILES: CC(=O)CC(C)(C)Cn1cnc2c(N)nc3ccccc3c21]

By the general method of Example 11, 1-[2,2-dimethyl-3-(2-methyl-[1,3]dioxolan-2-yl)propyl]-1H-imidazo[4,5-c]quinolin-4-amine was hydrolyzed with aqueous hydrochloric acid to provide 5-(4-amino-1H-imidazo[4,5-c]quinolin-1-yl)-4,4-dimethylpentan-2-one as a light yellow solid after recrystallization from aqueous methanol, mp 214-216° C.

MS (APCI) m/z 297 (M+H)$^+$;

Anal. calcd for $C_{18}H_{22}N_4O$: C, 68.89; H, 6.80; N, 18.90. Found: C, 68.91; H, 6.85; N, 19.12.

Example 33

5-(4-Amino-6,7-dimethyl-2-propyl-1H-imidazo[4,5-c]pyridin-1-yl)pentan-2-one

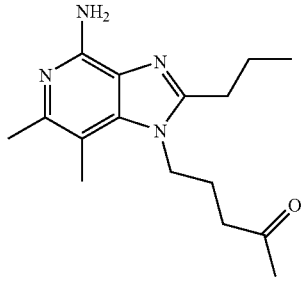 [SMILES: CCCc1nc2c(N)nc(C)c(C)c2n1CCCC(C)=O]

Step 1:

2,4-Dichloro-5,6-dimethyl-3-nitropyridine (135.0 g, 0.488 mol) and ethyl 4-aminobutyrate hydrochloride (114.0 g, 0.683 mol) were triturated in N,N-dimethylformamide (675 mL) (DMF) at 0° C. Triethylamine (272.6 mL, 1.95 mol) was added to generate a brown slurry. After 15 minutes, the reaction mixture was allowed to warm to ambient temperature and the reaction was stirred overnight. Analysis by $^1$H NMR indicated the reaction was incomplete. An additional amount of triethylamine (102.2 mL, 0.73 mol) and ethyl 4-aminobutyrate hydrochloride (35.28 g, 0.159 mol) in DMF (200 mL) were added to the reaction mixture and allowed to stir over an additional 24 hours. Half of the reaction mixture was added to separate flasks and deionized water (3 L) was added to each flask and were stirred for 1 hour. The resulting precipitate in each flask was harvested by filtration and dried under reduced pressure. The crude product was recrystallized from ethyl acetate and filtered to yield 86.20 g of ethyl 4-[(2-chloro-5,6-dimethyl-3-nitropyridin-4-yl)amino]butyrate as a yellow granular solid.

Step 2:

Ethyl 4-[(2-chloro-5,6-dimethyl-3-nitropyridin-4-yl)amino]butyrate (86.2 g, 0.276 mol), sodium azide (35.49 g, 0.552 mol), and cerium chloride heptahydrate (50.86 g, 0.138 mol) were triturated in a 9:1 mixture of acetonitrile:water (1012 mL). The reaction mixture was stirred and heated to reflux for 18 hours. The reaction was filtered and the yellow filtrate was concentrated under reduced pressure to yield 90.94 g of crude product. The material was triturated at 95° C. with 360 mL ethyl acetate and filtered. The filtrate produced pale yellow crystals at ambient temperature to afford 64.3 g of ethyl 4-[(5,6-dimethyl-8-nitrotetrazolo[1,5-a]pyridin-7-yl)amino]butyrate as a yellow solid.

Step 3:

Ethyl 4-[(5,6-dimethyl-8-nitrotetrazolo[1,5-a]pyridin-7-yl)amino]butyrate (64.3 g, 0.198 mol) was mixed with acetonitrile (2 L) and catalytic 10% palladium on carbon was added. The mixture was placed on a hydrogenator for 72 hours and filtered through a layer of CELITE filter aid. The filtrate was concentrated under reduced pressure to yield 58.2 g of ethyl 4-[(8-amino-5,6-dimethyltetrazolo[1,5-a]pyridin-7-yl)amino]butyrate.

Step4:

Pyridinium chloride (8.57 g, 74 mmol) and ortho-n-butyric acid trimethyl ester (34.6 mL, 217 mmol) were sequentially added to ethyl 4-[(8-amino-5,6-dimethyltetrazolo[1,5-a]pyridin-7-yl)amino]butyrate (58.2 g, 198 mmol) triturated in toluene (1165 mL) and heated to reflux for 0.5 hours. The reaction mixture was concentrated under reduced pressure and partitioned between dichloromethane and saturated aqueous sodium carbonate. The organic layer was isolated, concentrated under reduced pressure, and 52.99 g of ethyl 4-(5,6-dimethyl-8-propyl-1H-imidazo[4,5-c]tetrazolo[1,5-a]pyridin-7-yl)butyrate solid was recrystallized from ethyl acetate and used without additional purification.

Step 5:

Ethyl 4-(5,6-dimethyl-8-propyl-1H-imidazo[4,5-c]tetrazolo[1,5-a]pyridin-7-yl)butyrate (52.99 g, 0.153 mol) was slurried in ethanol (550 mL) and treated with a 50% sodium hydroxide solution for 0.5 hours. The reaction was concentrated under reduced pressure, maintained overnight, and dissolved in water (250 mL). The pH was adjusted to 5 and the resulting white precipitate was filtered. The residue was triturated at ambient temperature with methanol (1 L) and concentrated under reduced pressure to afford 4-(5,6-dimethyl-8-propyl-1H-imidazo[4,5-c]tetrazolo[1,5-a]pyridin-7-yl)butyric acid which was used without any further purification.

Step 6:

Five drops of N,N-dimethylformamide (DMF) were added to 4-(5,6-dimethyl-8-propyl-1H-imidazo[4,5-c]tetrazolo[1,5-a]pyridin-7-yl)butyric acid (36.22 g, 113.8 mmol) and dichloromethane (725 mL). Oxalyl chloride (29.8 mL, 341.3 mmol) was added dropwise to the reaction mixture. After 10 minutes, the reaction mixture was concentrated under reduced pressure to afford 4-(5,6-dimethyl-8-propyl-1H-imidazo[4,5-c]tetrazolo[1,5-a]pyridin-7-yl)butyryl chloride.

Step 7:

4-(5,6-Dimethyl-8-propyl-1H-imidazo[4,5-c]tetrazolo[1,5-a]pyridin-7-yl)butyryl chloride (38.39 g, 114 mmol) was triturated with chloroform (768 mL) and cooled to 0° C. N,O-Dimethylhydroxylamine hydrochloride (16.68 g, 171 mmol) and triethylamine (47.7 mL, 342 mmol, dropwise addition) were sequentially added to the reaction mixture and stirred for 0.5 hours. The reaction mixture was stirred for 10 additional minutes after addition of saturated aqueous sodium bicarbonate solution (400 mL). The organic phase was isolated, dried over sodium sulfate, and concentrated under reduced pressure to afford 40.01 g of 4-(5,6-dimethyl-8-propyl-1H-imidazo[4,5-c]tetrazolo[1,5-a]pyridin-7-yl)-N-methoxy-N-methylbutyramide as a yellow oil.

Step 8:

Methylmagnesium iodide (5.5 mL, 41.5 mmol) was added slowly dropwise to a triturated mixture of 4-(5,6-dimethyl-8-propyl-1H-imidazo[4,5-c]tetrazolo[1,5-a]pyridin-7-yl)-N-methoxy-N-methylbutyramide (10.0 g, 27.7 mmol) and tetrahydrofuran (125 mL) at 0° C. The reaction was warmed to ambient temperature and $^1$H NMR indicated the reaction was incomplete after stirring overnight. An additional amount of methyl magnesium iodide (5.5 mL, 41.5 mmol) was added at 18 and 21.75 hours after the initial addition. A final addition of methyl magnesium iodide (3.6 mL, 27 mmol) was added at 23 hours after the initial addition and allowed to react for one additional hour. Addition of 1N aqueous hydrogen chloride solution (35 mL) followed to generate a yellow-orange slurry and the mixture was concentrated under reduced pressure. The residue was dissolved in dichloromethane (200 mL), washed with saturated aqueous sodium bicarbonate (100 mL), dried over sodium sulfate and concentrated under reduced pressure to afford 8.15 g of 5-(5,6-dimethyl-8-propyl-1H-imidazo[4,5-c]tetrazolo[1,5-a]pyridin-7-yl)pentan-2-one without any further purification.

Step 9:

Triphenylphosphine (13.5 g, 51.5 mmol) was added to a mixture of 5-(5,6-dimethyl-8-propyl-1H-imidazo[4,5-c]tetrazolo[1,5-a]pyridin-7-yl)pentan-2-one (8.15 g, 25.8 mmol) and 1,2-dichlorobenzene (163 mL) and heated to 133° C. for 13.5 hours. The reaction temperature was incrementally increased to 140° C. over an additional 1.5 hours. Additional triphenylphosphine (3.39 g, 12.9 mmol) was then added and the reaction was heated for one additional hour. The resulting dark brown solution was cooled to ambient temperature and concentrated under reduced pressure. The resulting residue was dissolved in methanol (150 mL) and 1 N aqueous hydrochloric acid (75 mL) was added to create a slurry. The reaction was stirred at 40° C. for an hour, upon which the resulting mixture was filtered, concentrated under reduced pressure, dissolved in dichloromethane (100 mL) and washed with 1 N aqueous hydrochloric acid. The aqueous layer was adjusted to pH 14 with saturated aqueous sodium bicarbonate and 50% sodium hydroxide solutions and the product was extracted into chloroform (250 mL). The organic layer was dried with sodium sulfate and concentrated under reduced pressure to produce 4.61 g of a brown solid material. The material was recrystallized from acetonitrile to yield 2.53 g of isolated material. A portion of the material (1.22 g) was purified by column chromatography on a BIOTAGE HORIZON High-Performance Flash Chromatography instrument (eluting with chloroform/methanol/ammonium hydroxide (80/18/2):chloroform ranging in ratios from 0:100 to 40:60) to provide 0.81 g of 5-(4-amino-6,7-dimethyl-2-propyl-1H-imidazo[4,5-c]pyridin-1-yl)pentan-2-one as an off-white powder, mp 148.5-149.5° C. $^1$H NMR (300 MHz, DMSO-d$_6$) δ 5.58 (s, 2H), 4.16 (t, J=8.1 Hz, 2H), 2.77 (t, J=8.1 Hz, 2H), 2.58 (t, J=6.9 Hz, 2H), 2.37 (s, 3H), 2.30 (s, 3H), 2.10 (s, 3H), 1.80 (m, J=7.5 Hz, 4H), 1.00 (t, J=7.5 Hz, 3H; MS (APCI) m/z 289 (M+H)$^+$; Anal. calcd for $C_{20}H_{26}N_6O_2$: C, 66.64; H, 8.39; N, 19.43. Found: C, 66.40; H, 8.63; N, 1944.

Example 34

Ethyl 4-[4-amino-2-(ethoxymethyl)-1H-imidazo[4,5-c]quinolin-1-yl]butanoate

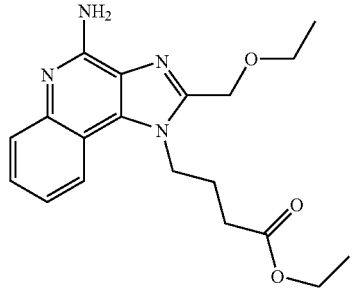 [SMILES: CCOCc1nc2c(N)nc3ccccc3c2n1CCCC(=O)OCC]

Step 1:

A solution of ethoxyacetyl chloride (7.00 g, 57.1 mmol) in dichloromethane (10 mL) was added dropwise to a stirred solution of ethyl 4-(3-aminoquinolin-4-ylamino)butyrate (prepared as described in Steps 1-2 of Example 17, 12.5 g, 45.7 mmol) in dichloromethane (100 mL) at room temperature. After 1.5 hours, the reaction mixture was concentrated under reduced pressure to afford a solid to which was added ethanol (100 mL) and triethylamine (17.4 mL, 125 mmol). The solution was left at room temperature for 5 days, then was heated at reflux for 2 hours. The solution was concentrated under reduced pressure. The residue was partitioned between dichloromethane (150 mL) and water (50 mL). The organic layer was washed with water (50 mL) and saturated aqueous sodium bicarbonate (50 mL), dried over potassium carbonate, filtered, and concentrated under reduced pressure to yield 15.4 g of ethyl 4-[2-(ethoxymethyl)-1H-imidazo[4,5-c]quinolin-1-yl]butanoate as a brown oil that was used in the next step without purification.

Step 2:

To a stirred solution of ethyl 4-[2-(ethoxymethyl)-1H-imidazo[4,5-c]quinolin-1-yl]butanoate (15.4 g, 45.1 mmol) in dichloromethane (150 mL) at 0° C. was added mCPBA (approximately 77% purity, 19.7 g, 87.9 mmol) in portions. The reaction mixture was stirred at room temperature for 1.5 hours, then concentrated ammonium hydroxide (50 mL) was added. p-Toluenesulfonyl chloride was added in portions to the mixture, which was stirred for 1 hour then filtered. The filtrate was transferred to a separatory funnel, saturated aqueous sodium bicarbonate (50 mL) was added and the layers were separated. The aqueous layer was extracted with dichloromethane (2×50 mL). The organic layers were combined, washed with 5% aqueous sodium hydroxide (2×75 mL), dried over potassium carbonate, filtered, and concentrated under reduced pressure to yield a brown solid that was slurried in ethyl acetate (50 mL) and filtered. The filtrate was concentrated under reduced pressure and the solid was recrystallized from ethanol/water four times, then was dissolved in dichloromethane (100 mL). The solution was washed with saturated aqueous sodium bicarbonate (2×50 mL), then was concentrated under reduced pressure to yield a solid that was recrystallized from ethanol/water three times. The crystals were dried in a vacuum oven at 70° C. to provide ethyl 4-[4-amino-2-(ethoxymethyl)-1H-imidazo[4,5-c]quinolin-1-yl]butanoate as pale yellow crystals, mp 129-131° C.

MS (APCI) m/z 357 (M+H$^+$);

Anal. calcd for C$_{19}$H$_{24}$N$_4$O$_3$: C, 64.03; H, 6.79; N, 15.72. Found: C, 63.76; H, 6.89; N, 15.49.

Example 35

4-[4-Amino-2-(ethoxymethyl)-1H-imidazo[4,5-c]quinolin-1-yl]-N-methoxy-N-methylbutanamide

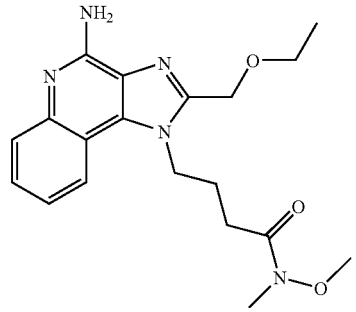 [SMILES: CCOCc1nc2c(N)nc3ccccc3c2n1CCCC(=O)N(C)OC]

Step 1:

A solution of trimethylaluminum in toluene (2 M, 35 mL, 70 mmol) was added to a stirred suspension of N,O-dimethylhydroxylamine hydrochloride (6.81 g, 69.9 mmol) in dichloromethane (100 mL) at 0° C. The reaction mixture was stirred for 15 minutes at 0° C., then at room temperature for 15 minutes before cooling to 0° C. again. A solution of ethyl 4-[2-(ethoxymethyl)-1H-imidazo[4,5-c]quinolin-1-yl]butanoate (prepared as described in Step 1 of Example 34) in dichloromethane (50 mL) was added. After 15 minutes, the reaction mixture was allowed to warm to room temperature, then was heated at reflux for 2 days. The reaction mixture was allowed to cool to room temperature and dichloromethane (150 mL) was added. Methanol (10 mL) followed by 10% aqueous hydrochloric acid (10 mL) were added slowly. To the mixture was added saturated aqueous sodium bicarbonate. The mixture was transferred to a separatory funnel and the layers were separated. The aqueous layer was extracted with dichloromethane. The organic layers were combined, washed with saturated aqueous sodium bicarbonate, dried over potassium carbonate, filtered, and concentrated under reduced pressure to yield 13.9 g of an oil that was used without purification in the next step.

Step 2:

The material from Step 1 (13.9 g) was treated according to the general conditions described in Step 2 of Example 34. The crude product was slurried in ethyl acetate and filtered. The filtrate was concentrated and purified by flash chromatography (silica gel, elution with a 7% methanol in dichloromethane solution containing 0.4% concentrated ammonium hydroxide by volume) to afford an oil that was triturated with ethyl acetate. A solid formed that was isolated by filtration and recrystallized twice from methanol/water. The crystals were dried overnight in a vacuum oven at 70° C. to provide 1.59 g of 4-[4-amino-2-(ethoxymethyl)-1H-imidazo[4,5-c]quinolin-1-yl]-N-methoxy-N-methylbutanamide as a pale yellow solid, mp 163-165° C.

MS (APCI) m/z 372 (M+H$^+$);

Anal. calcd for C$_{19}$H$_{25}$N$_5$O$_3$: C, 61.44; H, 6.78; N, 18.85. Found: C, 61.48; H, 6.82; N, 18.68.

Example 36

5-(4-Amino-2-propyl-1H-imidazo[4,5-c]quinolin-1-yl)-N-methoxy-N-methylpentanamide

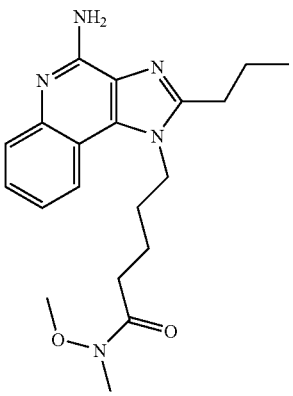 [SMILES: CCCc1nc2c(N)nc3ccccc3c2n1CCCCC(=O)N(C)OC]

Step 1:

Potassium carbonate (66.23 g, 0.479 mol), triethylamine (167 mL, 1.20 mol), and ethyl 5-aminovalerate hydrochloride (104 g, 0.575 mol) were added to a mixture of 4-chloro-3-nitroquinoline (100 g, 0.470 mol) in chloroform (1 L). The reaction mixture was stirred at room temperature for 4 hours, then water (200 mL) was added. The mixture was transferred to a separatory funnel and the layers were separated. The organic layer was washed with saturated aqueous sodium bicarbonate and brine, dried over magnesium sulfate, filtered, and concentrated under reduced pressure to afford 151 g of ethyl 5-[(3-nitroquinolin-4-yl)amino]pentanoate.

Step 2:

The general method described in Step 2 of Example 6 was used to reduce ethyl 5-[(3-nitroquinolin-4-yl)amino]pentanoate (151 g, 0.476 mol) to 131.5 g of crude ethyl 5-[(3-aminoquinolin-4-yl)amino]pentanoate, which was used in the next step without purification.

Step 3:

The general method described in Step 3 of Example 6 was used to convert crude ethyl 5-[(3-aminoquinolin-4-yl)amino] pentanoate (26.3 g, 91.5 mmol) into 28 g of crude ethyl 5-(2-propyl-1H-imidazo[4,5-c]quinolin-1-yl)pentanoate, using trimethyl orthobutyrate in lieu of triethyl orthoacetate.

Step 4:

A solution of sodium hydroxide (2.23 g, 55.9 mmol) in water (100 mL) was added to a solution of ethyl 5-(2-propyl-1H-imidazo[4,5-c]quinolin-1-yl)pentanoate (14.6 g, 43.0 mmol) in ethanol (100 mL). The reaction mixture was stirred at room temperature overnight, then the ethanol was removed under reduced pressure. The remaining aqueous solution was washed with dichloromethane and adjusted to pH 5 with 10% aqueous hydrochloric acid. The aqueous layer was extracted with dichloromethane (2×). The later organic layers were combined, dried over magnesium sulfate, filtered, and concentrated to yield 11.5 g of 5-(2-propyl-1H-imidazo[4,5-c] quinolin-1-yl)pentanoic acid as yellow solid.

Step 5

Oxalyl chloride (2.62 mL, 30.1 mmol) was added to a solution of 5-(2-propyl-1H-imidazo[4,5-c]quinolin-1-yl) pentanoic acid (5.21 g, 16.7 mmol) in dichloromethane (50 mL) at room temperature. The reaction was stirred for 1 hour, then the volatiles were removed under reduced pressure. Dichloromethane (50 mL) was added to the residue, followed by N,O-dimethylhydroxylamine hydrochloride (3.26 g, 33.5 mmol) and N,N-dimethylformamide (2 mL). The reaction mixture was stirred at room temperature overnight, then was concentrated under reduced pressure. The residue was diluted with dichloromethane and an ammonium hydroxide solution. The mixture was transferred to a separatory funnel and the layers were separated. The organic layer was washed with saturated aqueous sodium bicarbonate and brine, dried over magnesium sulfate, filtered, and concentrated under reduced pressure to afford 5.5 g of crude N-methoxy-N-methyl-5-(2-propyl-1H-imidazo[4,5-c]quinolin-1-yl)pentanamide as a brown oil that was used without purification in the next step.

Step 6:

The material from Step 5 was treated according to a modification of the procedure described in Step 2 of Example 34. The reaction mixture was worked up by separating the layers using a separatory funnel. The organic layer was washed with saturated aqueous sodium bicarbonate and brine, dried over magnesium sulfate, filtered, and concentrated under reduced pressure. The crude 5-(4-amino-2-propyl-1H-imidazo[4,5-c] quinolin-1-yl)-N-methoxy-N-methylpentanamide was purified by flash chromatography (silica gel, eluted with 10% methanol in dichloromethane) to provide a solid. Acetone was added to the solid and the mixture was sonicated. The solid was isolated by filtration and dried at 80° C. in a vacuum oven to provide 5-(4-amino-2-propyl-1H-imidazo[4,5-c] quinolin-1-yl)-N-methoxy-N-methylpentanamide as beige needles, mp 150-151° C.

MS (APCI) m/z 370.1 (M+H$^+$);

Anal. calcd for $C_{20}H_{27}N_5O_2 \cdot 0.15 H_2O$: C, 64.51; H, 7.40; N, 18.81. Found: C, 64.16; H, 7.40; N, 18.81.

Example 37

1-[4-Amino-2-(ethoxymethyl)-1H-imidazo[4,5-c]quinolin-1-yl]butan-2-one

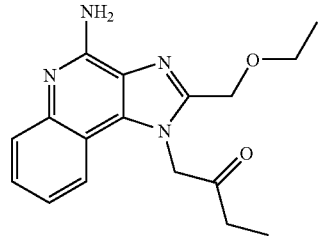 [SMILES: CCOCc1nc2c(N)nc3ccccc3c2n1CC(=O)CC]

Step 1:

1-(Aminomethyl)cyclopropanol was prepared using the method of I. L. Lysenko and O. G. Kulinkovich, Russ. J. Org. Chem., 37, pp. 1238-1243 (2001). A solution of 4-chloro-3-nitroquinoline (7.28 g, 34.9 mmol) in dichloromethane (30 mL) was added dropwise to a 0° C. stirred suspension of 1-(aminomethyl)cyclopropanol (36.7 mmol) and triethylamine (6.30 mL, 45.4 mmol) in dichloromethane (120 mL). The mixture was stirred at room temperature for 3 days, then was concentrated under reduced pressure. The residue was suspended in water (150 mL) and was stirred for 3 hours. The solid was isolated by filtration, washed with water (50 mL), and dried in a vacuum oven at 75° C. to afford 8.99 g of 1-{[(3-nitroquinolin-4-yl)amino]methyl}cyclopropanol as a yellow solid.

Step 2:

A mixture of 1-{[(3-nitroquinolin-4-yl)amino] methyl}cyclopropanol (4.00 g, 15.4 mmol) and 5% platinum on carbon (400 mg) in ethyl acetate (80 mL) and methanol (8 mL) was hydrogenated on a Parr apparatus at 35 psi ($2.4 \times 10^5$ Pa) of hydrogen at room temperature for 3 hours. The mixture was filtered through CELITE filter agent, which was rinsed with 10% methanol/ethyl acetate. The filtrate was concentrated to an orange oil that was used directly in the next step.

Step 3

The material from Step 2 was dissolved in dichloromethane (70 mL). The solution was cooled to 0° C. and ethoxyacetyl chloride (1.7 mL, 16.9 mmol) was added dropwise. The reaction mixture was stirred at 0° C. for 1 hour, then the solvent was removed under reduced pressure. The residue was used directly in the next step.

Step 4:

The material from Step 3 was dissolved in ethanol (70 mL) and 2 M aqueous sodium hydroxide (15 mL, 30.8 mmol) was added. The reaction mixture was heated at 60° C. for 1 hour, then was stirred at room temperature overnight. The volatiles were removed under reduced pressure and to the resulting residue was added dichloromethane (70 mL) and water (50 mL). The mixture was adjusted to pH 7 with 1 M HCl. The layers were separated and the aqueous layer was extracted with dichloromethane (25 mL). The organic layers were combined, dried over magnesium sulfate, filtered, and concentrated to afford 4.23 g of crude 1-[2-(ethoxymethyl)-1H-imidazo[4,5-c]quinolin-1-yl]butan-2-one a tan solid.

Step 5:

mCPBA (2.11 g, 8.57 mmol) was added to a solution of 1-[2-(ethoxymethyl)-1H-imidazo[4,5-c]quinolin-1-yl]butan-2-one (1.96 g, 6.59 mmol) in chloroform (30 mL) at room temperature. The reaction mixture was stirred for 1 hour, then was cooled to 0° C. Concentrated ammonium hydroxide (10 mL) and p-toluenesulfonyl chloride (1.38 g, 7.25 mmol) were added. The mixture was stirred at 0° C. for 1 hour, then was filtered. The filtrate was diluted with dichloromethane (50 mL) and saturated aqueous sodium bicarbonate (50 mL). The layers were separated and the aqueous layer was extracted with dichloromethane (25 mL). The organic layers were combined, dried over magnesium sulfate, filtered, and concentrated to yield a brown solid. The solid was purified by chromatography on a HORIZON High-Performance Flash Chromatography (HPFC) instrument (available from Biotage, Inc, Charlottesville, Va., USA) (silica gel, gradient elution with 0-35% of a solution comprised of 80% CHCl3, 18% MeOH, and 2% conc. NH4OH (CMA) in chloroform) to afford a tan solid that was recrystallized from chloroform/hexanes. The crystals were isolated by filtration and dried in a vacuum oven at 80° C. to afford 0.718 g of 1-[4-amino-2-(ethoxymethyl)-1H-imidazo[4,5-c]quinolin-1-yl]butan-2-one as pale pink needles, mp 187-188° C.

MS (APCI) m/z 313 $(M+H)^+$;

Anal. calcd for $C_{17}H_{20}N_4O_2$: C, 65.37; H, 6.45; N, 17.94. Found: C, 65.22; H, 6.19; N, 17.71.

Exemplary Compounds

Certain exemplary compounds, including some of those described above in the Examples, have the following Formulas (I-2a, I-4a, and I-3 a) wherein X, $R_2$, and $R_{1-1}$ are defined immediately below in the table. In this table, for each ring system, each line represents one specific compound.

I-2a

I-4a

I-3a

| $R_2$ | X | $R_{1-1}$ |
|---|---|---|
| H (hydrogen) | —CH2— | methyl |
| H | —CH2— | ethyl |
| H | —CH2— | n-propyl |
| H | —CH2— | isopropyl |
| H | —CH2— | cyclopropyl |
| H | —CH2— | n-butyl |
| H | —CH2— | sec-butyl |
| H | —CH2— | isobutyl |
| H | —CH2— | tert-butyl |
| H | —CH2— | n-pentyl |
| H | —CH2— | cyclopentyl |
| H | —CH2— | n-hexyl |
| H | —CH2— | cyclohexyl |
| H | —CH2— | phenyl |
| H | —CH2— | 4-chlorophenyl |
| H | —CH2— | 2,4-dichlorophenyl |
| H | —(CH2)2— | methyl |
| H | —(CH2)2— | ethyl |
| H | —(CH2)2— | n-propyl |
| H | —(CH2)2— | isopropyl |
| H | —(CH2)2— | cyclopropyl |
| H | —(CH2)2— | n-butyl |
| H | —(CH2)2— | sec-butyl |
| H | —(CH2)2— | isobutyl |
| H | —(CH2)2— | tert-butyl |
| H | —(CH2)2— | n-pentyl |
| H | —(CH2)2— | cyclopentyl |
| H | —(CH2)2— | n-hexyl |
| H | —(CH2)2— | cyclohexyl |
| H | —(CH2)2— | phenyl |
| H | —(CH2)2— | 4-chlorophenyl |
| H | —(CH2)2— | 2,4-dichlorophenyl |
| H | —(CH2)3— | methyl |
| H | —(CH2)3— | ethyl |
| H | —(CH2)3— | n-propyl |
| H | —(CH2)3— | isopropyl |
| H | —(CH2)3— | cyclopropyl |
| H | —(CH2)3— | n-butyl |
| H | —(CH2)3— | sec-butyl |
| H | —(CH2)3— | isobutyl |
| H | —(CH2)3— | tert-butyl |
| H | —(CH2)3— | n-pentyl |
| H | —(CH2)3— | cyclopentyl |
| H | —(CH2)3— | n-hexyl |
| H | —(CH2)3— | cyclohexyl |
| H | —(CH2)3— | phenyl |
| H | —(CH2)3— | 4-chlorophenyl |
| H | —(CH2)3— | 2,4-dichlorophenyl |
| H | —(CH2)4— | methyl |
| H | —(CH2)4— | ethyl |
| H | —(CH2)4— | n-propyl |
| H | —(CH2)4— | isopropyl |
| H | —(CH2)4— | cyclopropyl |
| H | —(CH2)4— | n-butyl |
| H | —(CH2)4— | sec-butyl |
| H | —(CH2)4— | isobutyl |
| H | —(CH2)4— | tert-butyl |
| H | —(CH2)4— | n-pentyl |
| H | —(CH2)4— | cyclopentyl |
| H | —(CH2)4— | n-hexyl |
| H | —(CH2)4— | cyclohexyl |
| H | —(CH2)4— | phenyl |
| H | —(CH2)4— | 4-chlorophenyl |
| H | —(CH2)4— | 2,4-dichlorophenyl |
| H | —(CH2)5— | methyl |
| H | —(CH2)5— | ethyl |
| H | —(CH2)5— | n-propyl |
| H | —(CH2)5— | isopropyl |
| H | —(CH2)5— | cyclopropyl |
| H | —(CH2)5— | n-butyl |
| H | —(CH2)5— | sec-butyl |
| H | —(CH2)5— | isobutyl |
| H | —(CH2)5— | tert-butyl |
| H | —(CH2)5— | n-pentyl |
| H | —(CH2)5— | cyclopentyl |
| H | —(CH2)5— | n-hexyl |
| H | —(CH2)5— | cyclohexyl |
| H | —(CH2)5— | phenyl |
| H | —(CH2)5— | 4-chlorophenyl |
| H | —(CH2)5— | 2,4-dichlorophenyl |
| H | —(CH2)6— | methyl |
| H | —(CH2)6— | ethyl |
| H | —(CH2)6— | n-propyl |

| | | |
|---|---|---|
| H | —(CH₂)₆— | isopropyl |
| H | —(CH₂)₆— | cyclopropyl |
| H | —(CH₂)₆— | n-butyl |
| H | —(CH₂)₆— | sec-butyl |
| H | —(CH₂)₆— | isobutyl |
| H | —(CH₂)₆— | tert-butyl |
| H | —(CH₂)₆— | n-pentyl |
| H | —(CH₂)₆— | cyclopentyl |
| H | —(CH₂)₆— | n-hexyl |
| H | —(CH₂)₆— | cyclohexyl |
| H | —(CH₂)₆— | phenyl |
| H | —(CH₂)₆— | 4-chlorophenyl |
| H | —(CH₂)₆— | 2,4-dichlorophenyl |
| H | —CH₂C(CH₃)₂— | methyl |
| H | —CH₂C(CH₃)₂— | ethyl |
| H | —CH₂C(CH₃)₂— | n-propyl |
| H | —CH₂C(CH₃)₂— | isopropyl |
| H | —CH₂C(CH₃)₂— | cyclopropyl |
| H | —CH₂C(CH₃)₂— | n-butyl |
| H | —CH₂C(CH₃)₂— | sec-butyl |
| H | —CH₂C(CH₃)₂— | isobutyl |
| H | —CH₂C(CH₃)₂— | tert-butyl |
| H | —CH₂C(CH₃)₂— | n-pentyl |
| H | —CH₂C(CH₃)₂— | cyclopentyl |
| H | —CH₂C(CH₃)₂— | n-hexyl |
| H | —CH₂C(CH₃)₂— | cyclohexyl |
| H | —CH₂C(CH₃)₂— | phenyl |
| H | —CH₂C(CH₃)₂— | 4-chlorophenyl |
| H | —CH₂C(CH₃)₂— | 2,4-dichlorophenyl |
| H | —CH₂C(CH₃)₂CH₂— | methyl |
| H | —CH₂C(CH₃)₂CH₂— | ethyl |
| H | —CH₂C(CH₃)₂CH₂— | n-propyl |
| H | —CH₂C(CH₃)₂CH₂— | isopropyl |
| H | —CH₂C(CH₃)₂CH₂— | cyclopropyl |
| H | —CH₂C(CH₃)₂CH₂— | n-butyl |
| H | —CH₂C(CH₃)₂CH₂— | sec-butyl |
| H | —CH₂C(CH₃)₂CH₂— | isobutyl |
| H | —CH₂C(CH₃)₂CH₂— | tert-butyl |
| H | —CH₂C(CH₃)₂CH₂— | n-pentyl |
| H | —CH₂C(CH₃)₂CH₂— | cyclopentyl |
| H | —CH₂C(CH₃)₂CH₂— | n-hexyl |
| H | —CH₂C(CH₃)₂CH₂— | cyclohexyl |
| H | —CH₂C(CH₃)₂CH₂— | phenyl |
| H | —CH₂C(CH₃)₂CH₂— | 4-chlorophenyl |
| H | —CH₂C(CH₃)₂CH₂— | 2,4-dichlorophenyl |
| H | —(CH₂)₂OCH₂— | methyl |
| H | —(CH₂)₂OCH₂— | ethyl |
| H | —(CH₂)₂OCH₂— | n-propyl |
| H | —(CH₂)₂OCH₂— | isopropyl |
| H | —(CH₂)₂OCH₂— | cyclopropyl |
| H | —(CH₂)₂OCH₂— | n-butyl |
| H | —(CH₂)₂OCH₂— | sec-butyl |
| H | —(CH₂)₂OCH₂— | isobutyl |
| H | —(CH₂)₂OCH₂— | tert-butyl |
| H | —(CH₂)₂OCH₂— | n-pentyl |
| H | —(CH₂)₂OCH₂— | cyclopentyl |
| H | —(CH₂)₂OCH₂— | n-hexyl |
| H | —(CH₂)₂OCH₂— | cyclohexyl |
| H | —(CH₂)₂OCH₂— | phenyl |
| H | —(CH₂)₂OCH₂— | 4-chlorophenyl |
| H | —(CH₂)₂OCH₂— | 2,4-dichlorophenyl |
| H | —(CH₂)₃OCH₂— | methyl |
| H | —(CH₂)₃OCH₂— | ethyl |
| H | —(CH₂)₃OCH₂— | n-propyl |
| H | —(CH₂)₃OCH₂— | isopropyl |
| H | —(CH₂)₃OCH₂— | cyclopropyl |
| H | —(CH₂)₃OCH₂— | n-butyl |
| H | —(CH₂)₃OCH₂— | sec-butyl |
| H | —(CH₂)₃OCH₂— | isobutyl |
| H | —(CH₂)₃OCH₂— | tert-butyl |
| H | —(CH₂)₃OCH₂— | n-pentyl |
| H | —(CH₂)₃OCH₂— | cyclopentyl |
| H | —(CH₂)₃OCH₂— | n-hexyl |
| H | —(CH₂)₃OCH₂— | cyclohexyl |
| H | —(CH₂)₃OCH₂— | phenyl |
| H | —(CH₂)₃OCH₂— | 4-chlorophenyl |
| H | —(CH₂)₃OCH₂— | 2,4-dichlorophenyl |
| —CH₂OH | —CH₂— | methyl |
| —CH₂OH | —CH₂— | ethyl |
| —CH₂OH | —CH₂— | n-propyl |
| —CH₂OH | —CH₂— | isopropyl |
| —CH₂OH | —CH₂— | cyclopropyl |
| —CH₂OH | —CH₂— | n-butyl |
| —CH₂OH | —CH₂— | sec-butyl |
| —CH₂OH | —CH₂— | isobutyl |
| —CH₂OH | —CH₂— | tert-butyl |
| —CH₂OH | —CH₂— | n-pentyl |
| —CH₂OH | —CH₂— | cyclopentyl |
| —CH₂OH | —CH₂— | n-hexyl |
| —CH₂OH | —CH₂— | cyclohexyl |
| —CH₂OH | —CH₂— | phenyl |
| —CH₂OH | —CH₂— | 4-chlorophenyl |
| —CH₂OH | —CH₂— | 2,4-dichlorophenyl |
| —CH₂OH | —(CH₂)₂— | methyl |
| —CH₂OH | —(CH₂)₂— | ethyl |
| —CH₂OH | —(CH₂)₂— | n-propyl |
| —CH₂OH | —(CH₂)₂— | isopropyl |
| —CH₂OH | —(CH₂)₂— | cyclopropyl |
| —CH₂OH | —(CH₂)₂— | n-butyl |
| —CH₂OH | —(CH₂)₂— | sec-butyl |
| —CH₂OH | —(CH₂)₂— | isobutyl |
| —CH₂OH | —(CH₂)₂— | tert-butyl |
| —CH₂OH | —(CH₂)₂— | n-pentyl |
| —CH₂OH | —(CH₂)₂— | cyclopentyl |
| —CH₂OH | —(CH₂)₂— | n-hexyl |
| —CH₂OH | —(CH₂)₂— | cyclohexyl |
| —CH₂OH | —(CH₂)₂— | phenyl |
| —CH₂OH | —(CH₂)₂— | 4-chlorophenyl |
| —CH₂OH | —(CH₂)₂— | 2,4-dichlorophenyl |
| —CH₂OH | —(CH₂)₃— | methyl |
| —CH₂OH | —(CH₂)₃— | ethyl |
| —CH₂OH | —(CH₂)₃— | n-propyl |
| —CH₂OH | —(CH₂)₃— | isopropyl |
| —CH₂OH | —(CH₂)₃— | cyclopropyl |
| —CH₂OH | —(CH₂)₃— | n-butyl |
| —CH₂OH | —(CH₂)₃— | sec-butyl |
| —CH₂OH | —(CH₂)₃— | isobutyl |
| —CH₂OH | —(CH₂)₃— | tert-butyl |
| —CH₂OH | —(CH₂)₃— | n-pentyl |
| —CH₂OH | —(CH₂)₃— | cyclopentyl |
| —CH₂OH | —(CH₂)₃— | n-hexyl |
| —CH₂OH | —(CH₂)₃— | cyclohexyl |
| —CH₂OH | —(CH₂)₃— | phenyl |
| —CH₂OH | —(CH₂)₃— | 4-chlorophenyl |
| —CH₂OH | —(CH₂)₃— | 2,4-dichlorophenyl |
| —CH₂OH | —(CH₂)₄— | methyl |
| —CH₂OH | —(CH₂)₄— | ethyl |
| —CH₂OH | —(CH₂)₄— | n-propyl |
| —CH₂OH | —(CH₂)₄— | isopropyl |
| —CH₂OH | —(CH₂)₄— | cyclopropyl |
| —CH₂OH | —(CH₂)₄— | n-butyl |
| —CH₂OH | —(CH₂)₄— | sec-butyl |
| —CH₂OH | —(CH₂)₄— | isobutyl |
| —CH₂OH | —(CH₂)₄— | tert-butyl |
| —CH₂OH | —(CH₂)₄— | n-pentyl |
| —CH₂OH | —(CH₂)₄— | cyclopentyl |
| —CH₂OH | —(CH₂)₄— | n-hexyl |
| —CH₂OH | —(CH₂)₄— | cyclohexyl |
| —CH₂OH | —(CH₂)₄— | phenyl |
| —CH₂OH | —(CH₂)₄— | 4-chlorophenyl |
| —CH₂OH | —(CH₂)₄— | 2,4-dichlorophenyl |
| —CH₂OH | —(CH₂)₅— | methyl |
| —CH₂OH | —(CH₂)₅— | ethyl |
| —CH₂OH | —(CH₂)₅— | n-propyl |
| —CH₂OH | —(CH₂)₅— | isopropyl |
| —CH₂OH | —(CH₂)₅— | cyclopropyl |
| —CH₂OH | —(CH₂)₅— | n-butyl |
| —CH₂OH | —(CH₂)₅— | sec-butyl |
| —CH₂OH | —(CH₂)₅— | isobutyl |
| —CH₂OH | —(CH₂)₅— | tert-butyl |
| —CH₂OH | —(CH₂)₅— | n-pentyl |
| —CH₂OH | —(CH₂)₅— | cyclopentyl |
| —CH₂OH | —(CH₂)₅— | n-hexyl |
| —CH₂OH | —(CH₂)₅— | cyclohexyl |
| —CH₂OH | —(CH₂)₅— | phenyl |
| —CH₂OH | —(CH₂)₅— | 4-chlorophenyl |
| —CH₂OH | —(CH₂)₅— | 2,4-dichlorophenyl |
| —CH₂OH | —(CH₂)₆— | methyl |
| —CH₂OH | —(CH₂)₆— | ethyl |
| —CH₂OH | —(CH₂)₆— | n-propyl |

| | | |
|---|---|---|
| —CH$_2$OH | —(CH$_2$)$_6$— | isopropyl |
| —CH$_2$OH | —(CH$_2$)$_6$— | cyclopropyl |
| —CH$_2$OH | —(CH$_2$)$_6$— | n-butyl |
| —CH$_2$OH | —(CH$_2$)$_6$— | sec-butyl |
| —CH$_2$OH | —(CH$_2$)$_6$— | isobutyl |
| —CH$_2$OH | —(CH$_2$)$_6$— | tert-butyl |
| —CH$_2$OH | —(CH$_2$)$_6$— | n-pentyl |
| —CH$_2$OH | —(CH$_2$)$_6$— | cyclopentyl |
| —CH$_2$OH | —(CH$_2$)$_6$— | n-hexyl |
| —CH$_2$OH | —(CH$_2$)$_6$— | cyclohexyl |
| —CH$_2$OH | —(CH$_2$)$_6$— | phenyl |
| —CH$_2$OH | —(CH$_2$)$_6$— | 4-chlorophenyl |
| —CH$_2$OH | —(CH$_2$)$_6$— | 2,4-dichlorophenyl |
| —CH$_2$OH | —CH$_2$C(CH$_3$)$_2$— | methyl |
| —CH$_2$OH | —CH$_2$C(CH$_3$)$_2$— | ethyl |
| —CH$_2$OH | —CH$_2$C(CH$_3$)$_2$— | n-propyl |
| —CH$_2$OH | —CH$_2$C(CH$_3$)$_2$— | isopropyl |
| —CH$_2$OH | —CH$_2$C(CH$_3$)$_2$— | cyclopropyl |
| —CH$_2$OH | —CH$_2$C(CH$_3$)$_2$— | n-butyl |
| —CH$_2$OH | —CH$_2$C(CH$_3$)$_2$— | sec-butyl |
| —CH$_2$OH | —CH$_2$C(CH$_3$)$_2$— | isobutyl |
| —CH$_2$OH | —CH$_2$C(CH$_3$)$_2$— | tert-butyl |
| —CH$_2$OH | —CH$_2$C(CH$_3$)$_2$— | n-pentyl |
| —CH$_2$OH | —CH$_2$C(CH$_3$)$_2$— | cyclopentyl |
| —CH$_2$OH | —CH$_2$C(CH$_3$)$_2$— | n-hexyl |
| —CH$_2$OH | —CH$_2$C(CH$_3$)$_2$— | cyclohexyl |
| —CH$_2$OH | —CH$_2$C(CH$_3$)$_2$— | phenyl |
| —CH$_2$OH | —CH$_2$C(CH$_3$)$_2$— | 4-chlorophenyl |
| —CH$_2$OH | —CH$_2$C(CH$_3$)$_2$— | 2,4-dichlorophenyl |
| —CH$_2$OH | —CH$_2$C(CH$_3$)$_2$CH$_2$— | methyl |
| —CH$_2$OH | —CH$_2$C(CH$_3$)$_2$CH$_2$— | ethyl |
| —CH$_2$OH | —CH$_2$C(CH$_3$)$_2$CH$_2$— | n-propyl |
| —CH$_2$OH | —CH$_2$C(CH$_3$)$_2$CH$_2$— | isopropyl |
| —CH$_2$OH | —CH$_2$C(CH$_3$)$_2$CH$_2$— | cyclopropyl |
| —CH$_2$OH | —CH$_2$C(CH$_3$)$_2$CH$_2$— | n-butyl |
| —CH$_2$OH | —CH$_2$C(CH$_3$)$_2$CH$_2$— | sec-butyl |
| —CH$_2$OH | —CH$_2$C(CH$_3$)$_2$CH$_2$— | isobutyl |
| —CH$_2$OH | —CH$_2$C(CH$_3$)$_2$CH$_2$— | tert-butyl |
| —CH$_2$OH | —CH$_2$C(CH$_3$)$_2$CH$_2$— | n-pentyl |
| —CH$_2$OH | —CH$_2$C(CH$_3$)$_2$CH$_2$— | cyclopentyl |
| —CH$_2$OH | —CH$_2$C(CH$_3$)$_2$CH$_2$— | n-hexyl |
| —CH$_2$OH | —CH$_2$C(CH$_3$)$_2$CH$_2$— | cyclohexyl |
| —CH$_2$OH | —CH$_2$C(CH$_3$)$_2$CH$_2$— | phenyl |
| —CH$_2$OH | —CH$_2$C(CH$_3$)$_2$CH$_2$— | 4-chlorophenyl |
| —CH$_2$OH | —CH$_2$C(CH$_3$)$_2$CH$_2$— | 2,4-dichlorophenyl |
| —CH$_2$OH | —(CH$_2$)$_2$OCH$_2$— | methyl |
| —CH$_2$OH | —(CH$_2$)$_2$OCH$_2$— | ethyl |
| —CH$_2$OH | —(CH$_2$)$_2$OCH$_2$— | n-propyl |
| —CH$_2$OH | —(CH$_2$)$_2$OCH$_2$— | isopropyl |
| —CH$_2$OH | —(CH$_2$)$_2$OCH$_2$— | cyclopropyl |
| —CH$_2$OH | —(CH$_2$)$_2$OCH$_2$— | n-butyl |
| —CH$_2$OH | —(CH$_2$)$_2$OCH$_2$— | sec-butyl |
| —CH$_2$OH | —(CH$_2$)$_2$OCH$_2$— | isobutyl |
| —CH$_2$OH | —(CH$_2$)$_2$OCH$_2$— | tert-butyl |
| —CH$_2$OH | —(CH$_2$)$_2$OCH$_2$— | n-pentyl |
| —CH$_2$OH | —(CH$_2$)$_2$OCH$_2$— | cyclopentyl |
| —CH$_2$OH | —(CH$_2$)$_2$OCH$_2$— | n-hexyl |
| —CH$_2$OH | —(CH$_2$)$_2$OCH$_2$— | cyclohexyl |
| —CH$_2$OH | —(CH$_2$)$_2$OCH$_2$— | phenyl |
| —CH$_2$OH | —(CH$_2$)$_2$OCH$_2$— | 4-chlorophenyl |
| —CH$_2$OH | —(CH$_2$)$_2$OCH$_2$— | 2,4-dichlorophenyl |
| —CH$_2$OH | —(CH$_2$)$_3$OCH$_2$— | methyl |
| —CH$_2$OH | —(CH$_2$)$_3$OCH$_2$— | ethyl |
| —CH$_2$OH | —(CH$_2$)$_3$OCH$_2$— | n-propyl |
| —CH$_2$OH | —(CH$_2$)$_3$OCH$_2$— | isopropyl |
| —CH$_2$OH | —(CH$_2$)$_3$OCH$_2$— | cyclopropyl |
| —CH$_2$OH | —(CH$_2$)$_3$OCH$_2$— | n-butyl |
| —CH$_2$OH | —(CH$_2$)$_3$OCH$_2$— | sec-butyl |
| —CH$_2$OH | —(CH$_2$)$_3$OCH$_2$— | isobutyl |
| —CH$_2$OH | —(CH$_2$)$_3$OCH$_2$— | tert-butyl |
| —CH$_2$OH | —(CH$_2$)$_3$OCH$_2$— | n-pentyl |
| —CH$_2$OH | —(CH$_2$)$_3$OCH$_2$— | cyclopentyl |
| —CH$_2$OH | —(CH$_2$)$_3$OCH$_2$— | n-hexyl |
| —CH$_2$OH | —(CH$_2$)$_3$OCH$_2$— | cyclohexyl |
| —CH$_2$OH | —(CH$_2$)$_3$OCH$_2$— | phenyl |
| —CH$_2$OH | —(CH$_2$)$_3$OCH$_2$— | 4-chlorophenyl |
| —CH$_2$OH | —(CH$_2$)$_3$OCH$_2$— | 2,4-dichlorophenyl |
| —CH$_3$ (methyl) | —CH$_2$— | methyl |
| —CH$_3$ | —CH$_2$— | ethyl |
| —CH$_3$ | —CH$_2$— | n-propyl |
| —CH$_3$ | —CH$_2$— | isopropyl |
| —CH$_3$ | —CH$_2$— | cyclopropyl |
| —CH$_3$ | —CH$_2$— | n-butyl |
| —CH$_3$ | —CH$_2$— | sec-butyl |
| —CH$_3$ | —CH$_2$— | isobutyl |
| —CH$_3$ | —CH$_2$— | tert-butyl |
| —CH$_3$ | —CH$_2$— | n-pentyl |
| —CH$_3$ | —CH$_2$— | cyclopentyl |
| —CH$_3$ | —CH$_2$— | n-hexyl |
| —CH$_3$ | —CH$_2$— | cyclohexyl |
| —CH$_3$ | —CH$_2$— | phenyl |
| —CH$_3$ | —CH$_2$— | 4-chlorophenyl |
| —CH$_3$ | —CH$_2$— | 2,4-dichlorophenyl |
| —CH$_3$ | —(CH$_2$)$_2$— | methyl |
| —CH$_3$ | —(CH$_2$)$_2$— | ethyl |
| —CH$_3$ | —(CH$_2$)$_2$— | n-propyl |
| —CH$_3$ | —(CH$_2$)$_2$— | isopropyl |
| —CH$_3$ | —(CH$_2$)$_2$— | cyclopropyl |
| —CH$_3$ | —(CH$_2$)$_2$— | n-butyl |
| —CH$_3$ | —(CH$_2$)$_2$— | sec-butyl |
| —CH$_3$ | —(CH$_2$)$_2$— | isobutyl |
| —CH$_3$ | —(CH$_2$)$_2$— | tert-butyl |
| —CH$_3$ | —(CH$_2$)$_2$— | n-pentyl |
| —CH$_3$ | —(CH$_2$)$_2$— | cyclopentyl |
| —CH$_3$ | —(CH$_2$)$_2$— | n-hexyl |
| —CH$_3$ | —(CH$_2$)$_2$— | cyclohexyl |
| —CH$_3$ | —(CH$_2$)$_2$— | phenyl |
| —CH$_3$ | —(CH$_2$)$_2$— | 4-chlorophenyl |
| —CH$_3$ | —(CH$_2$)$_2$— | 2,4-dichlorophenyl |
| —CH$_3$ | —(CH$_2$)$_3$— | methyl |
| —CH$_3$ | —(CH$_2$)$_3$— | phenyl |
| —CH$_3$ | —(CH$_2$)$_3$— | n-propyl |
| —CH$_3$ | —(CH$_2$)$_3$— | isopropyl |
| —CH$_3$ | —(CH$_2$)$_3$— | cyclopropyl |
| —CH$_3$ | —(CH$_2$)$_3$— | n-butyl |
| —CH$_3$ | —(CH$_2$)$_3$— | sec-butyl |
| —CH$_3$ | —(CH$_2$)$_3$— | isobutyl |
| —CH$_3$ | —(CH$_2$)$_3$— | tert-butyl |
| —CH$_3$ | —(CH$_2$)$_3$— | n-pentyl |
| —CH$_3$ | —(CH$_2$)$_3$— | cyclopentyl |
| —CH$_3$ | —(CH$_2$)$_3$— | n-hexyl |
| —CH$_3$ | —(CH$_2$)$_3$— | cyclohexyl |
| —CH$_3$ | —(CH$_2$)$_3$— | phenyl |
| —CH$_3$ | —(CH$_2$)$_3$— | 4-chlorophenyl |
| —CH$_3$ | —(CH$_2$)$_3$— | 2,4-dichlorophenyl |
| —CH$_3$ | —(CH$_2$)$_4$— | methyl |
| —CH$_3$ | —(CH$_2$)$_4$— | ethyl |
| —CH$_3$ | —(CH$_2$)$_4$— | n-propyl |
| —CH$_3$ | —(CH$_2$)$_4$— | isopropyl |
| —CH$_3$ | —(CH$_2$)$_4$— | cyclopropyl |
| —CH$_3$ | —(CH$_2$)$_4$— | n-butyl |
| —CH$_3$ | —(CH$_2$)$_4$— | sec-butyl |
| —CH$_3$ | —(CH$_2$)$_4$— | isobutyl |
| —CH$_3$ | —(CH$_2$)$_4$— | tert-butyl |
| —CH$_3$ | —(CH$_2$)$_4$— | n-pentyl |
| —CH$_3$ | —(CH$_2$)$_4$— | cyclopentyl |
| —CH$_3$ | —(CH$_2$)$_4$— | n-hexyl |
| —CH$_3$ | —(CH$_2$)$_4$— | cyclohexyl |
| —CH$_3$ | —(CH$_2$)$_4$— | phenyl |
| —CH$_3$ | —(CH$_2$)$_4$— | 4-chlorophenyl |
| —CH$_3$ | —(CH$_2$)$_4$— | 2,4-dichlorophenyl |
| —CH$_3$ | —(CH$_2$)$_5$— | methyl |
| —CH$_3$ | —(CH$_2$)$_5$— | ethyl |
| —CH$_3$ | —(CH$_2$)$_5$— | n-propyl |
| —CH$_3$ | —(CH$_2$)$_5$— | isopropyl |
| —CH$_3$ | —(CH$_2$)$_5$— | cyclopropyl |
| —CH$_3$ | —(CH$_2$)$_5$— | n-butyl |
| —CH$_3$ | —(CH$_2$)$_5$— | sec-butyl |
| —CH$_3$ | —(CH$_2$)$_5$— | isobutyl |
| —CH$_3$ | —(CH$_2$)$_5$— | tert-butyl |
| —CH$_3$ | —(CH$_2$)$_5$— | n-pentyl |
| —CH$_3$ | —(CH$_2$)$_5$— | cyclopentyl |
| —CH$_3$ | —(CH$_2$)$_5$— | n-hexyl |
| —CH$_3$ | —(CH$_2$)$_5$— | cyclohexyl |
| —CH$_3$ | —(CH$_2$)$_5$— | phenyl |
| —CH$_3$ | —(CH$_2$)$_5$— | 4-chlorophenyl |
| —CH$_3$ | —(CH$_2$)$_5$— | 2,4-dichloro hen 1 |
| —CH$_3$ | —(CH$_2$)$_6$— | methyl |
| —CH$_3$ | —(CH$_2$)$_6$— | ethyl |
| —CH$_3$ | —(CH$_2$)$_6$— | n-propyl |

| | | |
|---|---|---|
| —CH₃ | —(CH₂)₆— | isopropyl |
| —CH₃ | —(CH₂)₆— | cyclopropyl |
| —CH₃ | —(CH₂)₆— | n-butyl |
| —CH₃ | —(CH₂)₆— | sec-butyl |
| —CH₃ | —(CH₂)₆— | isobutyl |
| —CH₃ | —(CH₂)₆— | tert-butyl |
| —CH₃ | —(CH₂)₆— | n-pentyl |
| —CH₃ | —(CH₂)₆— | cyclopentyl |
| —CH₃ | —(CH₂)₆— | n-hexyl |
| —CH₃ | —(CH₂)₆— | cyclohexyl |
| —CH₃ | —(CH₂)₆— | 4-chlorophenyl |
| —CH₃ | —(CH₂)₆— | 2,4-dichlorophenyl |
| —CH₃ | —CH₂C(CH₃)₂— | methyl |
| —CH₃ | —CH₂C(CH₃)₂— | ethyl |
| —CH₃ | —CH₂C(CH₃)₂— | n-propyl |
| —CH₃ | —CH₂C(CH₃)₂— | isopropyl |
| —CH₃ | —CH₂C(CH₃)₂— | cyclopropyl |
| —CH₃ | —CH₂C(CH₃)₂— | n-butyl |
| —CH₃ | —CH₂C(CH₃)₂— | sec-butyl |
| —CH₃ | —CH₂C(CH₃)₂— | isobutyl |
| —CH₃ | —CH₂C(CH₃)₂— | tert-butyl |
| —CH₃ | —CH₂C(CH₃)₂— | n-pentyl |
| —CH₃ | —CH₂C(CH₃)₂— | cyclopentyl |
| —CH₃ | —CH₂C(CH₃)₂— | n-hexyl |
| —CH₃ | —CH₂C(CH₃)₂— | cyclohexyl |
| —CH₃ | —CH₂C(CH₃)₂— | phenyl |
| —CH₃ | —CH₂C(CH₃)₂— | 4-chlorophenyl |
| —CH₃ | —CH₂C(CH₃)₂— | 2,4-dichlorophenyl |
| —CH₃ | —CH₂C(CH₃)₂CH₂— | methyl |
| —CH₃ | —CH₂C(CH₃)₂CH₂— | ethyl |
| —CH₃ | —CH₂C(CH₃)₂CH₂— | n-propyl |
| —CH₃ | —CH₂C(CH₃)₂CH₂— | isopropyl |
| —CH₃ | —CH₂C(CH₃)₂CH₂— | cyclopropyl |
| —CH₃ | —CH₂C(CH₃)₂CH₂— | n-butyl |
| —CH₃ | —CH₂C(CH₃)₂CH₂— | sec-butyl |
| —CH₃ | —CH₂C(CH₃)₂CH₂— | isobutyl |
| —CH₃ | —CH₂C(CH₃)₂CH₂— | tert-butyl |
| —CH₃ | —CH₂C(CH₃)₂CH₂— | n-pentyl |
| —CH₃ | —CH₂C(CH₃)₂CH₂— | cyclopentyl |
| —CH₃ | —CH₂C(CH₃)₂CH₂— | n-hexyl |
| —CH₃ | —CH₂C(CH₃)₂CH₂— | cyclohexyl |
| —CH₃ | —CH₂C(CH₃)₂CH₂— | phenyl |
| —CH₃ | —CH₂C(CH₃)₂CH₂— | 4-chlorophenyl |
| —CH₃ | —CH₂C(CH₃)₂CH₂— | 2,4-dichlorophenyl |
| —CH₃ | —(CH₂)₂OCH₂— | methyl |
| —CH₃ | —(CH₂)₂OCH₂— | ethyl |
| —CH₃ | —(CH₂)₂OCH₂— | n-propyl |
| —CH₃ | —(CH₂)₂OCH₂— | isopropyl |
| —CH₃ | —(CH₂)₂OCH₂— | cyclopropyl |
| —CH₃ | —(CH₂)₂OCH₂— | n-butyl |
| —CH₃ | —(CH₂)₂OCH₂— | sec-butyl |
| —CH₃ | —(CH₂)₂OCH₂— | isobutyl |
| —CH₃ | —(CH₂)₂OCH₂— | tert-butyl |
| —CH₃ | —(CH₂)₂OCH₂— | n-pentyl |
| —CH₃ | —(CH₂)₂OCH₂— | cyclopentyl |
| —CH₃ | —(CH₂)₂OCH₂— | n-hexyl |
| —CH₃ | —(CH₂)₂OCH₂— | cyclohexyl |
| —CH₃ | —(CH₂)₂OCH₂— | phenyl |
| —CH₃ | —(CH₂)₂OCH₂— | 4-chlorophenyl |
| —CH₃ | —(CH₂)₂OCH₂— | 2,4-dichlorophenyl |
| —CH₃ | —(CH₂)₃OCH₂— | methyl |
| —CH₃ | —(CH₂)₃OCH₂— | ethyl |
| —CH₃ | —(CH₂)₃OCH₂— | n-propyl |
| —CH₃ | —(CH₂)₃OCH₂— | isopropyl |
| —CH₃ | —(CH₂)₃OCH₂— | cyclopropyl |
| —CH₃ | —(CH₂)₃OCH₂— | n-butyl |
| —CH₃ | —(CH₂)₃OCH₂— | sec-butyl |
| —CH₃ | —(CH₂)₃OCH₂— | isobutyl |
| —CH₃ | —(CH₂)₃OCH₂— | tert-butyl |
| —CH₃ | —(CH₂)₃OCH₂— | n-pentyl |
| —CH₃ | —(CH₂)₃OCH₂— | cyclopentyl |
| —CH₃ | —(CH₂)₃OCH₂— | n-hexyl |
| —CH₃ | —(CH₂)₃OCH₂— | cyclohexyl |
| —CH₃ | —(CH₂)₃OCH₂— | phenyl |
| —CH₃ | —(CH₂)₃OCH₂— | 4-chlorophenyl |
| —CH₃ | —(CH₂)₃OCH₂— | 2,4-dichlorophenyl |
| —CH₂CH₃ (ethyl) | —CH₂— | methyl |
| —CH₂CH₃ | —CH₂— | ethyl |
| —CH₂CH₃ | —CH₂— | n-propyl |
| —CH₂CH₃ | —CH₂— | isopropyl |
| —CH₂CH₃ | —CH₂— | cyclopropyl |
| —CH₂CH₃ | —CH₂— | n-butyl |
| —CH₂CH₃ | —CH₂— | sec-butyl |
| —CH₂CH₃ | —CH₂— | isobutyl |
| —CH₂CH₃ | —CH₂— | tert-butyl |
| —CH₂CH₃ | —CH₂— | n-pentyl |
| —CH₂CH₃ | —CH₂— | cyclopentyl |
| —CH₂CH₃ | —CH₂— | n-hexyl |
| —CH₂CH₃ | —CH₂— | cyclohexyl |
| —CH₂CH₃ | —CH₂— | phenyl |
| —CH₂CH₃ | —CH₂— | 4-chlorophenyl |
| —CH₂CH₃ | —CH₂— | 2,4-dichlorophenyl |
| —CH₂CH₃ | —(CH₂)₂— | methyl |
| —CH₂CH₃ | —(CH₂)₂— | ethyl |
| —CH₂CH₃ | —(CH₂)₂— | n-propyl |
| —CH₂CH₃ | —(CH₂)₂— | isopropyl |
| —CH₂CH₃ | —(CH₂)₂— | cyclopropyl |
| —CH₂CH₃ | —(CH₂)₂— | n-butyl |
| —CH₂CH₃ | —(CH₂)₂— | sec-butyl |
| —CH₂CH₃ | —(CH₂)₂— | isobutyl |
| —CH₂CH₃ | —(CH₂)₂— | tert-butyl |
| —CH₂CH₃ | —(CH₂)₂— | n-pentyl |
| —CH₂CH₃ | —(CH₂)₂— | cyclopentyl |
| —CH₂CH₃ | —(CH₂)₂— | n-hexyl |
| —CH₂CH₃ | —(CH₂)₂— | cyclohexyl |
| —CH₂CH₃ | —(CH₂)₂— | phenyl |
| —CH₂CH₃ | —(CH₂)₂— | 4-chlorophenyl |
| —CH₂CH₃ | —(CH₂)₂— | 2,4-dichlorophenyl |
| —CH₂CH₃ | —(CH₂)₃— | methyl |
| —CH₂CH₃ | —(CH₂)₃— | ethyl |
| —CH₂CH₃ | —(CH₂)₃— | n-propyl |
| —CH₂CH₃ | —(CH₂)₃— | isopropyl |
| —CH₂CH₃ | —(CH₂)₃— | cyclopropyl |
| —CH₂CH₃ | —(CH₂)₃— | n-butyl |
| —CH₂CH₃ | —(CH₂)₃— | sec-butyl |
| —CH₂CH₃ | —(CH₂)₃— | isobutyl |
| —CH₂CH₃ | —(CH₂)₃— | tert-butyl |
| —CH₂CH₃ | —(CH₂)₃— | n-pentyl |
| —CH₂CH₃ | —(CH₂)₃— | cyclopentyl |
| —CH₂CH₃ | —(CH₂)₃— | n-hexyl |
| —CH₂CH₃ | —(CH₂)₃— | cyclohexyl |
| —CH₂CH₃ | —(CH₂)₃— | phenyl |
| —CH₂CH₃ | —(CH₂)₃— | 4-chlorophenyl |
| —CH₂CH₃ | —(CH₂)₃— | 2,4-dichlorophenyl |
| —CH₂CH₃ | —(CH₂)₄— | methyl |
| —CH₂CH₃ | —(CH₂)₄— | ethyl |
| —CH₂CH₃ | —(CH₂)₄— | n-propyl |
| —CH₂CH₃ | —(CH₂)₄— | isopropyl |
| —CH₂CH₃ | —(CH₂)₄— | cyclopropyl |
| —CH₂CH₃ | —(CH₂)₄— | n-butyl |
| —CH₂CH₃ | —(CH₂)₄— | sec-butyl |
| —CH₂CH₃ | —(CH₂)₄— | isobutyl |
| —CH₂CH₃ | —(CH₂)₄— | tert-butyl |
| —CH₂CH₃ | —(CH₂)₄— | n-pentyl |
| —CH₂CH₃ | —(CH₂)₄— | cyclopentyl |
| —CH₂CH₃ | —(CH₂)₄— | n-hexyl |
| —CH₂CH₃ | —(CH₂)₄— | cyclohexyl |
| —CH₂CH₃ | —(CH₂)₄— | phenyl |
| —CH₂CH₃ | —(CH₂)₄— | 4-chlorophenyl |
| —CH₂CH₃ | —(CH₂)₄— | 2,4-dichlorophenyl |
| —CH₂CH₃ | —(CH₂)₅— | methyl |
| —CH₂CH₃ | —(CH₂)₅— | ethyl |
| —CH₂CH₃ | —(CH₂)₅— | n-propyl |
| —CH₂CH₃ | —(CH₂)₅— | isopropyl |
| —CH₂CH₃ | —(CH₂)₅— | cyclopropyl |
| —CH₂CH₃ | —(CH₂)₅— | n-butyl |
| —CH₂CH₃ | —(CH₂)₅— | sec-butyl |
| —CH₂CH₃ | —(CH₂)₅— | isobutyl |
| —CH₂CH₃ | —(CH₂)₅— | tert-butyl |
| —CH₂CH₃ | —(CH₂)₅— | n-pentyl |
| —CH₂CH₃ | —(CH₂)₅— | cyclopentyl |
| —CH₂CH₃ | —(CH₂)₅— | n-hexyl |
| —CH₂CH₃ | —(CH₂)₅— | cyclohexyl |
| —CH₂CH₃ | —(CH₂)₅— | phenyl |
| —CH₂CH₃ | —(CH₂)₅— | 4-chlorophenyl |
| —CH₂CH₃ | —(CH₂)₅— | 2,4-dichlorophenyl |
| —CH₂CH₃ | —(CH₂)₆— | methyl |
| —CH₂CH₃ | —(CH₂)₆— | ethyl |
| —CH₂CH₃ | —(CH₂)₆— | n-propyl |
| —CH₂CH₃ | —(CH₂)₆— | isopropyl |

| | | |
|---|---|---|
| —CH₂CH₃ | —(CH₂)₆— | cyclopropyl |
| —CH₂CH₃ | —(CH₂)₆— | n-butyl |
| —CH₂CH₃ | —(CH₂)₆— | sec-butyl |
| —CH₂CH₃ | —(CH₂)₆— | isobutyl |
| —CH₂CH₃ | —(CH₂)₆— | tert-butyl |
| —CH₂CH₃ | —(CH₂)₆— | n-pentyl |
| —CH₂CH₃ | —(CH₂)₆— | cyclopentyl |
| —CH₂CH₃ | —(CH₂)₆— | n-hexyl |
| —CH₂CH₃ | —(CH₂)₆— | cyclohexyl |
| —CH₂CH₃ | —(CH₂)₆— | phenyl |
| —CH₂CH₃ | —(CH₂)₆— | 4-chlorophenyl |
| —CH₂CH₃ | —(CH₂)₆— | 2,4-dichlorophenyl |
| —CH₂CH₃ | —CH₂C(CH₃)₂— | methyl |
| —CH₂CH₃ | —CH₂C(CH₃)₂— | ethyl |
| —CH₂CH₃ | —CH₂C(CH₃)₂— | n-propyl |
| —CH₂CH₃ | —CH₂C(CH₃)₂— | isopropyl |
| —CH₂CH₃ | —CH₂C(CH₃)₂— | cyclopropyl |
| —CH₂CH₃ | —CH₂C(CH₃)₂— | n-butyl |
| —CH₂CH₃ | —CH₂C(CH₃)₂— | sec-butyl |
| —CH₂CH₃ | —CH₂C(CH₃)₂— | isobutyl |
| —CH₂CH₃ | —CH₂C(CH₃)₂— | tert-butyl |
| —CH₂CH₃ | —CH₂C(CH₃)₂— | n-pentyl |
| —CH₂CH₃ | —CH₂C(CH₃)₂— | cyclopentyl |
| —CH₂CH₃ | —CH₂C(CH₃)₂— | n-hexyl |
| —CH₂CH₃ | —CH₂C(CH₃)₂— | cyclohexyl |
| —CH₂CH₃ | —CH₂C(CH₃)₂— | phenyl |
| —CH₂CH₃ | —CH₂C(CH₃)₂— | 4-chlorophenyl |
| —CH₂CH₃ | —CH₂C(CH₃)₂— | 2,4-dichlorophenyl |
| —CH₂CH₃ | —CH₂C(CH₃)₂CH₂— | methyl |
| —CH₂CH₃ | —CH₂C(CH₃)₂CH₂— | ethyl |
| —CH₂CH₃ | —CH₂C(CH₃)₂CH₂— | n-propyl |
| —CH₂CH₃ | —CH₂C(CH₃)₂CH₂— | isopropyl |
| —CH₂CH₃ | —CH₂C(CH₃)₂CH₂— | cyclopropyl |
| —CH₂CH₃ | —CH₂C(CH₃)₂CH₂— | n-butyl |
| —CH₂CH₃ | —CH₂C(CH₃)₂CH₂— | sec-butyl |
| —CH₂CH₃ | —CH₂C(CH₃)₂CH₂— | isobutyl |
| —CH₂CH₃ | —CH₂C(CH₃)₂CH₂— | tert-butyl |
| —CH₂CH₃ | —CH₂C(CH₃)₂CH₂— | n-pentyl |
| —CH₂CH₃ | —CH₂C(CH₃)₂CH₂— | cyclopentyl |
| —CH₂CH₃ | —CH₂C(CH₃)₂CH₂— | n-hexyl |
| —CH₂CH₃ | —CH₂C(CH₃)₂CH₂— | cyclohexyl |
| —CH₂CH₃ | —CH₂C(CH₃)₂CH₂— | phenyl |
| —CH₂CH₃ | —CH₂C(CH₃)₂CH₂— | 4-chlorophenyl |
| —CH₂CH₃ | —CH₂C(CH₃)₂CH₂— | 2,4-dichlorophenyl |
| —CH₂CH₃ | —(CH₂)₂OCH₂— | methyl |
| —CH₂CH₃ | —(CH₂)₂OCH₂— | ethyl |
| —CH₂CH₃ | —(CH₂)₂OCH₂— | n-propyl |
| —CH₂CH₃ | —(CH₂)₂OCH₂— | isopropyl |
| —CH₂CH₃ | —(CH₂)₂OCH₂— | cyclopropyl |
| —CH₂CH₃ | —(CH₂)₂OCH₂— | n-butyl |
| —CH₂CH₃ | —(CH₂)₂OCH₂— | sec-butyl |
| —CH₂CH₃ | —(CH₂)₂OCH₂— | isobutyl |
| —CH₂CH₃ | —(CH₂)₂OCH₂— | tert-butyl |
| —CH₂CH₃ | —(CH₂)₂OCH₂— | n-pentyl |
| —CH₂CH₃ | —(CH₂)₂OCH₂— | cyclopentyl |
| —CH₂CH₃ | —(CH₂)₂OCH₂— | n-hexyl |
| —CH₂CH₃ | —(CH₂)₂OCH₂— | cyclohexyl |
| —CH₂CH₃ | —(CH₂)₂OCH₂— | phenyl |
| —CH₂CH₃ | —(CH₂)₂OCH₂— | 4-chlorophenyl |
| —CH₂CH₃ | —(CH₂)₂OCH₂— | 2,4-dichlorophenyl |
| —CH₂CH₃ | —(CH₂)₃OCH₂— | methyl |
| —CH₂CH₃ | —(CH₂)₃OCH₂— | ethyl |
| —CH₂CH₃ | —(CH₂)₃OCH₂— | n-propyl |
| —CH₂CH₃ | —(CH₂)₃OCH₂— | isopropyl |
| —CH₂CH₃ | —(CH₂)₃OCH₂— | cyclopropyl |
| —CH₂CH₃ | —(CH₂)₃OCH₂— | n-butyl |
| —CH₂CH₃ | —(CH₂)₃OCH₂— | sec-butyl |
| —CH₂CH₃ | —(CH₂)₃OCH₂— | isobutyl |
| —CH₂CH₃ | —(CH₂)₃OCH₂— | tert-butyl |
| —CH₂CH₃ | —(CH₂)₃OCH₂— | n-pentyl |
| —CH₂CH₃ | —(CH₂)₃OCH₂— | cyclopentyl |
| —CH₂CH₃ | —(CH₂)₃OCH₂— | n-hexyl |
| —CH₂CH₃ | —(CH₂)₃OCH₂— | cyclohexyl |
| —CH₂CH₃ | —(CH₂)₃OCH₂— | phenyl |
| —CH₂CH₃ | —(CH₂)₃OCH₂— | 4-chlorophenyl |
| —CH₂CH₃ | —(CH₂)₃OCH₂— | 2,4-dichlorophenyl |
| —CH₂CH₂CH₃ (n-propyl) | —CH₂— | methyl |
| —CH₂CH₂CH₃ | —CH₂— | ethyl |
| —CH₂CH₂CH₃ | —CH₂— | n-propyl |
| —CH₂CH₂CH₃ | —CH₂— | isopropyl |
| —CH₂CH₂CH₃ | —CH₂— | cyclopropyl |
| —CH₂CH₂CH₃ | —CH₂— | n-butyl |
| —CH₂CH₂CH₃ | —CH₂— | sec-butyl |
| —CH₂CH₂CH₃ | —CH₂— | isobutyl |
| —CH₂CH₂CH₃ | —CH₂— | tert-butyl |
| —CH₂CH₂CH₃ | —CH₂— | n-pentyl |
| —CH₂CH₂CH₃ | —CH₂— | cyclopentyl |
| —CH₂CH₂CH₃ | —CH₂— | n-hexyl |
| —CH₂CH₂CH₃ | —CH₂— | cyclohexyl |
| —CH₂CH₂CH₃ | —CH₂— | phenyl |
| —CH₂CH₂CH₃ | —CH₂— | 4-chlorophenyl |
| —CH₂CH₂CH₃ | —CH₂— | 2,4-dichlorophenyl |
| —CH₂CH₂CH₃ | —(CH₂)₂— | methyl |
| —CH₂CH₂CH₃ | —(CH₂)₂— | ethyl |
| —CH₂CH₂CH₃ | —(CH₂)₂— | n-propyl |
| —CH₂CH₂CH₃ | —(CH₂)₂— | isopropyl |
| —CH₂CH₂CH₃ | —(CH₂)₂— | cyclopropyl |
| —CH₂CH₂CH₃ | —(CH₂)₂— | n-butyl |
| —CH₂CH₂CH₃ | —(CH₂)₂— | sec-butyl |
| —CH₂CH₂CH₃ | —(CH₂)₂— | isobutyl |
| —CH₂CH₂CH₃ | —(CH₂)₂— | tert-butyl |
| —CH₂CH₂CH₃ | —(CH₂)₂— | n-pentyl |
| —CH₂CH₂CH₃ | —(CH₂)₂— | cyclopentyl |
| —CH₂CH₂CH₃ | —(CH₂)₂— | n-hexyl |
| —CH₂CH₂CH₃ | —(CH₂)₂— | cyclohexyl |
| —CH₂CH₂CH₃ | —(CH₂)₂— | phenyl |
| —CH₂CH₂CH₃ | —(CH₂)₂— | 4-chlorophenyl |
| —CH₂CH₂CH₃ | —(CH₂)₂— | 2,4-dichlorophenyl |
| —CH₂CH₂CH₃ | —(CH₂)₃— | methyl |
| —CH₂CH₂CH₃ | —(CH₂)₃— | ethyl |
| —CH₂CH₂CH₃ | —(CH₂)₃— | n-propyl |
| —CH₂CH₂CH₃ | —(CH₂)₃— | isopropyl |
| —CH₂CH₂CH₃ | —(CH₂)₃— | cyclopropyl |
| —CH₂CH₂CH₃ | —(CH₂)₃— | n-butyl |
| —CH₂CH₂CH₃ | —(CH₂)₃— | sec-butyl |
| —CH₂CH₂CH₃ | —(CH₂)₃— | isobutyl |
| —CH₂CH₂CH₃ | —(CH₂)₃— | tert-butyl |
| —CH₂CH₂CH₃ | —(CH₂)₃— | n-pentyl |
| —CH₂CH₂CH₃ | —(CH₂)₃— | cyclopentyl |
| —CH₂CH₂CH₃ | —(CH₂)₃— | n-hexyl |
| —CH₂CH₂CH₃ | —(CH₂)₃— | cyclohexyl |
| —CH₂CH₂CH₃ | —(CH₂)₃— | phenyl |
| —CH₂CH₂CH₃ | —(CH₂)₃— | 4-chlorophenyl |
| —CH₂CH₂CH₃ | —(CH₂)₃— | 2,4-dichlorophenyl |
| —CH₂CH₂CH₃ | —(CH₂)₄— | methyl |
| —CH₂CH₂CH₃ | —(CH₂)₄— | ethyl |
| —CH₂CH₂CH₃ | —(CH₂)₄— | n-propyl |
| —CH₂CH₂CH₃ | —(CH₂)₄— | isopropyl |
| —CH₂CH₂CH₃ | —(CH₂)₄— | cyclopropyl |
| —CH₂CH₂CH₃ | —(CH₂)₄— | n-butyl |
| —CH₂CH₂CH₃ | —(CH₂)₄— | sec-butyl |
| —CH₂CH₂CH₃ | —(CH₂)₄— | isobutyl |
| —CH₂CH₂CH₃ | —(CH₂)₄— | tert-butyl |
| —CH₂CH₂CH₃ | —(CH₂)₄— | n-pentyl |
| —CH₂CH₂CH₃ | —(CH₂)₄— | cyclopentyl |
| —CH₂CH₂CH₃ | —(CH₂)₄— | n-hexyl |
| —CH₂CH₂CH₃ | —(CH₂)₄— | cyclohexyl |
| —CH₂CH₂CH₃ | —(CH₂)₄— | phenyl |
| —CH₂CH₂CH₃ | —(CH₂)₄— | 4-chlorophenyl |
| —CH₂CH₂CH₃ | —(CH₂)₄— | 2,4-dichlorophenyl |
| —CH₂CH₂CH₃ | —(CH₂)₅— | methyl |
| —CH₂CH₂CH₃ | —(CH₂)₅— | ethyl |
| —CH₂CH₂CH₃ | —(CH₂)₅— | n-propyl |
| —CH₂CH₂CH₃ | —(CH₂)₅— | isopropyl |
| —CH₂CH₂CH₃ | —(CH₂)₅— | cyclopropyl |
| —CH₂CH₂CH₃ | —(CH₂)₅— | n-butyl |
| —CH₂CH₂CH₃ | —(CH₂)₅— | sec-butyl |
| —CH₂CH₂CH₃ | —(CH₂)₅— | isobutyl |
| —CH₂CH₂CH₃ | —(CH₂)₅— | tert-butyl |
| —CH₂CH₂CH₃ | —(CH₂)₅— | n-pentyl |
| —CH₂CH₂CH₃ | —(CH₂)₅— | cyclopentyl |
| —CH₂CH₂CH₃ | —(CH₂)₅— | n-hexyl |
| —CH₂CH₂CH₃ | —(CH₂)₅— | cyclohexyl |
| —CH₂CH₂CH₃ | —(CH₂)₅— | phenyl |
| —CH₂CH₂CH₃ | —(CH₂)₅— | 4-chlorophenyl |
| —CH₂CH₂CH₃ | —(CH₂)₅— | 2,4-dichlorophenyl |
| —CH₂CH₂CH₃ | —(CH₂)₆— | methyl |
| —CH₂CH₂CH₃ | —(CH₂)₆— | ethyl |
| —CH₂CH₂CH₃ | —(CH₂)₆— | n-propyl |
| —CH₂CH₂CH₃ | —(CH₂)₆— | isopropyl |

| | | |
|---|---|---|
| —CH$_2$CH$_2$CH$_3$ | —(CH$_2$)$_6$— | cyclopropyl |
| —CH$_2$CH$_2$CH$_3$ | —(CH$_2$)$_6$— | n-butyl |
| —CH$_2$CH$_2$CH$_3$ | —(CH$_2$)$_6$— | sec-butyl |
| —CH$_2$CH$_2$CH$_3$ | —(CH$_2$)$_6$— | isobutyl |
| —CH$_2$CH$_2$CH$_3$ | —(CH$_2$)$_6$— | tert-butyl |
| —CH$_2$CH$_2$CH$_3$ | —(CH$_2$)$_6$— | n-pentyl |
| —CH$_2$CH$_2$CH$_3$ | —(CH$_2$)$_6$— | cyclopentyl |
| —CH$_2$CH$_2$CH$_3$ | —(CH$_2$)$_6$— | n-hexyl |
| —CH$_2$CH$_2$CH$_3$ | —(CH$_2$)$_6$— | cyclohexyl |
| —CH$_2$CH$_2$CH$_3$ | —(CH$_2$)$_6$— | phenyl |
| —CH$_2$CH$_2$CH$_3$ | —(CH$_2$)$_6$— | 4-chlorophenyl |
| —CH$_2$CH$_2$CH$_3$ | —(CH$_2$)$_6$— | 2,4-dichlorophenyl |
| —CH$_2$CH$_2$CH$_3$ | —CH$_2$C(CH$_3$)$_2$— | methyl |
| —CH$_2$CH$_2$CH$_3$ | —CH$_2$C(CH$_3$)$_2$— | ethyl |
| —CH$_2$CH$_2$CH$_3$ | —CH$_2$C(CH$_3$)$_2$— | n-propyl |
| —CH$_2$CH$_2$CH$_3$ | —CH$_2$C(CH$_3$)$_2$— | isopropyl |
| —CH$_2$CH$_2$CH$_3$ | —CH$_2$C(CH$_3$)$_2$— | cyclopropyl |
| —CH$_2$CH$_2$CH$_3$ | —CH$_2$C(CH$_3$)$_2$— | n-butyl |
| —CH$_2$CH$_2$CH$_3$ | —CH$_2$C(CH$_3$)$_2$— | sec-butyl |
| —CH$_2$CH$_2$CH$_3$ | —CH$_2$C(CH$_3$)$_2$— | isobutyl |
| —CH$_2$CH$_2$CH$_3$ | —CH$_2$C(CH$_3$)$_2$— | tert-butyl |
| —CH$_2$CH$_2$CH$_3$ | —CH$_2$C(CH$_3$)$_2$— | n-pentyl |
| —CH$_2$CH$_2$CH$_3$ | —CH$_2$C(CH$_3$)$_2$— | cyclopentyl |
| —CH$_2$CH$_2$CH$_3$ | —CH$_2$C(CH$_3$)$_2$— | n-hexyl |
| —CH$_2$CH$_2$CH$_3$ | —CH$_2$C(CH$_3$)$_2$— | cyclohexyl |
| —CH$_2$CH$_2$CH$_3$ | —CH$_2$C(CH$_3$)$_2$— | phenyl |
| —CH$_2$CH$_2$CH$_3$ | —CH$_2$C(CH$_3$)$_2$— | 4-chlorophenyl |
| —CH$_2$CH$_2$CH$_3$ | —CH$_2$C(CH$_3$)$_2$— | 2,4-dichlorophenyl |
| —CH$_2$CH$_2$CH$_3$ | —CH$_2$C(CH$_3$)$_2$CH$_2$— | methyl |
| —CH$_2$CH$_2$CH$_3$ | —CH$_2$C(CH$_3$)$_2$CH$_2$— | ethyl |
| —CH$_2$CH$_2$CH$_3$ | —CH$_2$C(CH$_3$)$_2$CH$_2$— | n-propyl |
| —CH$_2$CH$_2$CH$_3$ | —CH$_2$C(CH$_3$)$_2$CH$_2$— | isopropyl |
| —CH$_2$CH$_2$CH$_3$ | —CH$_2$C(CH$_3$)$_2$CH$_2$— | cyclopropyl |
| —CH$_2$CH$_2$CH$_3$ | —CH$_2$C(CH$_3$)$_2$CH$_2$— | n-butyl |
| —CH$_2$CH$_2$CH$_3$ | —CH$_2$C(CH$_3$)$_2$CH$_2$— | sec-butyl |
| —CH$_2$CH$_2$CH$_3$ | —CH$_2$C(CH$_3$)$_2$CH$_2$— | isobutyl |
| —CH$_2$CH$_2$CH$_3$ | —CH$_2$C(CH$_3$)$_2$CH$_2$— | tert-butyl |
| —CH$_2$CH$_2$CH$_3$ | —CH$_2$C(CH$_3$)$_2$CH$_2$— | n-pentyl |
| —CH$_2$CH$_2$CH$_3$ | —CH$_2$C(CH$_3$)$_2$CH$_2$— | cyclopentyl |
| —CH$_2$CH$_2$CH$_3$ | —CH$_2$C(CH$_3$)$_2$CH$_2$— | n-hexyl |
| —CH$_2$CH$_2$CH$_3$ | —CH$_2$C(CH$_3$)$_2$CH$_2$— | cyclohexyl |
| —CH$_2$CH$_2$CH$_3$ | —CH$_2$C(CH$_3$)$_2$CH$_2$— | phenyl |
| —CH$_2$CH$_2$CH$_3$ | —CH$_2$C(CH$_3$)$_2$CH$_2$— | 4-chlorophenyl |
| —CH$_2$CH$_2$CH$_3$ | —CH$_2$C(CH$_3$)$_2$CH$_2$— | 2,4-dichlorophenyl |
| —CH$_2$CH$_2$CH$_3$ | —(CH$_2$)$_2$OCH$_2$— | methyl |
| —CH$_2$CH$_2$CH$_3$ | —(CH$_2$)$_2$OCH$_2$— | ethyl |
| —CH$_2$CH$_2$CH$_3$ | —(CH$_2$)$_2$OCH$_2$— | n-propyl |
| —CH$_2$CH$_2$CH$_3$ | —(CH$_2$)$_2$OCH$_2$— | isopropyl |
| —CH$_2$CH$_2$CH$_3$ | —(CH$_2$)$_2$OCH$_2$— | cyclopropyl |
| —CH$_2$CH$_2$CH$_3$ | —(CH$_2$)$_2$OCH$_2$— | n-butyl |
| —CH$_2$CH$_2$CH$_3$ | —(CH$_2$)$_2$OCH$_2$— | sec-butyl |
| —CH$_2$CH$_2$CH$_3$ | —(CH$_2$)$_2$OCH$_2$— | isobutyl |
| —CH$_2$CH$_2$CH$_3$ | —(CH$_2$)$_2$OCH$_2$— | tert-butyl |
| —CH$_2$CH$_2$CH$_3$ | —(CH$_2$)$_2$OCH$_2$— | n-pentyl |
| —CH$_2$CH$_2$CH$_3$ | —(CH$_2$)$_2$OCH$_2$— | cyclopentyl |
| —CH$_2$CH$_2$CH$_3$ | —(CH$_2$)$_2$OCH$_2$— | n-hexyl |
| —CH$_2$CH$_2$CH$_3$ | —(CH$_2$)$_2$OCH$_2$— | cyclohexyl |
| —CH$_2$CH$_2$CH$_3$ | —(CH$_2$)$_2$OCH$_2$— | phenyl |
| —CH$_2$CH$_2$CH$_3$ | —(CH$_2$)$_2$OCH$_2$— | 4-chlorophenyl |
| —CH$_2$CH$_2$CH$_3$ | —(CH$_2$)$_2$OCH$_2$— | 2,4-dichlorophenyl |
| —CH$_2$CH$_2$CH$_3$ | —(CH$_2$)$_3$OCH$_2$— | methyl |
| —CH$_2$CH$_2$CH$_3$ | —(CH$_2$)$_3$OCH$_2$— | ethyl |
| —CH$_2$CH$_2$CH$_3$ | —(CH$_2$)$_3$OCH$_2$— | n-propyl |
| —CH$_2$CH$_2$CH$_3$ | —(CH$_2$)$_3$OCH$_2$— | isopropyl |
| —CH$_2$CH$_2$CH$_3$ | —(CH$_2$)$_3$OCH$_2$— | cyclopropyl |
| —CH$_2$CH$_2$CH$_3$ | —(CH$_2$)$_3$OCH$_2$— | n-butyl |
| —CH$_2$CH$_2$CH$_3$ | —(CH$_2$)$_3$OCH$_2$— | sec-butyl |
| —CH$_2$CH$_2$CH$_3$ | —(CH$_2$)$_3$OCH$_2$— | isobutyl |
| —CH$_2$CH$_2$CH$_3$ | —(CH$_2$)$_3$OCH$_2$— | tert-butyl |
| —CH$_2$CH$_2$CH$_3$ | —(CH$_2$)$_3$OCH$_2$— | n-pentyl |
| —CH$_2$CH$_2$CH$_3$ | —(CH$_2$)$_3$OCH$_2$— | cyclopentyl |
| —CH$_2$CH$_2$CH$_3$ | —(CH$_2$)$_3$OCH$_2$— | n-hexyl |
| —CH$_2$CH$_2$CH$_3$ | —(CH$_2$)$_3$OCH$_2$— | cyclohexyl |
| —CH$_2$CH$_2$CH$_3$ | —(CH$_2$)$_3$OCH$_2$— | phenyl |
| —CH$_2$CH$_2$CH$_3$ | —(CH$_2$)$_3$OCH$_2$— | 4-chlorophenyl |
| —CH$_2$CH$_2$CH$_3$ | —(CH$_2$)$_3$OCH$_2$— | 2,4-dichlorophenyl |
| —CH$_2$CH$_2$CH$_2$CH$_3$ (n-butyl) | —CH$_2$— | methyl |
| —CH$_2$CH$_2$CH$_2$CH$_3$ | —CH$_2$— | ethyl |
| —CH$_2$CH$_2$CH$_2$CH$_3$ | —CH$_2$— | n-propyl |
| —CH$_2$CH$_2$CH$_2$CH$_3$ | —CH$_2$— | isopropyl |
| —CH$_2$CH$_2$CH$_2$CH$_3$ | —CH$_2$— | cyclopropyl |
| —CH$_2$CH$_2$CH$_2$CH$_3$ | —CH$_2$— | n-butyl |
| —CH$_2$CH$_2$CH$_2$CH$_3$ | —CH$_2$— | sec-butyl |
| —CH$_2$CH$_2$CH$_2$CH$_3$ | —CH$_2$— | isobutyl |
| —CH$_2$CH$_2$CH$_2$CH$_3$ | —CH$_2$— | tert-butyl |
| —CH$_2$CH$_2$CH$_2$CH$_3$ | —CH$_2$— | n-pentyl |
| —CH$_2$CH$_2$CH$_2$CH$_3$ | —CH$_2$— | cyclopentyl |
| —CH$_2$CH$_2$CH$_2$CH$_3$ | —CH$_2$— | n-hexyl |
| —CH$_2$CH$_2$CH$_2$CH$_3$ | —CH$_2$— | cyclohexyl |
| —CH$_2$CH$_2$CH$_2$CH$_3$ | —CH$_2$— | phenyl |
| —CH$_2$CH$_2$CH$_2$CH$_3$ | —CH$_2$— | 4-chlorophenyl |
| —CH$_2$CH$_2$CH$_2$CH$_3$ | —CH$_2$— | 2,4-dichlorophenyl |
| —CH$_2$CH$_2$CH$_2$CH$_3$ | —(CH$_2$)$_2$— | methyl |
| —CH$_2$CH$_2$CH$_2$CH$_3$ | —(CH$_2$)$_2$— | ethyl |
| —CH$_2$CH$_2$CH$_2$CH$_3$ | —(CH$_2$)$_2$— | n-propyl |
| —CH$_2$CH$_2$CH$_2$CH$_3$ | —(CH$_2$)$_2$— | isopropyl |
| —CH$_2$CH$_2$CH$_2$CH$_3$ | —(CH$_2$)$_2$— | cyclopropyl |
| —CH$_2$CH$_2$CH$_2$CH$_3$ | —(CH$_2$)$_2$— | n-butyl |
| —CH$_2$CH$_2$CH$_2$CH$_3$ | —(CH$_2$)$_2$— | sec-butyl |
| —CH$_2$CH$_2$CH$_2$CH$_3$ | —(CH$_2$)$_2$— | isobutyl |
| —CH$_2$CH$_2$CH$_2$CH$_3$ | —(CH$_2$)$_2$— | tert-butyl |
| —CH$_2$CH$_2$CH$_2$CH$_3$ | —(CH$_2$)$_2$— | n-pentyl |
| —CH$_2$CH$_2$CH$_2$CH$_3$ | —(CH$_2$)$_2$— | cyclopentyl |
| —CH$_2$CH$_2$CH$_2$CH$_3$ | —(CH$_2$)$_2$— | n-hexyl |
| —CH$_2$CH$_2$CH$_2$CH$_3$ | —(CH$_2$)$_2$— | cyclohexyl |
| —CH$_2$CH$_2$CH$_2$CH$_3$ | —(CH$_2$)$_2$— | phenyl |
| —CH$_2$CH$_2$CH$_2$CH$_3$ | —(CH$_2$)$_2$— | 4-chlorophenyl |
| —CH$_2$CH$_2$CH$_2$CH$_3$ | —(CH$_2$)$_2$— | 2,4-dichlorophenyl |
| —CH$_2$CH$_2$CH$_2$CH$_3$ | —(CH$_2$)$_3$— | methyl |
| —CH$_2$CH$_2$CH$_2$CH$_3$ | —(CH$_2$)$_3$— | ethyl |
| —CH$_2$CH$_2$CH$_2$CH$_3$ | —(CH$_2$)$_3$— | n-propyl |
| —CH$_2$CH$_2$CH$_2$CH$_3$ | —(CH$_2$)$_3$— | isopropyl |
| —CH$_2$CH$_2$CH$_2$CH$_3$ | —(CH$_2$)$_3$— | cyclopropyl |
| —CH$_2$CH$_2$CH$_2$CH$_3$ | —(CH$_2$)$_3$— | n-butyl |
| —CH$_2$CH$_2$CH$_2$CH$_3$ | —(CH$_2$)$_3$— | sec-butyl |
| —CH$_2$CH$_2$CH$_2$CH$_3$ | —(CH$_2$)$_3$— | isobutyl |
| —CH$_2$CH$_2$CH$_2$CH$_3$ | —(CH$_2$)$_3$— | tert-butyl |
| —CH$_2$CH$_2$CH$_2$CH$_3$ | —(CH$_2$)$_3$— | n-pentyl |
| —CH$_2$CH$_2$CH$_2$CH$_3$ | —(CH$_2$)$_3$— | cyclopentyl |
| —CH$_2$CH$_2$CH$_2$CH$_3$ | —(CH$_2$)$_3$— | n-hexyl |
| —CH$_2$CH$_2$CH$_2$CH$_3$ | —(CH$_2$)$_3$— | cyclohexyl |
| —CH$_2$CH$_2$CH$_2$CH$_3$ | —(CH$_2$)$_3$— | phenyl |
| —CH$_2$CH$_2$CH$_2$CH$_3$ | —(CH$_2$)$_3$— | 4-chlorophenyl |
| —CH$_2$CH$_2$CH$_2$CH$_3$ | —(CH$_2$)$_3$— | 2,4-dichlorophenyl |
| —CH$_2$CH$_2$CH$_2$CH$_3$ | —(CH$_2$)$_4$— | methyl |
| —CH$_2$CH$_2$CH$_2$CH$_3$ | —(CH$_2$)$_4$— | ethyl |
| —CH$_2$CH$_2$CH$_2$CH$_3$ | —(CH$_2$)$_4$— | n-propyl |
| —CH$_2$CH$_2$CH$_2$CH$_3$ | —(CH$_2$)$_4$— | isopropyl |
| —CH$_2$CH$_2$CH$_2$CH$_3$ | —(CH$_2$)$_4$— | cyclopropyl |
| —CH$_2$CH$_2$CH$_2$CH$_3$ | —(CH$_2$)$_4$— | n-butyl |
| —CH$_2$CH$_2$CH$_2$CH$_3$ | —(CH$_2$)$_4$— | sec-butyl |
| —CH$_2$CH$_2$CH$_2$CH$_3$ | —(CH$_2$)$_4$— | isobutyl |
| —CH$_2$CH$_2$CH$_2$CH$_3$ | —(CH$_2$)$_4$— | tert-butyl |
| —CH$_2$CH$_2$CH$_2$CH$_3$ | —(CH$_2$)$_4$— | n-pentyl |
| —CH$_2$CH$_2$CH$_2$CH$_3$ | —(CH$_2$)$_4$— | cyclopentyl |
| —CH$_2$CH$_2$CH$_2$CH$_3$ | —(CH$_2$)$_4$— | n-hexyl |
| —CH$_2$CH$_2$CH$_2$CH$_3$ | —(CH$_2$)$_4$— | cyclohexyl |
| —CH$_2$CH$_2$CH$_2$CH$_3$ | —(CH$_2$)$_4$— | phenyl |
| —CH$_2$CH$_2$CH$_2$CH$_3$ | —(CH$_2$)$_4$— | 4-chlorophenyl |
| —CH$_2$CH$_2$CH$_2$CH$_3$ | —(CH$_2$)$_4$— | 2,4-dichlorophenyl |
| —CH$_2$CH$_2$CH$_2$CH$_3$ | —(CH$_2$)$_5$— | methyl |
| —CH$_2$CH$_2$CH$_2$CH$_3$ | —(CH$_2$)$_5$— | ethyl |
| —CH$_2$CH$_2$CH$_2$CH$_3$ | —(CH$_2$)$_5$— | n-propyl |
| —CH$_2$CH$_2$CH$_2$CH$_3$ | —(CH$_2$)$_5$— | isopropyl |
| —CH$_2$CH$_2$CH$_2$CH$_3$ | —(CH$_2$)$_5$— | cyclopropyl |
| —CH$_2$CH$_2$CH$_2$CH$_3$ | —(CH$_2$)$_5$— | n-butyl |
| —CH$_2$CH$_2$CH$_2$CH$_3$ | —(CH$_2$)$_5$— | sec-butyl |
| —CH$_2$CH$_2$CH$_2$CH$_3$ | —(CH$_2$)$_5$— | isobutyl |
| —CH$_2$CH$_2$CH$_2$CH$_3$ | —(CH$_2$)$_5$— | tert-butyl |
| —CH$_2$CH$_2$CH$_2$CH$_3$ | —(CH$_2$)$_5$— | n-pentyl |
| —CH$_2$CH$_2$CH$_2$CH$_3$ | —(CH$_2$)$_5$— | cyclopentyl |
| —CH$_2$CH$_2$CH$_2$CH$_3$ | —(CH$_2$)$_5$— | n-hexyl |
| —CH$_2$CH$_2$CH$_2$CH$_3$ | —(CH$_2$)$_5$— | cyclohexyl |
| —CH$_2$CH$_2$CH$_2$CH$_3$ | —(CH$_2$)$_5$— | phenyl |
| —CH$_2$CH$_2$CH$_2$CH$_3$ | —(CH$_2$)$_5$— | 4-chlorophenyl |
| —CH$_2$CH$_2$CH$_2$CH$_3$ | —(CH$_2$)$_5$— | 2,4-dichlorophenyl |
| —CH$_2$CH$_2$CH$_2$CH$_3$ | —(CH$_2$)$_6$— | methyl |
| —CH$_2$CH$_2$CH$_2$CH$_3$ | —(CH$_2$)$_6$— | ethyl |
| —CH$_2$CH$_2$CH$_2$CH$_3$ | —(CH$_2$)$_6$— | n-propyl |

| | | |
|---|---|---|
| —CH₂CH₂CH₂CH₃ | —(CH₂)₆— | isopropyl |
| —CH₂CH₂CH₂CH₃ | —(CH₂)₆— | cyclopropyl |
| —CH₂CH₂CH₂CH₃ | —(CH₂)₆— | n-butyl |
| —CH₂CH₂CH₂CH₃ | —(CH₂)₆— | sec-butyl |
| —CH₂CH₂CH₂CH₃ | —(CH₂)₆— | isobutyl |
| —CH₂CH₂CH₂CH₃ | —(CH₂)₆— | tert-butyl |
| —CH₂CH₂CH₂CH₃ | —(CH₂)₆— | n-pentyl |
| —CH₂CH₂CH₂CH₃ | —(CH₂)₆— | cyclopentyl |
| —CH₂CH₂CH₂CH₃ | —(CH₂)₆— | n-hexyl |
| —CH₂CH₂CH₂CH₃ | —(CH₂)₆— | cyclohexyl |
| —CH₂CH₂CH₂CH₃ | —(CH₂)₆— | phenyl |
| —CH₂CH₂CH₂CH₃ | —(CH₂)₆— | 4-chlorophenyl |
| —CH₂CH₂CH₂CH₃ | —(CH₂)₆— | 2,4-dichlorophenyl |
| —CH₂CH₂CH₂CH₃ | —CH₂C(CH₃)₂— | methyl |
| —CH₂CH₂CH₂CH₃ | —CH₂C(CH₃)₂— | ethyl |
| —CH₂CH₂CH₂CH₃ | —CH₂C(CH₃)₂— | n-propyl |
| —CH₂CH₂CH₂CH₃ | —CH₂C(CH₃)₂— | isopropyl |
| —CH₂CH₂CH₂CH₃ | —CH₂C(CH₃)₂— | cyclopropyl |
| —CH₂CH₂CH₂CH₃ | —CH₂C(CH₃)₂— | n-butyl |
| —CH₂CH₂CH₂CH₃ | —CH₂C(CH₃)₂— | sec-butyl |
| —CH₂CH₂CH₂CH₃ | —CH₂C(CH₃)₂— | isobutyl |
| —CH₂CH₂CH₂CH₃ | —CH₂C(CH₃)₂— | tert-butyl |
| —CH₂CH₂CH₂CH₃ | —CH₂C(CH₃)₂— | n-pentyl |
| —CH₂CH₂CH₂CH₃ | —CH₂C(CH₃)₂— | cyclopentyl |
| —CH₂CH₂CH₂CH₃ | —CH₂C(CH₃)₂— | n-hexyl |
| —CH₂CH₂CH₂CH₃ | —CH₂C(CH₃)₂— | cyclohexyl |
| —CH₂CH₂CH₂CH₃ | —CH₂C(CH₃)₂— | phenyl |
| —CH₂CH₂CH₂CH₃ | —CH₂C(CH₃)₂— | 4-chlorophenyl |
| —CH₂CH₂CH₂CH₃ | —CH₂C(CH₃)₂— | 2,4-dichlorophenyl |
| —CH₂CH₂CH₂CH₃ | —CH₂C(CH₃)₂CH₂— | methyl |
| —CH₂CH₂CH₂CH₃ | —CH₂C(CH₃)₂CH₂— | ethyl |
| —CH₂CH₂CH₂CH₃ | —CH₂C(CH₃)₂CH₂— | n-propyl |
| —CH₂CH₂CH₂CH₃ | —CH₂C(CH₃)₂CH₂— | isopropyl |
| —CH₂CH₂CH₂CH₃ | —CH₂C(CH₃)₂CH₂— | cyclopropyl |
| —CH₂CH₂CH₂CH₃ | —CH₂C(CH₃)₂CH₂— | n-butyl |
| —CH₂CH₂CH₂CH₃ | —CH₂C(CH₃)₂CH₂— | sec-butyl |
| —CH₂CH₂CH₂CH₃ | —CH₂C(CH₃)₂CH₂— | isobutyl |
| —CH₂CH₂CH₂CH₃ | —CH₂C(CH₃)₂CH₂— | tert-butyl |
| —CH₂CH₂CH₂CH₃ | —CH₂C(CH₃)₂CH₂— | n-pentyl |
| —CH₂CH₂CH₂CH₃ | —CH₂C(CH₃)₂CH₂— | cyclopentyl |
| —CH₂CH₂CH₂CH₃ | —CH₂C(CH₃)₂CH₂— | n-hexyl |
| —CH₂CH₂CH₂CH₃ | —CH₂C(CH₃)₂CH₂— | cyclohexyl |
| —CH₂CH₂CH₂CH₃ | —CH₂C(CH₃)₂CH₂— | phenyl |
| —CH₂CH₂CH₂CH₃ | —CH₂C(CH₃)₂CH₂— | 4-chlorophenyl |
| —CH₂CH₂CH₂CH₃ | —CH₂C(CH₃)₂CH₂— | 2,4-dichlorophenyl |
| —CH₂CH₂CH₂CH₃ | —(CH₂)₂OCH₂— | methyl |
| —CH₂CH₂CH₂CH₃ | —(CH₂)₂OCH₂— | ethyl |
| —CH₂CH₂CH₂CH₃ | —(CH₂)₂OCH₂— | n-propyl |
| —CH₂CH₂CH₂CH₃ | —(CH₂)₂OCH₂— | isopropyl |
| —CH₂CH₂CH₂CH₃ | —(CH₂)₂OCH₂— | cyclopropyl |
| —CH₂CH₂CH₂CH₃ | —(CH₂)₂OCH₂— | n-butyl |
| —CH₂CH₂CH₂CH₃ | —(CH₂)₂OCH₂— | sec-butyl |
| —CH₂CH₂CH₂CH₃ | —(CH₂)₂OCH₂— | isobutyl |
| —CH₂CH₂CH₂CH₃ | —(CH₂)₂OCH₂— | tert-butyl |
| —CH₂CH₂CH₂CH₃ | —(CH₂)₂OCH₂— | n-pentyl |
| —CH₂CH₂CH₂CH₃ | —(CH₂)₂OCH₂— | cyclopentyl |
| —CH₂CH₂CH₂CH₃ | —(CH₂)₂OCH₂— | n-hexyl |
| —CH₂CH₂CH₂CH₃ | —(CH₂)₂OCH₂— | cyclohexyl |
| —CH₂CH₂CH₂CH₃ | —(CH₂)₂OCH₂— | phenyl |
| —CH₂CH₂CH₂CH₃ | —(CH₂)₂OCH₂— | 4-chlorophenyl |
| —CH₂CH₂CH₂CH₃ | —(CH₂)₂OCH₂— | 2,4-dichlorophenyl |
| —CH₂CH₂CH₂CH₃ | —(CH₂)₃OCH₂— | methyl |
| —CH₂CH₂CH₂CH₃ | —(CH₂)₃OCH₂— | ethyl |
| —CH₂CH₂CH₂CH₃ | —(CH₂)₃OCH₂— | n-propyl |
| —CH₂CH₂CH₂CH₃ | —(CH₂)₃OCH₂— | isopropyl |
| —CH₂CH₂CH₂CH₃ | —(CH₂)₃OCH₂— | cyclopropyl |
| —CH₂CH₂CH₂CH₃ | —(CH₂)₃OCH₂— | n-butyl |
| —CH₂CH₂CH₂CH₃ | —(CH₂)₃OCH₂— | sec-butyl |
| —CH₂CH₂CH₂CH₃ | —(CH₂)₃OCH₂— | isobutyl |
| —CH₂CH₂CH₂CH₃ | —(CH₂)₃OCH₂— | tert-butyl |
| —CH₂CH₂CH₂CH₃ | —(CH₂)₃OCH₂— | n-pentyl |
| —CH₂CH₂CH₂CH₃ | —(CH₂)₃OCH₂— | cyclopentyl |
| —CH₂CH₂CH₂CH₃ | —(CH₂)₃OCH₂— | n-hexyl |
| —CH₂CH₂CH₂CH₃ | —(CH₂)₃OCH₂— | cyclohexyl |
| —CH₂CH₂CH₂CH₃ | —(CH₂)₃OCH₂— | phenyl |
| —CH₂CH₂CH₂CH₃ | —(CH₂)₃OCH₂— | 4-chlorophenyl |
| —CH₂CH₂CH₂CH₃ | —(CH₂)₃OCH₂— | 2,4-dichlorophenyl |
| —CH₂OCH₂CH₃ (ethoxymethyl) | —CH₂— | methyl |
| —CH₂OCH₂CH₃ | —CH₂— | ethyl |
| —CH₂OCH₂CH₃ | —CH₂— | n-propyl |
| —CH₂OCH₂CH₃ | —CH₂— | isopropyl |
| —CH₂OCH₂CH₃ | —CH₂— | cyclopropyl |
| —CH₂OCH₂CH₃ | —CH₂— | n-butyl |
| —CH₂OCH₂CH₃ | —CH₂— | sec-butyl |
| —CH₂OCH₂CH₃ | —CH₂— | isobutyl |
| —CH₂OCH₂CH₃ | —CH₂— | tert-butyl |
| —CH₂OCH₂CH₃ | —CH₂— | n-pentyl |
| —CH₂OCH₂CH₃ | —CH₂— | cyclopentyl |
| —CH₂OCH₂CH₃ | —CH₂— | n-hexyl |
| —CH₂OCH₂CH₃ | —CH₂— | cyclohexyl |
| —CH₂OCH₂CH₃ | —CH₂— | phenyl |
| —CH₂OCH₂CH₃ | —CH₂— | 4-chlorophenyl |
| —CH₂OCH₂CH₃ | —CH₂— | 2,4-dichlorophenyl |
| —CH₂OCH₂CH₃ | —(CH₂)₂— | methyl |
| —CH₂OCH₂CH₃ | —(CH₂)₂— | ethyl |
| —CH₂OCH₂CH₃ | —(CH₂)₂— | n-propyl |
| —CH₂OCH₂CH₃ | —(CH₂)₂— | isopropyl |
| —CH₂OCH₂CH₃ | —(CH₂)₂— | cyclopropyl |
| —CH₂OCH₂CH₃ | —(CH₂)₂— | n-butyl |
| —CH₂OCH₂CH₃ | —(CH₂)₂— | sec-butyl |
| —CH₂OCH₂CH₃ | —(CH₂)₂— | isobutyl |
| —CH₂OCH₂CH₃ | —(CH₂)₂— | tert-butyl |
| —CH₂OCH₂CH₃ | —(CH₂)₂— | n-pentyl |
| —CH₂OCH₂CH₃ | —(CH₂)₂— | cyclopentyl |
| —CH₂OCH₂CH₃ | —(CH₂)₂— | n-hexyl |
| —CH₂OCH₂CH₃ | —(CH₂)₂— | cyclohexyl |
| —CH₂OCH₂CH₃ | —(CH₂)₂— | phenyl |
| —CH₂OCH₂CH₃ | —(CH₂)₂— | 4-chlorophenyl |
| —CH₂OCH₂CH₃ | —(CH₂)₂— | 2,4-dichlorophenyl |
| —CH₂OCH₂CH₃ | —(CH₂)₃— | methyl |
| —CH₂OCH₂CH₃ | —(CH₂)₃— | ethyl |
| —CH₂OCH₂CH₃ | —(CH₂)₃— | n-propyl |
| —CH₂OCH₂CH₃ | —(CH₂)₃— | isopropyl |
| —CH₂OCH₂CH₃ | —(CH₂)₃— | cyclopropyl |
| —CH₂OCH₂CH₃ | —(CH₂)₃— | n-butyl |
| —CH₂OCH₂CH₃ | —(CH₂)₃— | sec-butyl |
| —CH₂OCH₂CH₃ | —(CH₂)₃— | isobutyl |
| —CH₂OCH₂CH₃ | —(CH₂)₃— | tert-butyl |
| —CH₂OCH₂CH₃ | —(CH₂)₃— | n-pentyl |
| —CH₂OCH₂CH₃ | —(CH₂)₃— | cyclopentyl |
| —CH₂OCH₂CH₃ | —(CH₂)₃— | n-hexyl |
| —CH₂OCH₂CH₃ | —(CH₂)₃— | cyclohexyl |
| —CH₂OCH₂CH₃ | —(CH₂)₃— | phenyl |
| —CH₂OCH₂CH₃ | —(CH₂)₃— | 4-chlorophenyl |
| —CH₂OCH₂CH₃ | —(CH₂)₃— | 2,4-dichlorophenyl |
| —CH₂OCH₂CH₃ | —(CH₂)₄— | methyl |
| —CH₂OCH₂CH₃ | —(CH₂)₄— | ethyl |
| —CH₂OCH₂CH₃ | —(CH₂)₄— | n-propyl |
| —CH₂OCH₂CH₃ | —(CH₂)₄— | isopropyl |
| —CH₂OCH₂CH₃ | —(CH₂)₄— | cyclopropyl |
| —CH₂OCH₂CH₃ | —(CH₂)₄— | n-butyl |
| —CH₂OCH₂CH₃ | —(CH₂)₄— | sec-butyl |
| —CH₂OCH₂CH₃ | —(CH₂)₄— | isobutyl |
| —CH₂OCH₂CH₃ | —(CH₂)₄— | tert-butyl |
| —CH₂OCH₂CH₃ | —(CH₂)₄— | n-pentyl |
| —CH₂OCH₂CH₃ | —(CH₂)₄— | cyclopentyl |
| —CH₂OCH₂CH₃ | —(CH₂)₄— | n-hexyl |
| —CH₂OCH₂CH₃ | —(CH₂)₄— | cyclohexyl |
| —CH₂OCH₂CH₃ | —(CH₂)₄— | phenyl |
| —CH₂OCH₂CH₃ | —(CH₂)₄— | 4-chlorophenyl |
| —CH₂OCH₂CH₃ | —(CH₂)₄— | 2,4-dichlorophenyl |
| —CH₂OCH₂CH₃ | —(CH₂)₅— | methyl |
| —CH₂OCH₂CH₃ | —(CH₂)₅— | ethyl |
| —CH₂OCH₂CH₃ | —(CH₂)₅— | n-propyl |
| —CH₂OCH₂CH₃ | —(CH₂)₅— | isopropyl |
| —CH₂OCH₂CH₃ | —(CH₂)₅— | cyclopropyl |
| —CH₂OCH₂CH₃ | —(CH₂)₅— | n-butyl |
| —CH₂OCH₂CH₃ | —(CH₂)₅— | sec-butyl |
| —CH₂OCH₂CH₃ | —(CH₂)₅— | isobutyl |
| —CH₂OCH₂CH₃ | —(CH₂)₅— | tert-butyl |
| —CH₂OCH₂CH₃ | —(CH₂)₅— | n-pentyl |
| —CH₂OCH₂CH₃ | —(CH₂)₅— | cyclopentyl |
| —CH₂OCH₂CH₃ | —(CH₂)₅— | n-hexyl |
| —CH₂OCH₂CH₃ | —(CH₂)₅— | cyclohexyl |
| —CH₂OCH₂CH₃ | —(CH₂)₅— | phenyl |
| —CH₂OCH₂CH₃ | —(CH₂)₅— | 4-chlorophenyl |
| —CH₂OCH₂CH₃ | —(CH₂)₅— | 2,4-dichlorophenyl |
| —CH₂OCH₂CH₃ | —(CH₂)₆— | methyl |
| —CH₂OCH₂CH₃ | —(CH₂)₆— | ethyl |

| | | |
|---|---|---|
| —CH₂OCH₂CH₃ | —(CH₂)₆— | n-propyl |
| —CH₂OCH₂CH₃ | —(CH₂)₆— | isopropyl |
| —CH₂OCH₂CH₃ | —(CH₂)₆— | cyclopropyl |
| —CH₂OCH₂CH₃ | —(CH₂)₆— | n-butyl |
| —CH₂OCH₂CH₃ | —(CH₂)₆— | sec-butyl |
| —CH₂OCH₂CH₃ | —(CH₂)₆— | isobutyl |
| —CH₂OCH₂CH₃ | —(CH₂)₆— | tert-butyl |
| —CH₂OCH₂CH₃ | —(CH₂)₆— | n-pentyl |
| —CH₂OCH₂CH₃ | —(CH₂)₆— | cyclopentyl |
| —CH₂OCH₂CH₃ | —(CH₂)₆— | n-hexyl |
| —CH₂OCH₂CH₃ | —(CH₂)₆— | cyclohexyl |
| —CH₂OCH₂CH₃ | —(CH₂)₆— | phenyl |
| —CH₂OCH₂CH₃ | —(CH₂)₆— | 4-chlorophenyl |
| —CH₂OCH₂CH₃ | —(CH₂)₆— | 2,4-dichlorophenyl |
| —CH₂OCH₂CH₃ | —CH₂C(CH₃)₂— | methyl |
| —CH₂OCH₂CH₃ | —CH₂C(CH₃)₂— | ethyl |
| —CH₂OCH₂CH₃ | —CH₂C(CH₃)₂— | n-propyl |
| —CH₂OCH₂CH₃ | —CH₂C(CH₃)₂— | isopropyl |
| —CH₂OCH₂CH₃ | —CH₂C(CH₃)₂— | cyclopropyl |
| —CH₂OCH₂CH₃ | —CH₂C(CH₃)₂— | n-butyl |
| —CH₂OCH₂CH₃ | —CH₂C(CH₃)₂— | sec-butyl |
| —CH₂OCH₂CH₃ | —CH₂C(CH₃)₂— | isobutyl |
| —CH₂OCH₂CH₃ | —CH₂C(CH₃)₂— | tert-butyl |
| —CH₂OCH₂CH₃ | —CH₂C(CH₃)₂— | n-pentyl |
| —CH₂OCH₂CH₃ | —CH₂C(CH₃)₂— | cyclopentyl |
| —CH₂OCH₂CH₃ | —CH₂C(CH₃)₂— | n-hexyl |
| —CH₂OCH₂CH₃ | —CH₂C(CH₃)₂— | cyclohexyl |
| —CH₂OCH₂CH₃ | —CH₂C(CH₃)₂— | phenyl |
| —CH₂OCH₂CH₃ | —CH₂C(CH₃)₂— | 4-chlorophenyl |
| —CH₂OCH₂CH₃ | —CH₂C(CH₃)₂— | 2,4-dichlorophenyl |
| —CH₂OCH₂CH₃ | —CH₂C(CH₃)₂CH₂— | methyl |
| —CH₂OCH₂CH₃ | —CH₂C(CH₃)₂CH₂— | ethyl |
| —CH₂OCH₂CH₃ | —CH₂C(CH₃)₂CH₂— | n-propyl |
| —CH₂OCH₂CH₃ | —CH₂C(CH₃)₂CH₂— | isopropyl |
| —CH₂OCH₂CH₃ | —CH₂C(CH₃)₂CH₂— | cyclopropyl |
| —CH₂OCH₂CH₃ | —CH₂C(CH₃)₂CH₂— | n-butyl |
| —CH₂OCH₂CH₃ | —CH₂C(CH₃)₂CH₂— | sec-butyl |
| —CH₂OCH₂CH₃ | —CH₂C(CH₃)₂CH₂— | isobutyl |
| —CH₂OCH₂CH₃ | —CH₂C(CH₃)₂CH₂— | tert-butyl |
| —CH₂OCH₂CH₃ | —CH₂C(CH₃)₂CH₂— | n-pentyl |
| —CH₂OCH₂CH₃ | —CH₂C(CH₃)₂CH₂— | cyclopentyl |
| —CH₂OCH₂CH₃ | —CH₂C(CH₃)₂CH₂— | n-hexyl |
| —CH₂OCH₂CH₃ | —CH₂C(CH₃)₂CH₂— | cyclohexyl |
| —CH₂OCH₂CH₃ | —CH₂C(CH₃)₂CH₂— | phenyl |
| —CH₂OCH₂CH₃ | —CH₂C(CH₃)₂CH₂— | 4-chlorophenyl |
| —CH₂OCH₂CH₃ | —CH₂C(CH₃)₂CH₂— | 2,4-dichlorophenyl |
| —CH₂OCH₂CH₃ | —(CH₂)₂OCH₂— | methyl |
| —CH₂OCH₂CH₃ | —(CH₂)₂OCH₂— | ethyl |
| —CH₂OCH₂CH₃ | —(CH₂)₂OCH₂— | n-propyl |
| —CH₂OCH₂CH₃ | —(CH₂)₂OCH₂— | isopropyl |
| —CH₂OCH₂CH₃ | —(CH₂)₂OCH₂— | cyclopropyl |
| —CH₂OCH₂CH₃ | —(CH₂)₂OCH₂— | n-butyl |
| —CH₂OCH₂CH₃ | —(CH₂)₂OCH₂— | sec-butyl |
| —CH₂OCH₂CH₃ | —(CH₂)₂OCH₂— | isobutyl |
| —CH₂OCH₂CH₃ | —(CH₂)₂OCH₂— | tert-butyl |
| —CH₂OCH₂CH₃ | —(CH₂)₂OCH₂— | n-pentyl |
| —CH₂OCH₂CH₃ | —(CH₂)₂OCH₂— | cyclopentyl |
| —CH₂OCH₂CH₃ | —(CH₂)₂OCH₂— | n-hexyl |
| —CH₂OCH₂CH₃ | —(CH₂)₂OCH₂— | cyclohexyl |
| —CH₂OCH₂CH₃ | —(CH₂)₂OCH₂— | phenyl |
| —CH₂OCH₂CH₃ | —(CH₂)₂OCH₂— | 4-chlorophenyl |
| —CH₂OCH₂CH₃ | —(CH₂)₂OCH₂— | 2,4-dichlorophenyl |
| —CH₂OCH₂CH₃ | —(CH₂)₃OCH₂— | methyl |
| —CH₂OCH₂CH₃ | —(CH₂)₃OCH₂— | ethyl |
| —CH₂OCH₂CH₃ | —(CH₂)₃OCH₂— | n-propyl |
| —CH₂OCH₂CH₃ | —(CH₂)₃OCH₂— | isopropyl |
| —CH₂OCH₂CH₃ | —(CH₂)₃OCH₂— | cyclopropyl |
| —CH₂OCH₂CH₃ | —(CH₂)₃OCH₂— | n-butyl |
| —CH₂OCH₂CH₃ | —(CH₂)₃OCH₂— | sec-butyl |
| —CH₂OCH₂CH₃ | —(CH₂)₃OCH₂— | isobutyl |
| —CH₂OCH₂CH₃ | —(CH₂)₃OCH₂— | tert-butyl |
| —CH₂OCH₂CH₃ | —(CH₂)₃OCH₂— | n-pentyl |
| —CH₂OCH₂CH₃ | —(CH₂)₃OCH₂— | cyclopentyl |
| —CH₂OCH₂CH₃ | —(CH₂)₃OCH₂— | n-hexyl |
| —CH₂OCH₂CH₃ | —(CH₂)₃OCH₂— | cyclohexyl |
| —CH₂OCH₂CH₃ | —(CH₂)₃OCH₂— | phenyl |
| —CH₂OCH₂CH₃ | —(CH₂)₃OCH₂— | 4-chlorophenyl |
| —CH₂OCH₂CH₃ | —(CH₂)₃OCH₂— | 2,4-dichlorophenyl |
| —CH₂CH₂OCH₃ (2-methoxyethyl) | —CH₂— | methyl |
| —CH₂CH₂OCH₃ | —CH₂— | ethyl |
| —CH₂CH₂OCH₃ | —CH₂— | n-propyl |
| —CH₂CH₂OCH₃ | —CH₂— | isopropyl |
| —CH₂CH₂OCH₃ | —CH₂— | cyclopropyl |
| —CH₂CH₂OCH₃ | —CH₂— | n-butyl |
| —CH₂CH₂OCH₃ | —CH₂— | sec-butyl |
| —CH₂CH₂OCH₃ | —CH₂— | isobutyl |
| —CH₂CH₂OCH₃ | —CH₂— | tert-butyl |
| —CH₂CH₂OCH₃ | —CH₂— | n-pentyl |
| —CH₂CH₂OCH₃ | —CH₂— | cyclopentyl |
| —CH₂CH₂OCH₃ | —CH₂— | n-hexyl |
| —CH₂CH₂OCH₃ | —CH₂— | cyclohexyl |
| —CH₂CH₂OCH₃ | —CH₂— | phenyl |
| —CH₂CH₂OCH₃ | —CH₂— | 4-chlorophenyl |
| —CH₂CH₂OCH₃ | —CH₂— | 2,4-dichlorophenyl |
| —CH₂CH₂OCH₃ | —(CH₂)₂— | methyl |
| —CH₂CH₂OCH₃ | —(CH₂)₂— | ethyl |
| —CH₂CH₂OCH₃ | —(CH₂)₂— | n-propyl |
| —CH₂CH₂OCH₃ | —(CH₂)₂— | isopropyl |
| —CH₂CH₂OCH₃ | —(CH₂)₂— | cyclopropyl |
| —CH₂CH₂OCH₃ | —(CH₂)₂— | n-butyl |
| —CH₂CH₂OCH₃ | —(CH₂)₂— | sec-butyl |
| —CH₂CH₂OCH₃ | —(CH₂)₂— | isobutyl |
| —CH₂CH₂OCH₃ | —(CH₂)₂— | tert-butyl |
| —CH₂CH₂OCH₃ | —(CH₂)₂— | n-pentyl |
| —CH₂CH₂OCH₃ | —(CH₂)₂— | cyclopentyl |
| —CH₂CH₂OCH₃ | —(CH₂)₂— | n-hexyl |
| —CH₂CH₂OCH₃ | —(CH₂)₂— | cyclohexyl |
| —CH₂CH₂OCH₃ | —(CH₂)₂— | phenyl |
| —CH₂CH₂OCH₃ | —(CH₂)₂— | 4-chlorophenyl |
| —CH₂CH₂OCH₃ | —(CH₂)₂— | 2,4-dichlorophenyl |
| —CH₂CH₂OCH₃ | —(CH₂)₃— | methyl |
| —CH₂CH₂OCH₃ | —(CH₂)₃— | ethyl |
| —CH₂CH₂OCH₃ | —(CH₂)₃— | n-propyl |
| —CH₂CH₂OCH₃ | —(CH₂)₃— | isopropyl |
| —CH₂CH₂OCH₃ | —(CH₂)₃— | cyclopropyl |
| —CH₂CH₂OCH₃ | —(CH₂)₃— | n-butyl |
| —CH₂CH₂OCH₃ | —(CH₂)₃— | sec-butyl |
| —CH₂CH₂OCH₃ | —(CH₂)₃— | isobutyl |
| —CH₂CH₂OCH₃ | —(CH₂)₃— | tert-butyl |
| —CH₂CH₂OCH₃ | —(CH₂)₃— | n-pentyl |
| —CH₂CH₂OCH₃ | —(CH₂)₃— | cyclopentyl |
| —CH₂CH₂OCH₃ | —(CH₂)₃— | n-hexyl |
| —CH₂CH₂OCH₃ | —(CH₂)₃— | cyclohexyl |
| —CH₂CH₂OCH₃ | —(CH₂)₃— | phenyl |
| —CH₂CH₂OCH₃ | —(CH₂)₃— | 4-chlorophenyl |
| —CH₂CH₂OCH₃ | —(CH₂)₃— | 2,4-dichlorophenyl |
| —CH₂CH₂OCH₃ | —(CH₂)₄— | methyl |
| —CH₂CH₂OCH₃ | —(CH₂)₄— | ethyl |
| —CH₂CH₂OCH₃ | —(CH₂)₄— | n-propyl |
| —CH₂CH₂OCH₃ | —(CH₂)₄— | isopropyl |
| —CH₂CH₂OCH₃ | —(CH₂)₄— | cyclopropyl |
| —CH₂CH₂OCH₃ | —(CH₂)₄— | n-butyl |
| —CH₂CH₂OCH₃ | —(CH₂)₄— | sec-butyl |
| —CH₂CH₂OCH₃ | —(CH₂)₄— | isobutyl |
| —CH₂CH₂OCH₃ | —(CH₂)₄— | tert-butyl |
| —CH₂CH₂OCH₃ | —(CH₂)₄— | n-pentyl |
| —CH₂CH₂OCH₃ | —(CH₂)₄— | cyclopentyl |
| —CH₂CH₂OCH₃ | —(CH₂)₄— | n-hexyl |
| —CH₂CH₂OCH₃ | —(CH₂)₄— | cyclohexyl |
| —CH₂CH₂OCH₃ | —(CH₂)₄— | phenyl |
| —CH₂CH₂OCH₃ | —(CH₂)₄— | 4-chlorophenyl |
| —CH₂CH₂OCH₃ | —(CH₂)₄— | 2,4-dichlorophenyl |
| —CH₂CH₂OCH₃ | —(CH₂)₅— | methyl |
| —CH₂CH₂OCH₃ | —(CH₂)₅— | ethyl |
| —CH₂CH₂OCH₃ | —(CH₂)₅— | n-propyl |
| —CH₂CH₂OCH₃ | —(CH₂)₅— | isopropyl |
| —CH₂CH₂OCH₃ | —(CH₂)₅— | cyclopropyl |
| —CH₂CH₂OCH₃ | —(CH₂)₅— | n-butyl |
| —CH₂CH₂OCH₃ | —(CH₂)₅— | sec-butyl |
| —CH₂CH₂OCH₃ | —(CH₂)₅— | isobutyl |
| —CH₂CH₂OCH₃ | —(CH₂)₅— | tert-butyl |
| —CH₂CH₂OCH₃ | —(CH₂)₅— | n-pentyl |
| —CH₂CH₂OCH₃ | —(CH₂)₅— | cyclopentyl |
| —CH₂CH₂OCH₃ | —(CH₂)₅— | n-hexyl |
| —CH₂CH₂OCH₃ | —(CH₂)₅— | cyclohexyl |
| —CH₂CH₂OCH₃ | —(CH₂)₅— | phenyl |
| —CH₂CH₂OCH₃ | —(CH₂)₅— | 4-chlorophenyl |
| —CH₂CH₂OCH₃ | —(CH₂)₅— | 2,4-dichlorophenyl |
| —CH₂CH₂OCH₃ | —(CH₂)₆— | methyl |

-continued

| | | |
|---|---|---|
| —CH₂CH₂OCH₃ | —(CH₂)₆— | ethyl |
| —CH₂CH₂OCH₃ | —(CH₂)₆— | n-propyl |
| —CH₂CH₂OCH₃ | —(CH₂)₆— | isopropyl |
| —CH₂CH₂OCH₃ | —(CH₂)₆— | cyclopropyl |
| —CH₂CH₂OCH₃ | —(CH₂)₆— | n-butyl |
| —CH₂CH₂OCH₃ | —(CH₂)₆— | sec-butyl |
| —CH₂CH₂OCH₃ | —(CH₂)₆— | isobutyl |
| —CH₂CH₂OCH₃ | —(CH₂)₆— | tert-butyl |
| —CH₂CH₂OCH₃ | —(CH₂)₆— | n-pentyl |
| —CH₂CH₂OCH₃ | —(CH₂)₆— | cyclopentyl |
| —CH₂CH₂OCH₃ | —(CH₂)₆— | n-hexyl |
| —CH₂CH₂OCH₃ | —(CH₂)₆— | cyclohexyl |
| —CH₂CH₂OCH₃ | —(CH₂)₆— | phenyl |
| —CH₂CH₂OCH₃ | —(CH₂)₆— | 4-chlorophenyl |
| —CH₂CH₂OCH₃ | —(CH₂)₆— | 2,4-dichlorophenyl |
| —CH₂CH₂OCH₃ | —CH₂C(CH₃)₂— | methyl |
| —CH₂CH₂OCH₃ | —CH₂C(CH₃)₂— | ethyl |
| —CH₂CH₂OCH₃ | —CH₂C(CH₃)₂— | n-propyl |
| —CH₂CH₂OCH₃ | —CH₂C(CH₃)₂— | isopropyl |
| —CH₂CH₂OCH₃ | —CH₂C(CH₃)₂— | cyclopropyl |
| —CH₂CH₂OCH₃ | —CH₂C(CH₃)₂— | n-butyl |
| —CH₂CH₂OCH₃ | —CH₂C(CH₃)₂— | sec-butyl |
| —CH₂CH₂OCH₃ | —CH₂C(CH₃)₂— | isobutyl |
| —CH₂CH₂OCH₃ | —CH₂C(CH₃)₂— | tert-butyl |
| —CH₂CH₂OCH₃ | —CH₂C(CH₃)₂— | n-pentyl |
| —CH₂CH₂OCH₃ | —CH₂C(CH₃)₂— | cyclopentyl |
| —CH₂CH₂OCH₃ | —CH₂C(CH₃)₂— | n-hexyl |
| —CH₂CH₂OCH₃ | —CH₂C(CH₃)₂— | cyclohexyl |
| —CH₂CH₂OCH₃ | —CH₂C(CH₃)₂— | phenyl |
| —CH₂CH₂OCH₃ | —CH₂C(CH₃)₂— | 4-chlorophenyl |
| —CH₂CH₂OCH₃ | —CH₂C(CH₃)₂— | 2,4-dichlorophenyl |
| —CH₂CH₂OCH₃ | —CH₂C(CH₃)₂CH₂— | methyl |
| —CH₂CH₂OCH₃ | —CH₂C(CH₃)₂CH₂— | ethyl |
| —CH₂CH₂OCH₃ | —CH₂C(CH₃)₂CH₂— | n-propyl |
| —CH₂CH₂OCH₃ | —CH₂C(CH₃)₂CH₂— | isopropyl |
| —CH₂CH₂OCH₃ | —CH₂C(CH₃)₂CH₂— | cyclopropyl |
| —CH₂CH₂OCH₃ | —CH₂C(CH₃)₂CH₂— | n-butyl |
| —CH₂CH₂OCH₃ | —CH₂C(CH₃)₂CH₂— | sec-butyl |
| —CH₂CH₂OCH₃ | —CH₂C(CH₃)₂CH₂— | isobutyl |
| —CH₂CH₂OCH₃ | —CH₂C(CH₃)₂CH₂— | tert-butyl |
| —CH₂CH₂OCH₃ | —CH₂C(CH₃)₂CH₂— | n-pentyl |
| —CH₂CH₂OCH₃ | —CH₂C(CH₃)₂CH₂— | cyclopentyl |
| —CH₂CH₂OCH₃ | —CH₂C(CH₃)₂CH₂— | n-hexyl |
| —CH₂CH₂OCH₃ | —CH₂C(CH₃)₂CH₂— | cyclohexyl |
| —CH₂CH₂OCH₃ | —CH₂C(CH₃)₂CH₂— | phenyl |
| —CH₂CH₂OCH₃ | —CH₂C(CH₃)₂CH₂— | 4-chlorophenyl |
| —CH₂CH₂OCH₃ | —CH₂C(CH₃)₂CH₂— | 2,4-dichlorophenyl |
| —CH₂CH₂OCH₃ | —(CH₂)₂OCH₂— | methyl |
| —CH₂CH₂OCH₃ | —(CH₂)₂OCH₂— | ethyl |
| —CH₂CH₂OCH₃ | —(CH₂)₂OCH₂— | n-propyl |
| —CH₂CH₂OCH₃ | —(CH₂)₂OCH₂— | isopropyl |
| —CH₂CH₂OCH₃ | —(CH₂)₂OCH₂— | cyclopropyl |
| —CH₂CH₂OCH₃ | —(CH₂)₂OCH₂— | n-butyl |
| —CH₂CH₂OCH₃ | —(CH₂)₂OCH₂— | sec-butyl |
| —CH₂CH₂OCH₃ | —(CH₂)₂OCH₂— | isobutyl |
| —CH₂CH₂OCH₃ | —(CH₂)₂OCH₂— | tert-butyl |
| —CH₂CH₂OCH₃ | —(CH₂)₂OCH₂— | n-pentyl |
| —CH₂CH₂OCH₃ | —(CH₂)₂OCH₂— | cyclopentyl |
| —CH₂CH₂OCH₃ | —(CH₂)₂OCH₂— | n-hexyl |
| —CH₂CH₂OCH₃ | —(CH₂)₂OCH₂— | cyclohexyl |
| —CH₂CH₂OCH₃ | —(CH₂)₂OCH₂— | phenyl |
| —CH₂CH₂OCH₃ | —(CH₂)₂OCH₂— | 4-chlorophenyl |
| —CH₂CH₂OCH₃ | —(CH₂)₂OCH₂— | 2,4-dichlorophenyl |
| —CH₂CH₂OCH₃ | —(CH₂)₃OCH₂— | methyl |
| —CH₂CH₂OCH₃ | —(CH₂)₃OCH₂— | ethyl |
| —CH₂CH₂OCH₃ | —(CH₂)₃OCH₂— | n-propyl |
| —CH₂CH₂OCH₃ | —(CH₂)₃OCH₂— | isopropyl |
| —CH₂CH₂OCH₃ | —(CH₂)₃OCH₂— | cyclopropyl |
| —CH₂CH₂OCH₃ | —(CH₂)₃OCH₂— | n-butyl |
| —CH₂CH₂OCH₃ | —(CH₂)₃OCH₂— | sec-butyl |
| —CH₂CH₂OCH₃ | —(CH₂)₃OCH₂— | isobutyl |
| —CH₂CH₂OCH₃ | —(CH₂)₃OCH₂— | tert-butyl |
| —CH₂CH₂OCH₃ | —(CH₂)₃OCH₂— | n-pentyl |
| —CH₂CH₂OCH₃ | —(CH₂)₃OCH₂— | cyclopentyl |
| —CH₂CH₂OCH₃ | —(CH₂)₃OCH₂— | n-hexyl |
| —CH₂CH₂OCH₃ | —(CH₂)₃OCH₂— | cyclohexyl |
| —CH₂CH₂OCH₃ | —(CH₂)₃OCH₂— | phenyl |
| —CH₂CH₂OCH₃ | —(CH₂)₃OCH₂— | 4-chlorophenyl |
| —CH₂CH₂OCH₃ | —(CH₂)₃OCH₂— | 2,4-dichlorophenyl |

Cytokine Induction in Human Cells

Compounds of the invention have been found to induce cytokine biosynthesis when tested using the method described below.

An in vitro human blood cell system is used to assess cytokine induction. Activity is based on the measurement of interferon and tumor necrosis factor (α) (IFN and TNF, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into EDTA vacutainer tubes. Peripheral blood mononuclear cells (PBMC) are separated from whole blood by density gradient centrifugation using HISTOPAQUE-1077. Blood is diluted 1:1 with Dulbecco's Phosphate Buffered Saline (DPBS) or Hank's Balanced Salts Solution (HBSS). The PBMC layer is collected and washed twice with DPBS or HBSS and resuspended at $4 \times 10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (30-0.014 µM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) by ELISA and for tumor necrosis factor (α) by ELISA or IGEN Assay.

Interferon (α) and Tumor Necrosis Factor (α) Analysis by ELISA

Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Biosource International, Camarillo, Calif. Alternately, the TNF concentration can be determined by ORIGEN M-Series Immunoassay and read on an IGEN M-8 analyzer from IGEN International, Gaithersburg, Md. The immunoassay uses a human TNF capture and detection antibody pair from Biosource International, Camarillo, Calif. Results are expressed in pg/mL.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:
1. A compound of the Formula (I-1):

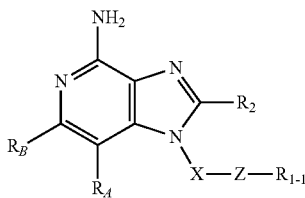

wherein:
X is alkylene;
Z is —C(O)—;
$R_{1-1}$ is selected from the group consisting of:
  hydrogen,
  alkyl,
  phenyl,
  —N(CH$_3$)(OCH$_3$), and
  alkyl or phenyl, substituted by one or more substituents selected from the group consisting of:
    halogen,
    alkoxy,
    dialkylamino,
    alkylthio,
    haloalkyl,
    haloalkoxy, and
    alkyl; and
$R_2$ is selected from the group consisting of:
  hydrogen,
  alkyl,
  hydroxyalkyl, and
  alkyloxyalkyl;
$R_A$ and $R_B$ are taken together to form either a fused aryl ring that is unsubstituted or substituted by one or more R groups, or a fused 5 to 7 membered saturated ring that is unsubstituted or substituted by one or more $R_a$ groups;
  R is selected from the group consisting of:
    fluoro,
    alkyl,
    haloalkyl,
    alkoxy, and
    —N(R$_9$)$_2$; and
  $R_a$ is selected from the group consisting of:
    halogen,
    hydroxy,
    alkyl,
    alkenyl,
    haloalkyl,
    alkoxy,
    alkylthio, and
    —N(R$_9$)$_2$; and R9 is selected from the group consisting of hydrogen and alkyl;
or a pharmaceutically acceptable salt thereof.

2. A compound of the Formula (I-2):

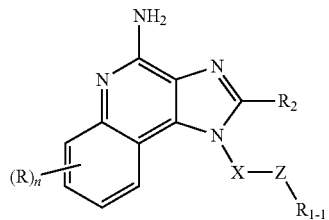

wherein:
X is alkylene;
n is an integer from 0 to 4;
Z is —C(O)—;
$R_{1-1}$ is selected from the group consisting of:
  hydrogen,
  alkyl,
  phenyl,
  —N(CH$_3$)(OCH$_3$), and
  alkyl or phenyl, substituted by one or more substituents selected from the group consisting of:
    halogen,
    alkoxy,
    dialkylamino,
    alkylthio,
    haloalkyl,
    haloalkoxy, and
    alkyl;
R is selected from the group consisting of:
  fluoro,
  alkyl,
  haloalkyl,
  alkoxy, and
  —N(R$_9$)$_2$;
$R_2$ is selected from the group consisting of:
  hydrogen,
  alkyl,
  hydroxyalkyl, and
  alkyloxyalkyl; and
$R_9$ is selected from the group consisting of hydrogen and alkyl;
or a pharmaceutically acceptable salt thereof.

3. A compound of the Formula (Ia):

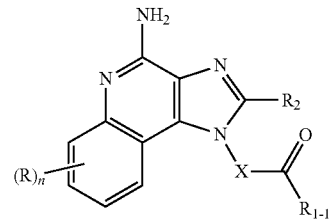

wherein:
X is alkylene;
n is an integer from 0 to 4;
$R_{1-1}$ is selected from the group consisting of:
  hydrogen,
  alkyl,
  phenyl,
  —N(CH$_3$)(OCH$_3$), and
  alkyl or phenyl, substituted by one or more substituents selected from the group consisting of:

halogen,
alkoxy,
dialkylamino,
alkylthio,
haloalkyl,
haloalkoxy, and
alkyl;
R is selected from the group consisting of:
fluoro,
alkyl,
haloalkyl,
alkoxy, and
—N($R_9$)$_2$;
$R_2$ is selected from the group consisting of:
hydrogen,
alkyl,
hydroxyalkyl, and
alkyloxyalkyl; and
$R_9$ is selected from the group consisting of hydrogen and alkyl;
or a pharmaceutically acceptable salt thereof.

4. A compound of the Formula (Ie):

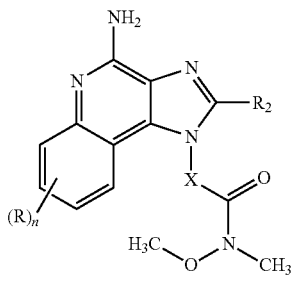

Ie wherein:
X is alkylene;
n is an integer from 0 to 4;
R is selected from the group consisting of:
fluoro,
alkyl,
alkoxy,
haloalkyl, and
—N($R_9$)$_2$;
$R_2$ is selected from the group consisting of:
hydrogen,
alkyl,
hydroxyalkyl, and
alkyloxyalkyl; and
$R_9$ is selected from the group consisting of hydrogen and alkyl;
or a pharmaceutically acceptable salt thereof.

5. The compound or salt of claim 2 wherein n is 0.

6. The compound or salt of claim 1 wherein $R_{1-1}$ is selected from the group consisting of phenyl, alkyl, and —N(CH$_3$)OCH$_3$.

7. The compound or salt of claim 1 wherein X is $C_{1-6}$alkylene.

8. The compound or salt of claim 7 wherein X is selected from the group consisting of —(CH$_2$)$_{1-6}$—, —CH$_2$—C(CH$_3$)$_2$—, and —CH$_2$—C(CH$_3$)$_2$—CH$_2$—.

9. The compound or salt of claim 1 wherein $R_{1-1}$ is selected from the group consisting of alkyl and phenyl.

10. The compound or salt of claim 1 wherein $R_{1-1}$ is selected from the group consisting of methyl, ethyl, n-propyl, isopropyl, cyclopropyl, n-butyl, sec-butyl, isobutyl, tent-butyl, n-pentyl, cyclopentyl, n-hexyl, cyclohexyl, phenyl, 4-chlorophenyl and 2,4-dichlorophenyl.

11. The compound or salt of claim 1 wherein $R_2$ is selected from the group consisting of hydrogen, hydroxymethyl, methyl, ethyl, n-propyl, n-butyl, ethoxymethyl, and 2-methoxyethyl.

12. A pharmaceutical composition comprising a therapeutically effective amount of a compound or salt of claim 1 in combination with a pharmaceutically acceptable carrier.

13. A method of inducing cytokine biosynthesis in an animal comprising administering an effective amount of a compound or salt of claim 1 to the animal wherein the cytokine is selected from INF and TNF.

14. The compound or salt of claim 2 wherein X is $C_{1-6}$alkylene.

15. The compound or salt of claim 14 wherein X is selected from the group consisting of —(CH$_2$)$_{1-6}$—, —CH$_2$—C(CH$_3$)$_2$—, and —CH$_2$—C(CH$_3$)$_2$—CH$_2$—.

16. The compound or salt of claim 2 wherein $R_{1-1}$ is selected from the group consisting of alkyl and phenyl.

17. The compound or salt of claim 2 wherein $R_{1-1}$ is selected from the group consisting of methyl, ethyl, n-propyl, isopropyl, cyclopropyl, n-butyl, sec-butyl, isobutyl, tent-butyl, n-pentyl, cyclopentyl, n-hexyl, cyclohexyl, phenyl, 4-chlorophenyl and 2,4-dichlorophenyl.

18. The compound or salt of claim 2 wherein $R_2$ is selected from the group consisting of hydrogen, hydroxymethyl, methyl, ethyl, n-propyl, n-butyl, ethoxymethyl, and 2-methoxyethyl.

19. A pharmaceutical composition comprising a therapeutically effective amount of a compound or salt of claim 2 in combination with a pharmaceutically acceptable carrier.

20. A method of inducing cytokine biosynthesis in an animal comprising administering an effective amount of a compound or salt of claim 2 to the animal wherein the cytokine is selected from INF and TNF.

21. A pharmaceutical composition comprising a therapeutically effective amount of a compound or salt of claim 4 in combination with a pharmaceutically acceptable carrier.

22. A method of inducing cytokine biosynthesis in an animal comprising administering an effective amount of a compound or salt of claim 4 to the animal wherein the cytokine is selected from INF and TNF.

* * * * *

UNITED STATES PATENT AND TRADEMARK OFFICE
CERTIFICATE OF CORRECTION

PATENT NO.        : 8,691,837 B2
APPLICATION NO.   : 10/595959
DATED             : April 8, 2014
INVENTOR(S)       : Larry Krepski Page 1 of 5

It is certified that error appears in the above-identified patent and that said Letters Patent is hereby corrected as shown below:

TITLE PAGE:

Page 7, Column 1 (Other Publications)
Line 60, Delete "etal.," and insert -- et al., --, therefor.

Page 9, Column 1 (Other Publications)
Line 12, Delete "of al.," and insert -- et al., --, therefor.

Page 9, Column 2 (Other Publications)
Line 45, Delete "et at.," and insert -- et al., --, therefor.

IN THE SPECIFICATION:

Column 4
Line 48, Delete "-$R_{1-13})_2$—;" and insert -- -$R_{1-3})_2$—; --, therefor.

Column 7
Line 25, Delete "thereof" and insert -- thereof. --, therefor.

Column 11
Line 38, Delete "—C(R)—," and insert -- —C($R_6$)—, --, therefor.
Line 39, Delete "—C(R)—O—," and insert -- —C($R_6$)—O—, --, therefor.
Line 40, Delete "—O—C(R)—," and insert -- —O—($R_6$)—, --, therefor.

Column 15
Line 17, Delete "P In another embodiment, there is provided a compound of the Formula (Ia):" and insert -- In another embodiment, there is provided a compound of the Formula (Ia): --, therefor, as new paragraph on Col. 15, Line 20.

Signed and Sealed this
Sixth Day of January, 2015

Michelle K. Lee
*Deputy Director of the United States Patent and Trademark Office*

Column 17
Line 22, Delete "S)$_2$" and insert -- SO$_2$ --, therefor.

Column 18
Line 56, Delete "S)$_2$" and insert -- SO$_2$ --, therefor.

Column 20
Line 10, Delete "thereof" and insert -- thereof. --, therefor.

Column 21
Line 1, Delete "R$_3$" and insert -- R$_9$ --, therefor.
Line 28, Delete "alkyl aryl," and insert -- alkyl, aryl, --, therefor.

Column 23
Line 45, Delete "R$_{1-6}$" and insert -- R$_{1-4}$ --, therefor.

Column 25
Line 16, Delete "norbornyl." and insert -- norbornenyl. --, therefor.

Column 26
Line 28, Delete "—S())$_{0-2}$—," and insert -- —S(O)$_{0-2}$—, --, therefor.
Line 44, After "—CH$_2$—C(CH$_3$)$_2$—," insert -- —CH$_2$—. --.

Line 62-66, Delete " " and insert --  , --, therefor.

Column 27

Line 1-5, Delete " " and insert -- 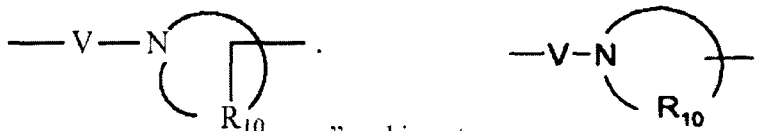 . --, therefor.

Column 28

Line 61-67, Delete " " and insert -- 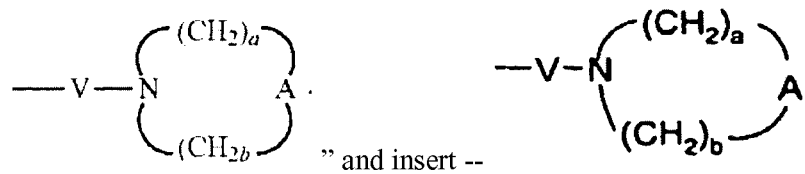 . --, therefor.

Column 35
Line 22, Delete "(O—R$_{1-4}$)$_2$," and insert -- (O—R$_{1-6}$)$_2$, --, therefor.

Column 37
Line 39, Delete "XIX-B," and insert -- XIX-b, --, therefor.

Column 43
Line 29-41, Below "methods." delete "Reaction Scheme 5 ... isolated using conventional methods.", (repeated paragraph).

Column 47
Line 17, Delete "t o" and insert -- to --, therefor.
Line 18, Delete "7,wherein" and insert -- 7, wherein --, therefor.
Line 19, Delete "R2b, R$_{1-1}$b, and Xb" and insert -- R$_{2b}$, R$_{1-1b}$, and X$_b$ --, therefor.

Column 49
Line 22, Delete "(82 g/kg)" and insert -- (µg/kg) --, therefor.

Column 50
Line 30, Delete "picomavirus" and insert -- picornavirus --, therefor.
Line 48, Delete "fingal" and insert -- fungal --, therefor.

Column 53
Line 18, Delete "I M" and insert -- 1 M --, therefor.
Line 33, Delete "warn" and insert -- warm --, therefor.

Column 60
Line 37, Delete "7.1 1;" and insert -- 7.11; --, therefor.

Column 72
Line 7, Delete "(trirethylsilyloxy)" and insert -- (trimethylsilyloxy) --, therefor.

Column 76
Line 33, Delete "7.1 1;" and insert -- 7.11; --, therefor.

Column 77
Line 41, Delete "N-" and insert -- N$^4$- --, therefor.

Column 87
Line 13, Delete "CHC13," and insert -- CHCl3, --, therefor.
Line 26, Delete "I-3 a)" and insert -- I-3a) --, therefor.

Column 92
Line 27, Delete "phenyl" and insert -- ethyl --, therefor.
Line 63, Delete "2,4-dichloro hen l" and insert -- 2,4-dichlorophenyl --, therefor.

Column 94
Line 2, Delete "cyploroyl" and insert -- cyclopropyl --, therefor.

Column 103
Line 9, Delete "Lert" and insert -- Tert --, therefor.

CERTIFICATE OF CORRECTION (continued)
U.S. Pat. No. 8,691,837 B2

IN THE CLAIMS:

Column 105
Line 65, In Claim 1, Delete "R9" and insert -- $R_9$ --, therefor.

Column 106

Line 5-14, In Claim 2, Delete " 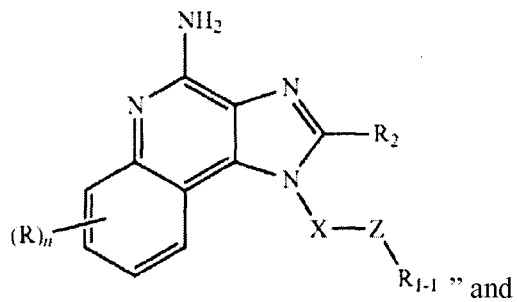 " and insert -- 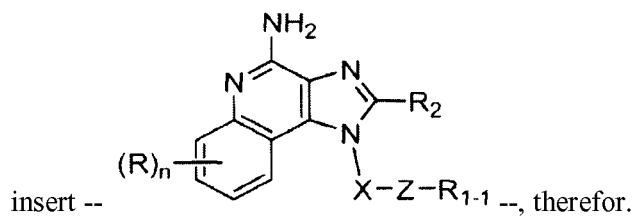 --, therefor.

Column 107

Line 26-36, In Claim 4, Delete " 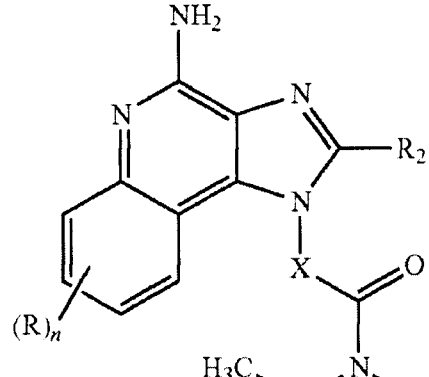 " and insert -- 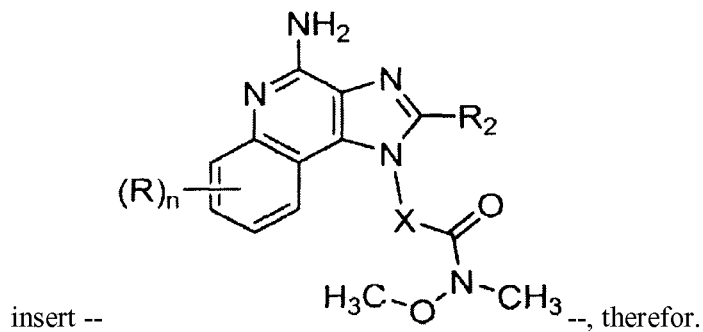 --, therefor.

Column 108

Line 1, In Claim 6, Delete "$R_{1-1}$is" and insert -- $R_{1-1}$ is --, therefor.
Line 4-5, In Claim 7, Delete "$C_{1-6}$alkylene." and insert -- $C_{1-6}$ alkylene. --, therefor.
Line 13, In Claim 10, Delete "tent-" and insert -- tert- --, therefor.
Line 26-27, In Claim 14, Delete "$C_{1-6}$alkylene." and insert -- $C_{1-6}$ alkylene. --, therefor.
Line 31, In Claim 16, Delete "$R_{1-1}$is" and insert -- $R_{1-1}$ is --, therefor.
Line 33, In Claim 17, Delete "$R_{1-1}$is" and insert -- $R_{1-1}$ is --, therefor.
Line 35, In Claim 17, Delete "tent-" and insert -- tert- --, therefor.